(12) United States Patent
Dillon et al.

(10) Patent No.: US 11,819,489 B2
(45) Date of Patent: Nov. 21, 2023

(54) ANTI-CANCER AGENT COMPRISING A TUMOUR HOMING PEPTIDE HAVING ARSENIC BONDED TO CYSTEINE RESIDUES

(71) Applicant: University of Wollongong, Wollongong (AU)

(72) Inventors: Carolyn Therese Dillon, Wollongong (AU); Judith Anne Carrall, Wollongong (AU)

(73) Assignee: University of Wollongong, Wollongong (AU)

( * ) Notice: Subject to any disclaimer, the term of this patent is extended or adjusted under 35 U.S.C. 154(b) by 113 days.

(21) Appl. No.: 16/756,767

(22) PCT Filed: Oct. 17, 2018

(86) PCT No.: PCT/AU2018/000202
§ 371 (c)(1),
(2) Date: Apr. 16, 2020

(87) PCT Pub. No.: WO2019/075507
PCT Pub. Date: Apr. 25, 2019

(65) Prior Publication Data
US 2021/0205259 A1 Jul. 8, 2021

(30) Foreign Application Priority Data

Oct. 17, 2017 (AU) .............................. 2017904199

(51) Int. Cl.
*A61K 38/00* (2006.01)
*A61K 31/285* (2006.01)
*A61P 35/02* (2006.01)
*A61K 33/00* (2006.01)
*A61K 51/08* (2006.01)

(52) U.S. Cl.
CPC ............ *A61K 31/285* (2013.01); *A61K 33/00* (2013.01); *A61K 51/088* (2013.01); *A61P 35/02* (2018.01)

(58) Field of Classification Search
CPC .... A61K 31/285; A61K 33/00; A61K 51/088; A61P 35/02
See application file for complete search history.

(56) References Cited

FOREIGN PATENT DOCUMENTS

| WO | 2004042079 A1 | 5/2004 |
| WO | 2008134761 A2 | 11/2008 |
| WO | 2009075870 A1 | 6/2009 |

OTHER PUBLICATIONS

Madani et al., J.Am.Chem.Soc., 2009 131, 4613-4615. (Year: 2009).*
Happersberger et al., Analytical Biochemistry 264, 237-250 (1998). (Year: 1998).*
Cline, D. J. et al., "Effects of As(III) Binding on a-Helical Structure," Journal of the American Chemical Society (2003) 125(10), pp. 2923-2929.
Happersbergger, H. P. et al., "Selective bridging of bis cysteinyl residues by arsonous acid derivatives as an approach to the characterization of protein tertiary structures and folding pathways by mass spectrometry," Analytical Biochemistry (1988), 264(2), pp. 237-250.
Zhou, X. et al., "Differential Binding of Monomethylarsonous Acid Compared to Arsenite and Arsenic Trioxide with Zinc Finger Peptides and Proteins," Chemical Research in Toxicology (2014), 27(4), pp. 690-698.
PCT International Search Report and Written Opinion dated Dec. 19, 2018 for International Application No. PCT/AU2018/000202, 8 pages.
EP Patent Application No. 18868922.8, Extended European Search Report dated Jun. 15, 2021, 9 pages.
Wilson et al., "Organic Arsenicals as Efficient and Highly Specific Linkers for Protein/Peptide-Polymer Conjugation," Journal of the American Chemical Society, vol. 137, No. 12, Mar. 20, 2015, pp. 4215-4222.
Liu et al., "Tumor-targeting peptides from combinatorial libraries," Advanced Drug Delivery Reviews, vol. 110, May 19, 2016, pp. 13-37.
Ramadan et al., "Effects of As(III) Binding on B-Hairpin Structure," Journal of the American Chemical Society, vol. 129, No. 10, 2007, pp. 2981-2988.
Sahara et al., "The cytocidal effect and mechanism of an arsenic compound Phenylarsineoxide (C6H5AsO; PAO) on acute promyelocytic leukemia cell line," Jpn. J. Cancer Res, 2002, vol. 61, p. 446.
Nishimura et al. "Combinatorial Targeting of the Macropinocytotic Pathway in Leukemia and Lymphoma Cells," J. Biol. Chem, 2008, vol. 283, No. 17, pp. 11752-11762.
Bruno et al., "Inhibition of Bcr-Abl in Human Leukemic Cells with a Coiled-Coil Protein Delivered by a Leukemia-Specific Cell-Penetrating Peptide," Mol. Pharmaceutics, 2015, vol. 12, pp. 1412-1421.
Duro-Castano et al., "Modulating angiogenesis with integrin-targeted nanomedicines" Advanced Drug Delivery Reviews, vol. 119, May 12, 2017, pp. 101-119.
Wu et al., "Targeted mesoporous silica nanoparticles delivering arsenic trioxide with environment sensitive drug release for effective treatment of triple negative breast cancer," ACS Biomater. Sci. Eng., vol. 2, No. 4, 2016, pp. 501-507.
Antman, "Introduction: The History of Arsenic Trioxide in Cancer Therapy," The Oncologist, 2001, vol. 6, Suppl 2, pp. 11-12.
Trisenox (Arsenic trioxide) injection label, Jun. 2010. 14 pages.

(Continued)

*Primary Examiner* — Robert S Cabral
(74) *Attorney, Agent, or Firm* — Fredrikson & Byron, P.A.

(57) ABSTRACT

An anti-cancer agent is provided comprising a tumour homing peptide having, or having been modified to present, two cysteine residues, with an arsenic atom between, such that the tumour homing peptide cyclises to give an arsenic-containing anti-cancer agent. This allows for selection of an appropriate tumour homing peptide for treatment of a given cancer whereby the subsequent agent provides for a more targeted delivery of arsenic to the tumour microenvironment.

19 Claims, 28 Drawing Sheets

(56) References Cited

OTHER PUBLICATIONS

Gautam, A. et al., "Tumor Homing Peptides as Molecular Probes for Cancer Therapeutics, Diagnostics, and Theranostics," Current Medicinal Chemistry (2014), 21, 2367-2391.

Enbäck, J et al., "Tumour-homing peptides: tools for targeting, imaging and destruction," Biochemical Society Transactions (2007), vol. 35, part 4, 780-783.

Laakkonen, P. et al., "Homing peptides as targeted delivery vehicles," Integr. Biol. (2010), 2, 326-337.

* cited by examiner

ANTI-CANCER AGENT COMPRISING A TUMOUR HOMING PEPTIDE HAVING ARSENIC BONDED TO CYSTEINE RESIDUES

CROSS-REFERENCE

This application is a 35 U.S.C. 371 national stage filing from International Application No. PCT/AU2018/000202 filed Oct. 17, 2018, which claims priority to Australian Application No. 2017904199, filed Oct. 17, 2017. The entire contents of both of these applications are incorporated herein by reference.

FIELD OF THE INVENTION

The invention relates to the field of medical treatment. More particularly, this invention relates to arsenic coordinated to peptides and the use of the resulting complexes as anti-cancer agents.

BACKGROUND TO THE INVENTION

Any reference to background art herein is not to be construed as an admission that such art constitutes common general knowledge in Australia or elsewhere.

Although arsenic trioxide ($As_2O_3$, ATO) is a well-known poison, it has been in medical use for a long time. In 1865, arsenic compounds, (one of which was known as Fowler's Solution (a solution containing 1% ATO)), were described for the treatment of chronic myelogenous leukemia. These were replaced, due to their chronic toxicity, with better tolerated agents in the middle of the 20th century. However, following large scale clinical screening, the therapeutic effects of ATO have been identified in certain human cancers such as leukemia, oesophageal carcinoma, and lymphoma. It is currently used for the treatment of haematological malignancies such as acute promyelocytic leukemia.

Arsenic exhibits its toxic, and conversely therapeutic effects, through a variety of mechanisms which involve a number of cellular targets. Arsenic readily bonds with the sulfur in cysteine or methionine amino acid residues (which are found in proteins/enzymes) thereby disrupting a wide range of cellular functions and ultimately resulting in cell death. Some well-studied examples of proteins targeted by trivalent arsenic include glutathione reductase, thioredoxin reductase, mitochondrial adenine nucleotide translocase (ANT), and tubulin. Any of these interactions lead to cell death. For example, mitochondria produce energy within the cell such that disruptions to their functioning results in cell death. Interaction of arsenic with tubulin disrupts microtubule formation preventing cell replication. Additionally arsenic accumulation within the cell nucleus results in DNA fragmentation.

Acute promyelocytic leukemia (APL) is an aggressive form of leukemia that can cause mortality within three months, if left untreated. One of the most effective current treatments for APL is ATO which successfully cures 85% of patients who have relapsed following other therapies. ATO was approved in late 2015 for first line APL combination therapy. It exhibits multifaceted behaviour which is beneficial for overcoming resistance; as such it has invoked considerable interest for treatment of a range of other cancers, particularly haematological malignancies.

Unfortunately, ATO induces toxic side effects which can limit the dose of the anti-cancer drug that can be administered in treatment of APL and other cancers. This can lead to incomplete tumour response, the development of adverse cardiac events, drug resistance, discontinuation of treatment and, ultimately, the progression of the disease. The underlying cause of the toxic side effects stems from the fact that arsenic-containing anti-cancer drugs, such as ATO, indiscriminately kill both cancerous and healthy cells.

SUMMARY OF INVENTION

According to a first aspect of the invention, there is provided an anti-cancer agent comprising a cyclised tumour homing peptide having an arsenic atom bonded to two cysteine residues.

Suitably, the arsenic atom bonded to the two cysteine residues allows the tumour homing peptide to be cyclic. That is, it is the bridging of the arsenic between two cysteines which generates the cyclised tumour homing peptide.

In one embodiment, the two arsenic-bonded cysteine residues of the tumour homing peptide are separated, one from the other, by less than 20 amino acid residues.

In certain embodiments, the two arsenic-bonded cysteine residues of the tumour homing peptide are separated by less than 18 amino acid residues, or less than 16 amino acid residues, or less than 15 amino acid residues, or less than 14 amino acid residues.

In embodiments, prior to cyclisation to form the anti-cancer agent, the two cysteine residues which bind the arsenic atom are the respective N-terminal and C-terminal peptide residues of the tumour homing peptide.

If not naturally present on the tumour homing peptide, the two cysteine residues which bind the arsenic atom can be added onto the tumour homing peptide to thereby form the respective N-terminal and C-terminal peptide residues.

The N-terminal cysteine may comprise a capping group bonded to its terminal amino nitrogen.

In an embodiment, the anti-cancer agent further comprises a stabilising group bonded to the arsenic atom.

Suitably, the stabilising group is selected from the group consisting of hydroxyl, $C_1$ to $C_6$ alkyl, $C_2$ to $C_6$ alkenyl, $C_2$ to $C_6$ alkynyl, aryl, cycloalkyl and heterocyclic.

In embodiments, the tumour homing peptide comprises at least one arginine and/or lysine residue.

In one embodiment, the anti-cancer agent has a structure as shown in formula I:

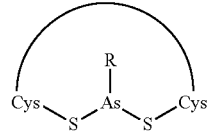

formula I wherein, the sulfur atoms to which the arsenic is bonded are the thiyl sulfurs of the respective cysteine residues;
the cysteine residues in formula I are separated by less than 20 amino acid residues represented by the curved line; and
R is a stabilising group selected from the group consisting of hydroxyl, $C_1$ to $C_6$ alkyl, $C_2$ to $C_6$ alkenyl, $C_2$ to $C_6$ alkynyl, $C_1$ to $C_6$ alkoxy, aryl, cycloalkyl, glutathiyl and heterocyclic, each of which groups may be substituted or unsubstituted.

According to a second aspect of the invention, there is provided a pharmaceutical composition comprising an anti-cancer agent of the first aspect and a pharmaceutically acceptable carrier, diluent and/or excipient.

According to a third aspect of the invention there is provided a method of treating a cancer in a patient including the step of administering an anti-cancer agent of the first aspect or the pharmaceutical composition of the second aspect to the patient, to thereby treat the cancer.

A fourth aspect of the invention resides in an anti-cancer agent of the first aspect for use in treating a cancer in a patient.

A fifth aspect of the invention resides in the use of an anti-cancer agent of the first aspect in the manufacture of a medicament for the treatment of a cancer.

In relation to the third to fifth aspects, in one embodiment the cancer is a haematological malignancy or a solid tumour.

According to a sixth aspect of the invention there is provided a process for producing an anti-cancer agent including the steps of:
(a) contacting a tumour homing peptide comprising two cysteine residues with an arsenic compound; and
(b) allowing the arsenic to become bound to each of the two cysteine residues to form a cyclised tumour homing peptide comprising a bound arsenic atom;
to thereby produce the anti-cancer agent.

The anti-cancer agent may be as described for the first aspect.

The arsenic compound may be an oxide of arsenic.

In one embodiment, the arsenic compound may comprise an alkyl, hydroxyl or aryl group bonded to arsenic.

In one embodiment, the process may comprise the step (a)(i) of modifying a selected tumour homing peptide to present two cysteine residues.

A seventh aspect of the invention resides in an anti-cancer agent when produced by the process of the sixth aspect.

An eighth aspect of the invention resides in a method of delivering a therapeutically effective amount of arsenic to a patient including the step of administering to the patient an appropriate amount of the anti-cancer agent of the first aspect or the pharmaceutical composition of the second aspect, to thereby deliver the therapeutically effective amount of arsenic.

The method of the eighth aspect may include any of the embodiments described for the first aspect.

A ninth aspect of the invention resides in a method of diagnosing a cancer including the steps of:
(i) administering an anti-cancer agent of the first aspect comprising at least one radiolabelled atom, to a patient;
(ii) allowing the anti-cancer agent to become localised to the cancer; and
(iii) detecting the presence of the at least one radiolabelled atom of the anti-cancer agent,
to thereby diagnose the cancer.

The various features and embodiments of the present invention, referred to in individual sections above apply, as appropriate, to other sections, mutatis mutandis. Consequently, features specified in one section may be combined with features specified in other sections as appropriate.

Further features and advantages of the present invention will become apparent from the following detailed description.

BRIEF DESCRIPTION OF THE DRAWINGS

In order that the invention may be readily understood and put into practical effect, preferred embodiments will now be described by way of example with reference to the accompanying figures wherein.

Figure 29:
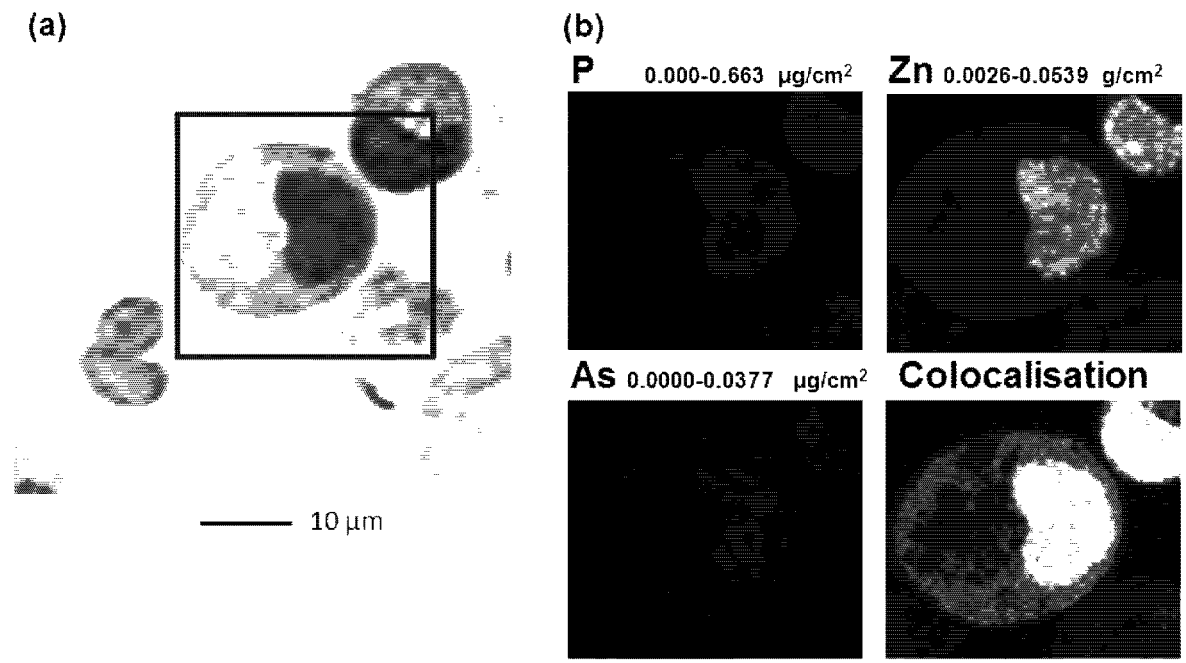
Figure 30:
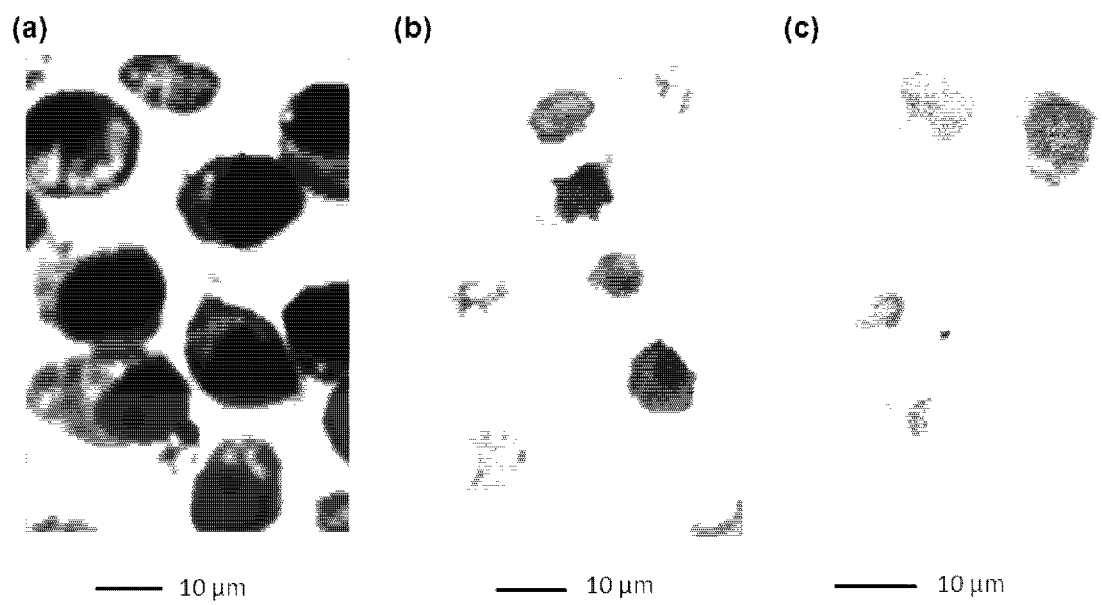
Figure 31:
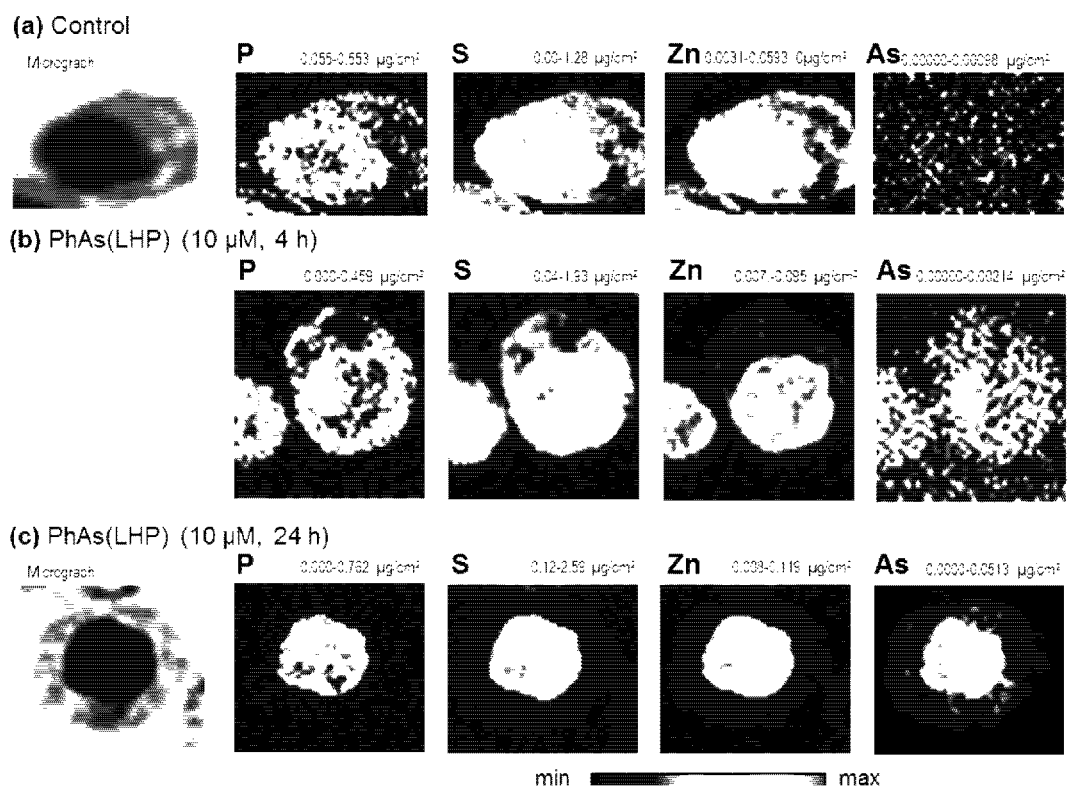
Figure 32:
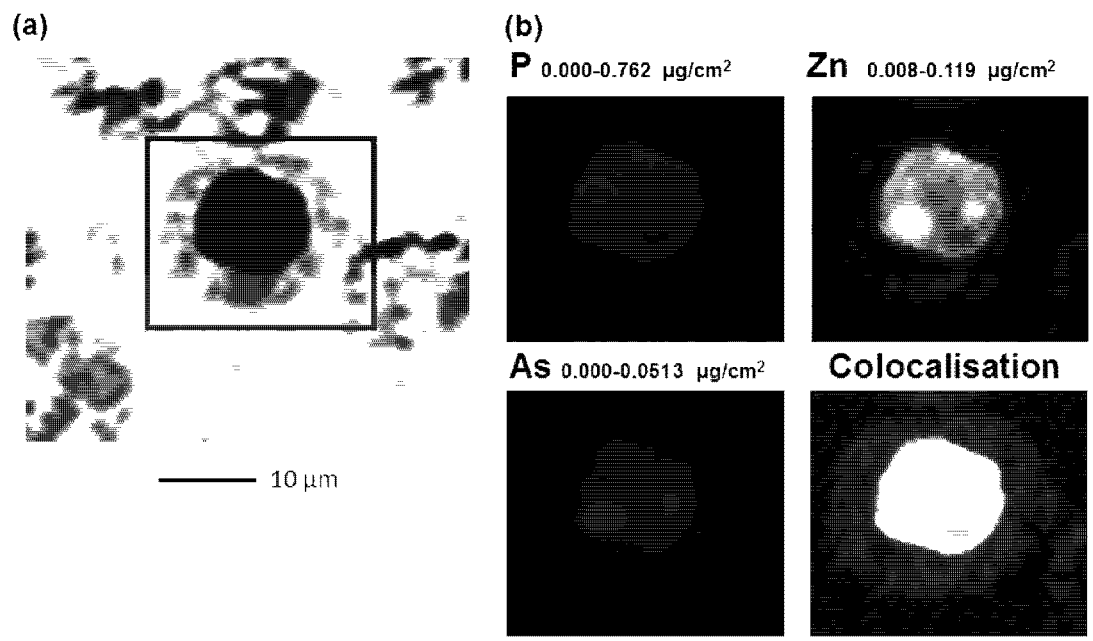
Figure 33:
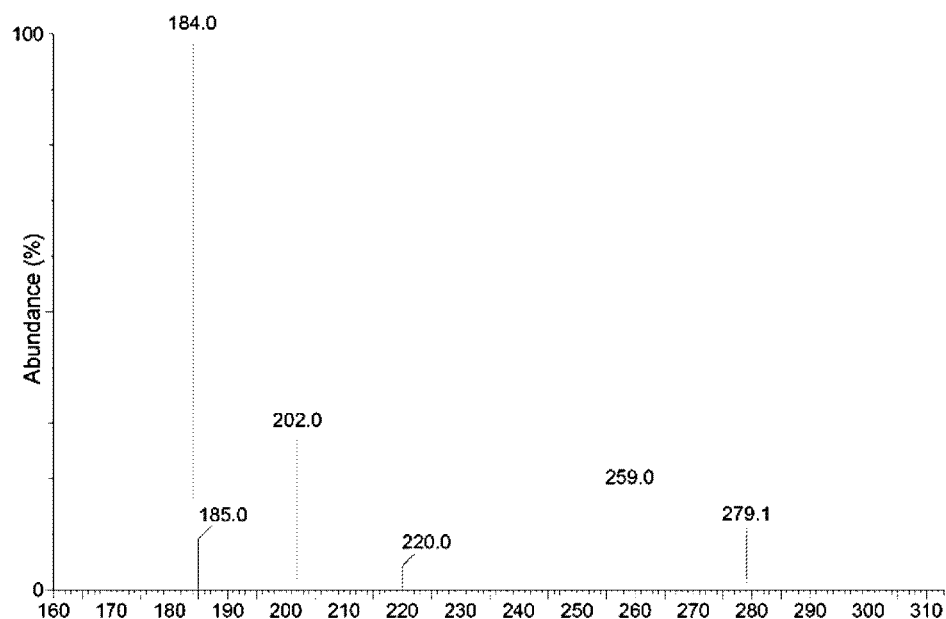
Figure 34:
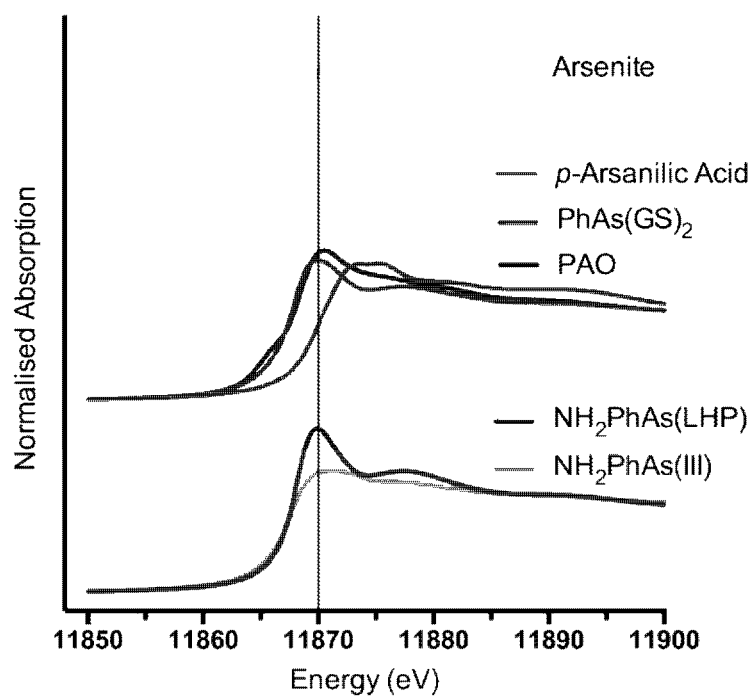
Figure 35:
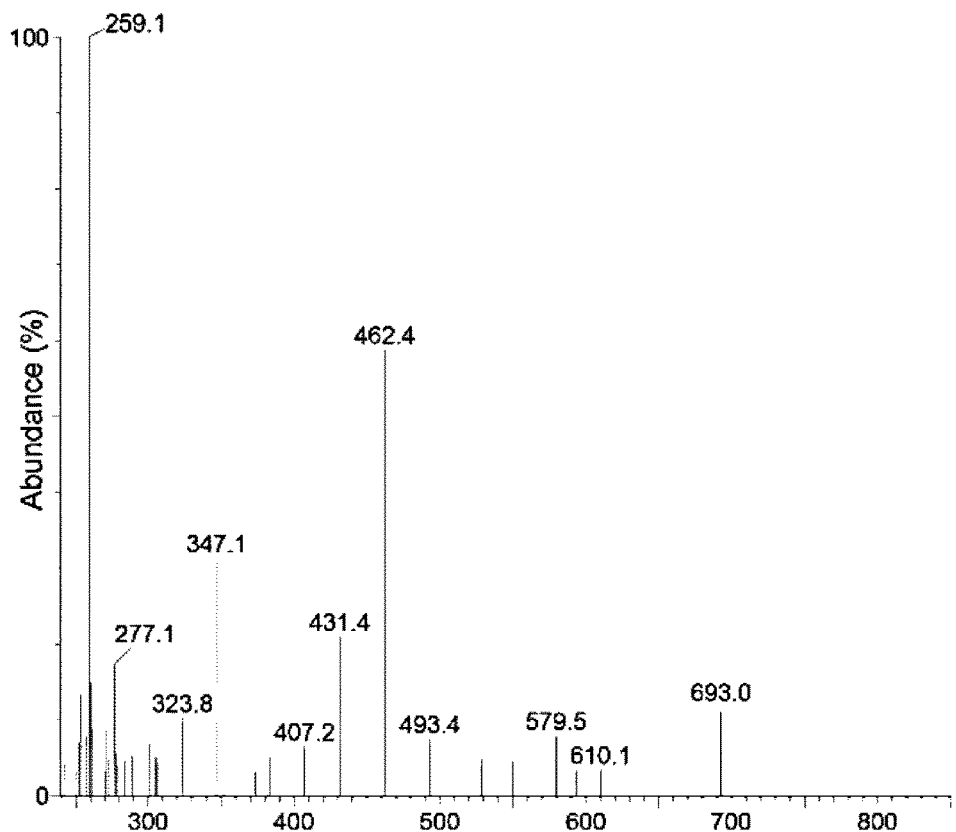
Figure 36:
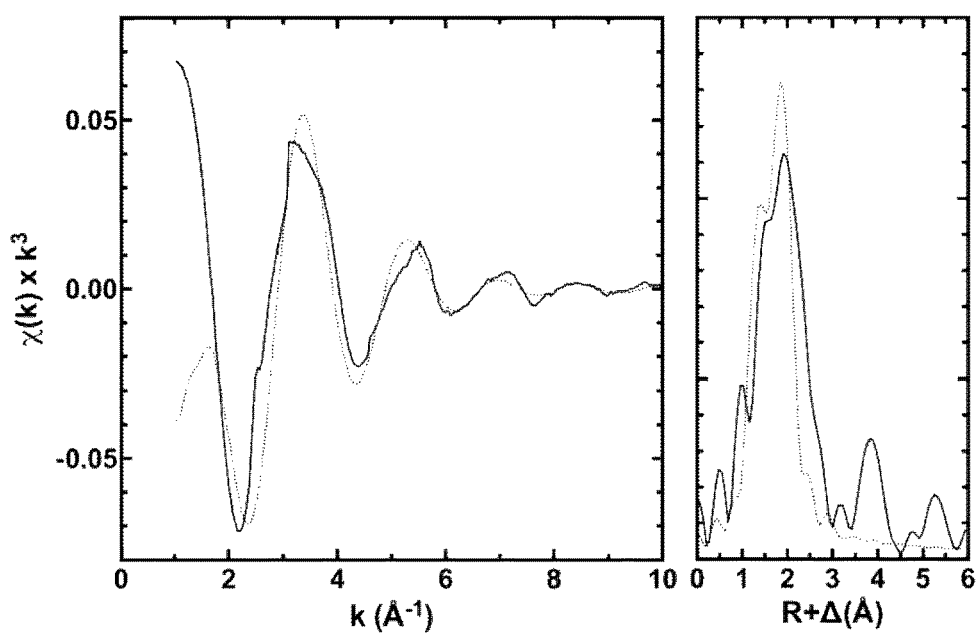
Figure 37:
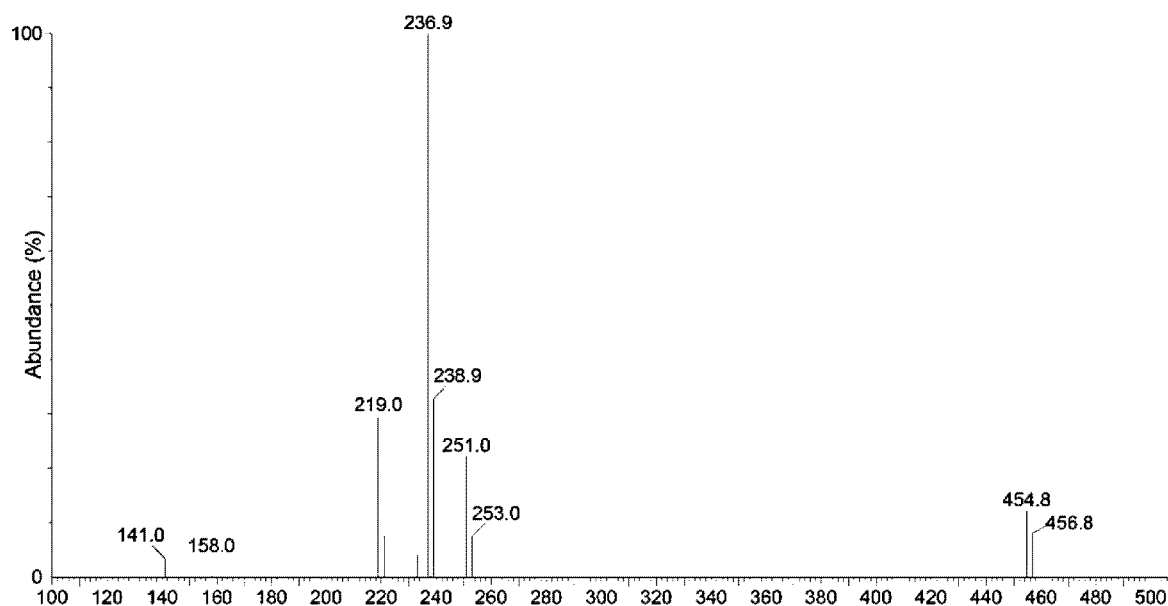
Figure 38:
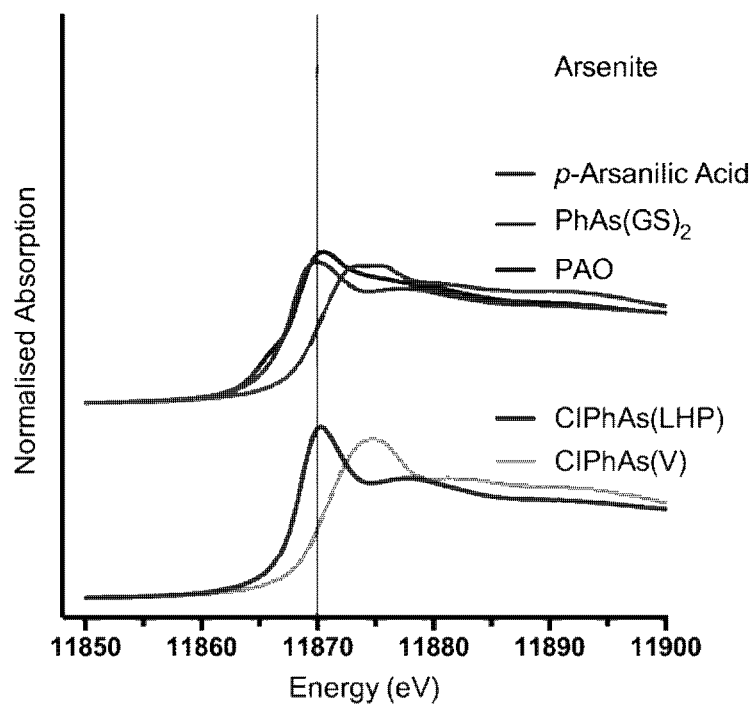
Figure 39:
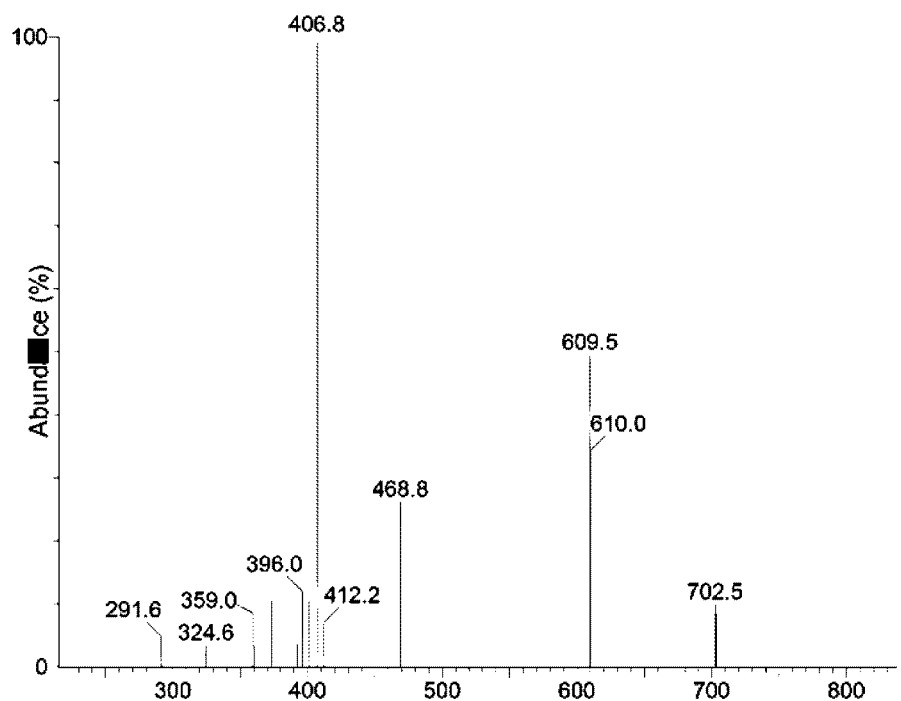
Figure 40:
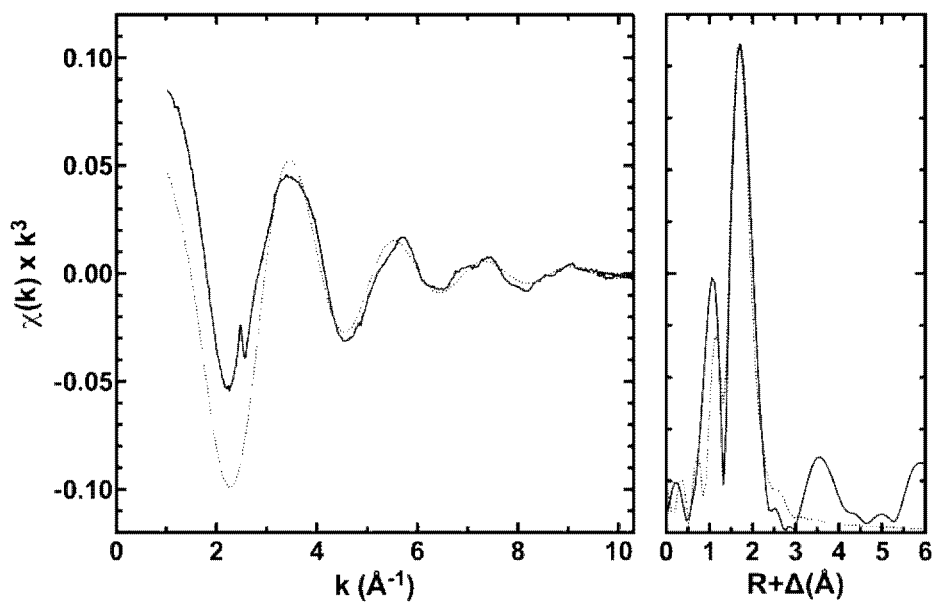
Figure 41:
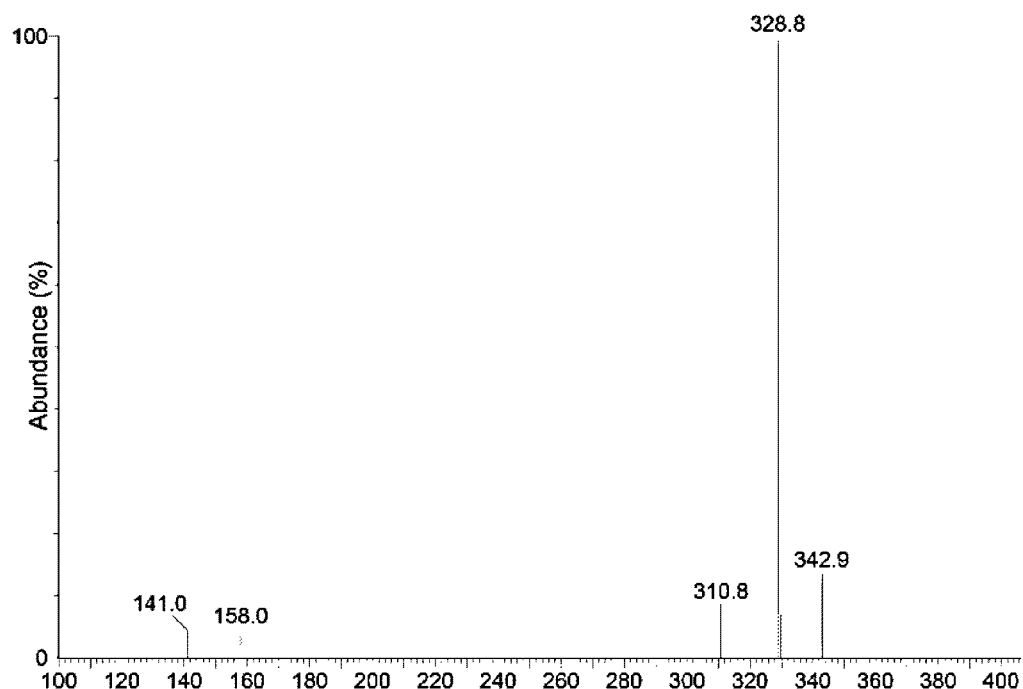
Figure 42:
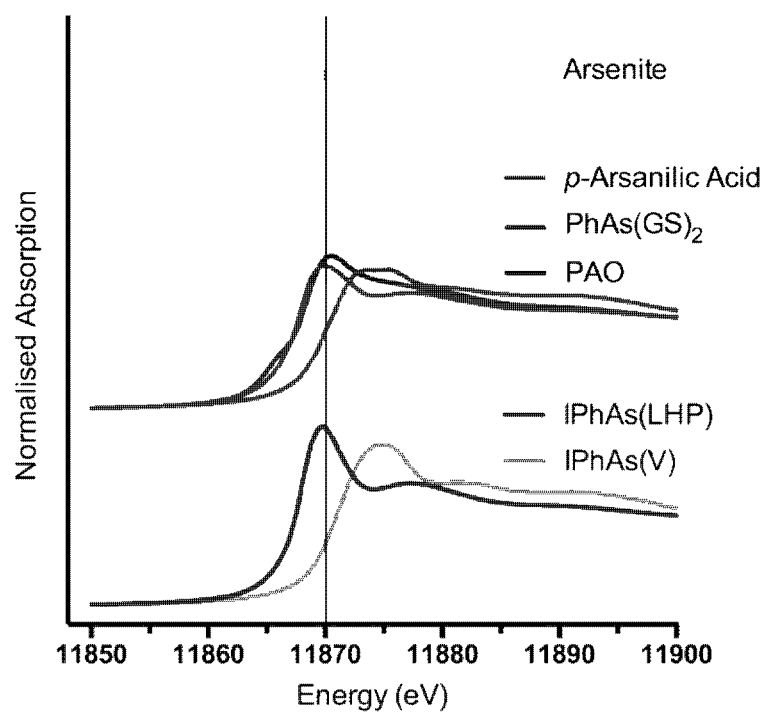
Figure 43:
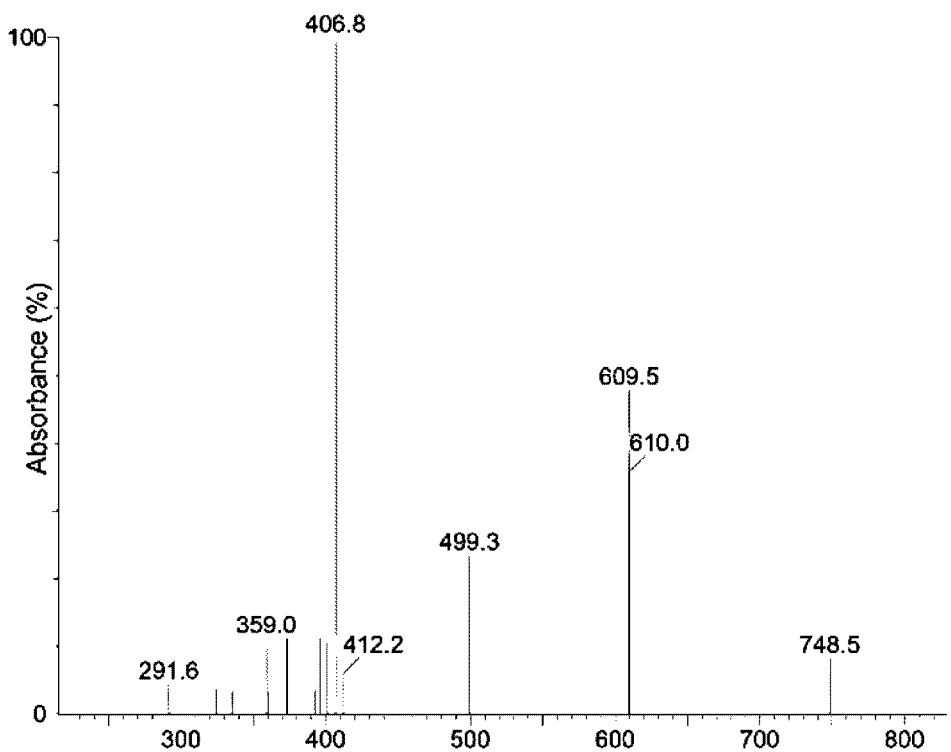
Figure 44:
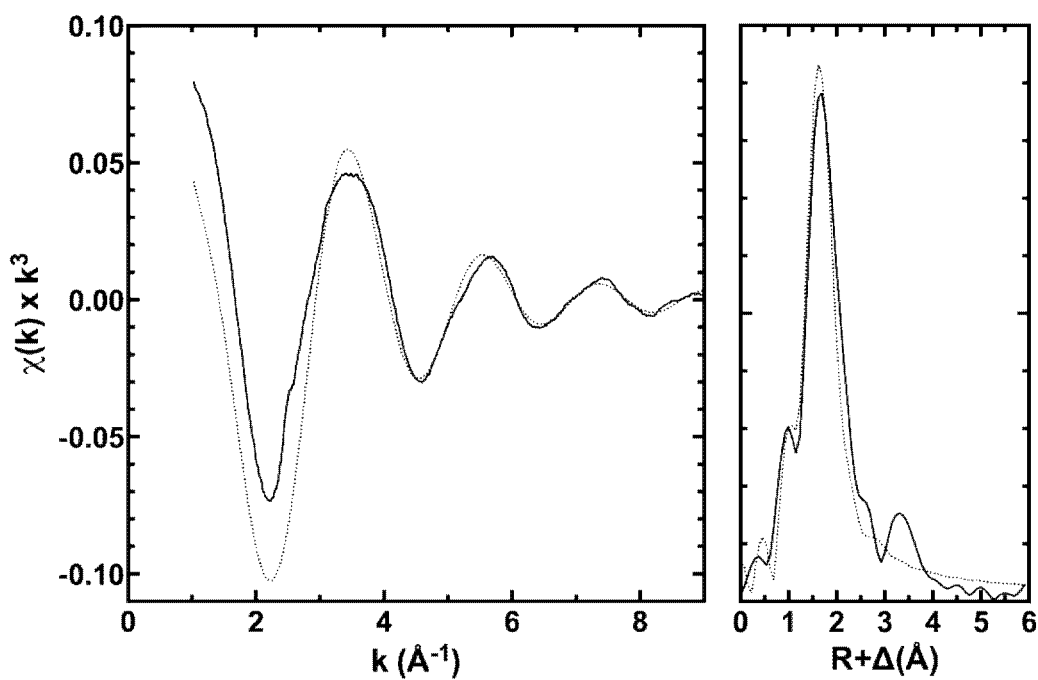

FIG. 29 shows toluidine-blue stained thin sections of K562 cells that have been exposed to PhAs(LHP) (10 µM, 24 h) (a) Correlative light micrograph image (b) the corresponding microprobe SR-XRF maps of P, Zn and As, and the colocalisation map of the three elements. This shows localisation of As in the cell nucleus following PhAs(LHP) treatment;

FIG. 30 is a series of micrograph images of toluidine-blue-stained, thin-sectioned control and PhAs(LHP)-treated HL-60 cells. (a) HL-60 control cells (b) PhAs(LHP)-treated HL-60 cells (10 µM, 4 h) (c) PhAs(LHP)-treated HL-60 cells (10 µM, 24 h), showing the stress and cell demise following PhAs(LHP) treatment;

FIG. 31 is the micrograph images and the correlating microprobe SR-XRF elemental maps for thin-sectioned, toluidine blue stained control and PhAs(LHP)-treated HL-60 cells. (a) HL-60 control cells (b) PhAs(LHP)-treated HL-60 cells (10 µM, 4 h) (c) PhAs(LHP)-treated HL-60 cells (10 µM, 24 h). Operating conditions include: beam energy=11.9 key; beam size=0.3×0.3 µm$^2$; step size=0.3 µm; dwell time=2.5 s/pt; and scan dimensions (H×V)=(a) 15×11 µm$^2$; (b) 13×14 µm$^2$; (c) 16×14 µm$^2$. This shows increased As uptake between 4-24 h treatment with significant accumulation in the nucleus;

FIG. 32 is the toluidine-blue stained thin section of HL-60 cells that have been exposed to PhAs(LHP) (10 µM, 24 h) (a) Correlative light micrograph image (b) the corresponding microprobe SR-XRF maps of P, Zn and As, and the colocalisation map of the three elements. This shows significant As accumulation in the nucleus following treatment with PhAs(LHP);

FIG. 33 is the positive ion ESI mass spectrum (m/z 160-400) of the synthesised NH$_2$PhAs(III) dissolved in MilliQ water showing peaks: m/z 184.0, [NH$_2$-Ph-As=O+H]$^+$; m/z 202.0, [NH$_2$-Ph-As—(OH)$_2$+H]$^+$; m/z 220.0, unidentified; m/z 259.0, [NH$_2$-Ph-As-Cl$_2$+Na]$^+$; m/z 279.1, [P(Ph)$_3$O+H]$^+$, confirming production of NH$_2$PhAs(III);

FIG. 34 is the As K edge XANES spectra of solid standards and the synthesised NH$_2$PhAs(LHP) and NH$_2$PhAs(III). The spectra include the data acquired for arsenite, p-arsanilic acid, PhAs(GS)$_2$, PAO and NH$_2$PhAs (LHP), indicating that the As in NH$_2$PhAs(LHP) is As(III) and likely bound to S;

FIG. 35 is the positive ion ESI mass spectrum (m/z 240-1500) of products obtained from the reaction of the synthesised p-aminophenyldichloroarsine/p-aminophenylarsine oxide (3 mM) and LHP (1 mM) in MilliQ water at 37° C. after 16 hours showing peaks: m/z 259.1, [NH$_2$-Ph-As-Cl$_2$+Na]$^+$; m/z 407.2, [LHP+3H]$^{3+}$; m/z 462.4, [NH$_2$-Ph-As(LHP)+3H]$^{3+}$; m/z 610.1, [LHP+2H]$^{2+}$; m/z 693.0, [NH$_2$-Ph-As(LHP)+2H]$^{2+}$, confirming production of NH$_2$PhAs(LHP);

FIG. 36 is an EXAFS analysis (left) and corresponding Fourier Transforms (right) of NH$_2$PhAs(LHP) showing experimental (—) and calculated (---) data using a single-scattering fit (the first coordination shell). This confirms As is bound to 2S and 1C;

FIG. 37 is the positive ion ESI mass spectrum (m/z 160-600) of the synthesised p-chlorophenylarsonic acid dissolved in methanol showing peaks: m/z 219.0, [OH-Ph-AsH$_2$O$_3$+H]$^+$; m/z 236.9, [Cl-Ph-AsH$_2$O$_3$+H]$^+$; m/z 141.0, contaminant; m/z 158.0, contaminant, confirming the production of Cl-Ph-AsH$_2$O$_3$;

FIG. 38 is the As K-edge XANES spectra of solid standards and the synthesised ClPhAs(LHP) (first trace to rise to a peak on lower series of traces) and ClPhAs(V). The standards include: arsenite, p-arsanilic acid (later trace to rise in middle series of traces), PhAs(GS)$_2$ and PAO. This indicates that the As in ClPhAs(LHP) is As(III) and likely bound to S;

FIG. 39 is the positive ion ESI mass spectrum (m/z 240-1400) of products obtained from the reaction of ClPhAs (V) (1 mM) with LHP (3 mM) in MilliQ water at 37° C. for 72 h showing peaks: m/z 406.8, [oxidised LHP+3H]$^{3+}$, m/z 468.8, [Cl-Ph-As(LHP)+3H]$^{3+}$; m/z 609.5, [oxidised LHP+2H]$^{2+}$; m/z 702.5, [Cl-Ph-As(LHP)+2H]$^{2+}$, confirming production of ClPhAs(LHP);

FIG. 40 is an EXAFS analysis (left) and corresponding Fourier transform (right) of the first ClPhAs(LHP) fraction obtained from preparative HPLC showing experimental (—) and calculated (---) data using a single-scattering fit (the first coordination shell). This confirms As is bound to 2S and 1C;

FIG. 41 is the positive ion ESI mass spectrum (m/z 100-600) of the synthesised p-iodophenylarsonic acid dissolved in methanol. Peaks were assigned as: m/z 328.8, [I-Ph-AsH$_2$O$_3$+H]+; m/z 141.0, contaminant; m/z 158.0, contaminant. This confirms production of IPhAsH$_2$O$_3$;

FIG. 42 is the As K-edge XANES spectra of solid standards and the synthesised IPhAs(LHP) (first trace of lower pair of traces to rise to a peak) and IPhAs(V). The standards include: arsenite, p-arsanilic acid (later of middle series of traces to rise to a peak), PhAs(GS)$_2$ and PAO. This indicates that the As in IPhAs(LHP) is As(III) and likely bound to S;

FIG. 43 is the positive ion ESI mass spectrum (m/z 240-1400) of products obtained from the reaction of the synthesised p-iodophenylarsonic acid (1 mM) and LHP (3 mM) in MilliQ water at 37° C. after 72 h. Peaks: m/z 406.8, [oxidised LHP+3H]$^{3+}$; m/z 499.3, [I-Ph-As(LHP)+3H]$^{3+}$; m/z 609.5, [oxidised LHP+2H]$^{2+}$; m/z 748.5, [I-Ph-As(LHP)+2H]$^{2+}$, confirming production of IPhAs(LHP); and FIG. 44 is an EXAFS analysis (left) and corresponding Fourier Transforms (right) of the first IPhAs(LHP) fraction obtained from preparative HPLC showing experimental (—) and calculated (---) data using a single-scattering fit (the first coordination shell). This confirms As is bound to 2S and 1C.

DETAILED DESCRIPTION

The present invention is predicated, at least in part, on the realisation that an arsenic atom could be stably attached to a tumour homing peptide having, or having been modified to present, two cysteine residues, preferably a tumour homing peptide having N- and C-terminal cysteine residues, such that the tumour homing peptide cyclises to give a highly selective arsenic-containing anti-cancer agent. This allows for selection of an appropriate tumour homing peptide for treatment of a given cancer whereby the subsequent agent provides for a more targeted delivery of arsenic to the tumour microenvironment.

Surprisingly, once the tumour homing peptide is attached to the arsenic, the arsenic-containing anti-cancer agent is quite stable such that it can be formulated and delivered, in a highly specific and selective manner, to a tumour site. At the same time the arsenic atom is biologically available to exert its damaging effect on the tumour cells. Such an outcome could not have been predicted given the size of the tumour homing peptide relative to the bound arsenic and also the strength of bonding of the cysteine thiol groups to the arsenic. This provides for an opportunity to deliver arsenic in an efficient and efficacious manner within an agent that is highly selective for cancer types. Due to the ability to select the tumour homing peptide a wide variety of cancers can be targeted in this selective manner.

Definitions

Referring now to terminology used generically herein, the term "alkyl" means a straight-chain or branched alkyl substituent containing from, for example, 1 to about 6 carbon atoms, preferably from 1 to about 4 carbon atoms, still yet more preferably from 1 to 2 carbon atoms. Examples of such substituents considered to be included within these ranges include methyl, ethyl, propyl, isopropyl, n-butyl, sec-butyl, isobutyl, tert-butyl, pentyl, isoamyl, hexyl, and the like. The number of carbons referred to relates to the carbon backbone and carbon branching but does not include carbon atoms belonging to any substituents, for example the carbon atoms of an alkoxy substituent branching off the main carbon chain.

The term "alkenyl," as used herein, means a linear alkenyl substituent containing at least one carbon-carbon double bond and from, for example, 2 to 6 carbon atoms (branched alkenyls are 3 to 6 carbons atoms), preferably from 2 to 5 carbon atoms (branched alkenyls are preferably from 3 to 5 carbon atoms), more preferably from 2 to 4 carbon atoms. Examples of such substituents considered to be included within these ranges include vinyl, propenyl, isopropenyl, n-butenyl, sec-butenyl, isobutenyl, tert-butenyl, pentenyl, isopentenyl, hexenyl, and the like.

The term "alkynyl," as used herein, means a linear alkynyl substituent containing at least one carbon-carbon triple bond and from, for example, 2 to 6 carbon atoms (branched alkynyls are 3 to 6 carbons atoms), preferably from 2 to 5 carbon atoms (branched alkynyls are preferably from 3 to 5 carbon atoms), more preferably from 2 to 4 carbon atoms. Examples of such substituents considered to be included within these ranges include ethynyl, propynyl, isopropynyl, n-butynyl, sec-butynyl, isobutynyl, tert-butynyl, pentynyl, isopentynyl, hexynyl, and the like.

The term "cycloalkyl" refers to optionally substituted saturated mono-cyclic, bicyclic or tricyclic carbon groups. Where appropriate, the cycloalkyl group may have a specified number of carbon atoms, for example, $C_3$-$C_6$ cycloalkyl is a carbocyclic group having 3, 4, 5 or 6 carbon atoms. Non-limiting examples may include cyclopropyl, cyclobutyl, cyclopentyl, cyclohexyl, and the like.

The term "aryl" refers to an unsubstituted or substituted aromatic carbocyclic substituent, as commonly understood in the art. It is understood that the term aryl applies to cyclic substituents that are planar and comprise $4n+2\pi$ electrons, according to Hückel's Rule. Phenyl, which may be substituted or unsubstituted, is a preferred aryl group as the stabilising group attached to the arsenic atom.

"Heterocyclic" or "heterocycle" refers to an aromatic or non-aromatic ring preferably having 5 to 7 atoms in the ring and of those atoms 1 to 4 are heteroatoms, said ring being isolated or fused to a second ring wherein said heteroatoms are independently selected from O, N and S. Heterocyclic includes partially and fully saturated heterocyclic groups. Heterocyclic systems may be attached to another moiety via any number of carbon atoms or heteroatoms of the radical and may be both saturated and unsaturated. Heterocyclic rings include nitrogen heterocycles. Non-limiting examples of heterocyclic include indoline, pyrrolidinyl, pyrrolinyl, pyranyl, piperidinyl, piperazinyl, morpholinyl, tetrahydrofuranyl, tetrahydrothiophenyl, pyrazolinyl, dithiolyl, oxathiolyl, dioxanyl, dioxinyl, oxazinyl, azepinyl, diazepinyl, thiazepinyl, oxepinyl and thiapinyl, imidazolinyl, thiomorpholinyl, and the like.

In any of the embodiments described the term "substituted" (such as is referred to herein as 'substituted or unsubstituted') or "optionally substituted" and the like) may refer to substitution of that moiety with a group selected from the group consisting of $C_1$-$C_6$ alkyl, aryl (including phenyl which may itself be substituted with methyl, ethyl, propyl, halo, nitro, $C_1$-$C_6$ alkoxy, and glutathiyl), cycloalkyl, carboxyl, glutathiyl, halo, nitro, and haloalkyl. Each of these groups may themselves be substituted with the same or different groups.

The term "tumour homing peptide", as used herein, refers to relatively short peptides having the ability to recognize and bind to, optionally and/or be uptaken into, tumour cells or tissues, tumour blood vessels, lymphatic vessels and other tumour associated microenvironments. They may also be referred to in the art as "tumour-specific internalizing peptides" and "tumour penetrating peptides". The nature of the tumour homing peptide is not especially limited although they must present at least two cysteine residues which are capable of bonding to the one arsenic atom or be able to be adapted to present two such cysteine residues. A wide range of such peptides are commercially available and can, in fact, be made to order.

As generally used herein, the terms "administering" or "administration", and the like, describe the introduction of the anti-cancer agent or composition to a mammal such as by a particular route or vehicle. Routes of administration may include topical, parenteral and enteral which include oral, buccal, sub-lingual, nasal, anal, gastrointestinal, subcutaneous, intravenous, intramuscular and intradermal routes of administration, although without limitation thereto.

By "treat", "treatment" or "treating" is meant administration of the anti-cancer agent or composition to a subject to at least ameliorate, reduce or suppress existing signs or symptoms of the disease, disorder or condition, such as a cancer, experienced by the subject.

As used herein, "effective amount" refers to the administration of an amount of the relevant anti-cancer agent or composition sufficient to prevent the occurrence of symptoms of the condition being treated, or to bring about a halt in the worsening of symptoms or to treat and alleviate or at least reduce the severity of the symptoms. The effective amount will vary in a manner which would be understood by a person of skill in the art with patient age, sex, weight etc. An appropriate dosage or dosage regime can be ascertained through routine trial.

Anti-Cancer Agent

In one form, there is provided an anti-cancer agent comprising a cyclised tumour homing peptide having an arsenic atom bonded to two cysteine residues.

Suitably, the arsenic atom bonded to the two cysteine residues allows the tumour homing peptide to be cyclic. That is, the arsenic is bonded to a sulfur of each cysteine thereby forming a cyclic peptide structure having an arsenic bridge. It is believed that the interaction of the arsenic with the dithiol (one thiol of each cysteine) results in a more stable anti-cancer agent than can be achieved with monothiol-arsenic bonding.

Naturally occurring arsenic-peptide species have proven difficult to isolate and purify due to the instability of these complexes during the typical purification and characterisation processes. This has greatly limited the therapeutic uses of arsenic-peptide complexes. The present anti-cancer agents therefore provide significant advantages in that they can be purified, characterised and stored while still maintaining efficacy.

In one embodiment, the two arsenic-bonded cysteine residues of the tumour homing peptide are separated from one another by less than 20 amino acid residues.

In certain embodiments, the two arsenic-bonded cysteine residues of the tumour homing peptide are separated by less than 18 amino acid residues, or less than 16 amino acid residues, or less than 15 amino acid residues, or less than 14 amino acid residues. Any of these upper values may be coupled with a lower end range of one or two amino acid residues.

It has been found that the number of amino acids between the cysteine residues is important in predicting whether or not the peptide will cyclise and form the arsenic bridge. Preferred ranges of amino acid residues between the cysteines which will bond to the arsenic may be selected from between 2 to 15 residues, 3 to 15 residues, 4 to 15 residues, 5 to 15 residues, 2 to 14 residues, 3 to 14 residues, 4 to 14 residues, and 5 to 14 residues.

In embodiments, prior to cyclisation, the two cysteine residues which bind the arsenic atom form the respective N-terminal and C-terminal peptide residues of the tumour homing peptide. It is preferred that each terminal amino acid of the tumour homing peptide is a cysteine as this improves the cyclisation and promotes arsenic bridging between respective cysteine thiols. Formation of the cyclised peptide is a critical step as, in the majority of cases, it is the cyclised conformation of the peptide which is recognised by the relevant receptor.

The N-terminal cysteine may comprise a capping group bonded to its free amino nitrogen. Without wishing to be bound by any particular theory it is believed that the capping group essentially acts to prevent cyclisation and/or polymerisation of the tumour homing peptide prior to insertion of the arsenic atom or at least limits association of the N- and C-terminal residues to better promote arsenic bonding. The capping group may therefore be important to efficient arsenic uptake and binding. The capping group may be formed from any N-terminus capping compound capable of reacting with the amino nitrogen and forming a relatively unreactive/stable capping group.

Therefore, in one embodiment, the capping group is an amino-reactive group. Any compound presenting a carboxylic acid for reaction with the cysteine amino group may be suitable. It is preferred that such a compound presenting a carboxylic acid also has an unreactive moiety. In preferred embodiments, the capping group is an alkanoyl group, such as a $C_2$-$C_6$ alkanoyl group which may be optionally substituted. Specific examples of appropriate capping agents of various classes may include acetyl, pyroglutamic acid, indoles, benzimidazoles, benzimidazolones, Fmoc and the like. Smaller inert capping groups are preferred and so, in one preferred embodiment, the capping group is an acetyl group. It will be appreciated by the person of skill in the art that such N-terminus capping groups are known in the art, as are the means of locating them in the desired position on the tumour homing peptide.

In an embodiment, the anti-cancer agent further comprises a stabilising group bonded to the arsenic atom. The stabilising group will typically already be bound to the arsenic atom in the arsenic compound which is used to contact the tumour homing peptide. It has been found that the choice of stabilising group can have a significant positive effect on the stability of the anti-cancer agent and therefore its ongoing efficacy in methods of treatment.

Suitably, the stabilising group is selected from the group consisting of hydroxyl, $C_1$ to $C_6$ alkyl, $C_2$ to $C_6$ alkenyl, $C_2$ to $C_6$ alkynyl, $C_1$ to $C_6$ alkoxy, aryl, cycloalkyl, heterocyclic, and short chain peptides including glutathiyl, each of which groups may be substituted or unsubstituted.

In one embodiment the stabilising group is selected from the group consisting of hydroxyl, $C_1$ to $C_4$ alkyl, $C_2$ to $C_4$ alkenyl, $C_1$ to $C_4$ alkoxy, $C_5$ or $C_6$ aryl, $C_5$ or $C_6$ cycloalkyl, $C_6$ or $C_6$ heterocyclic, and glutathiyl, each of which groups may be substituted or unsubstituted.

In certain embodiments, the stabilising group is selected from the group consisting of hydroxyl, methyl, ethyl, propyl, isopropyl, n-butyl, sec-butyl, isobutyl, tert-butyl, and substituted or unsubstituted phenyl.

When the stabilising group is substituted phenyl then the substitution may be with hydroxyl, $C_1$ to $C_4$ alkyl, $C_1$ to $C_4$ alkoxy, glutathiyl, arginine, lysine, halo, $C_1$ to $C_4$ haloalkyl, nitro, amino, secondary or tertiary amine, amido, ether and ester.

Preferred substitutions include amino (i.e. $NH_2$), hydroxyl, methoxy, ethoxy, fluoro, chloro and iodo.

The substitution on the phenyl group may be ortho, meta or para to the point of attachment of the arsenic atom. Preferably the substitution is a single substitution para to the arsenic atom.

In embodiments, the tumour homing peptide comprises at least one arginine and/or lysine residue. Arginine and lysine may be preferred as such positively charged amino acids may interact with the negatively charged cell surface proteins to improve internalisation of the tumour homing peptide.

Certain of the anti-cancer agents of the first aspect may contain chiral centers, which may be either of the (R) or (S) configuration, or, when used, may be administered as a mixture thereof. Accordingly, the present invention also includes stereoisomers of the agents described herein, where applicable, either individually or admixed in any proportions. Such stereoisomers can be separated using conventional techniques, as described in the examples, such as HPLC.

Particularly, the arsenic atom may be a chiral centre and the cyclic peptide attached thereto may result in the formation of R and S isomers. The structures herein are considered to explicitly cover both R and S isomers. It has been found that the enantiomers may form spontaneously during synthesis and can be used as a racemic mixture. It will be appreciated, however, that in some embodiments it may be desirable to either separate and use the enantiomerically pure form or to at least enrich a composition with one isomer.

In one embodiment, the anti-cancer agent has a structure as shown in formula I:

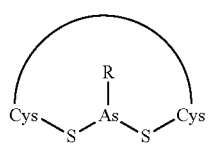

formula I wherein, the sulfur atoms shown, to which the arsenic is bonded, are the thiol sulfurs of the respective cysteine residues;

the cysteine residues in formula I are separated by less than 20 amino acid residues represented by the curved line; and R is a stabilising group comprising moieties selected from the group consisting of hydroxyl, $C_1$ to $C_6$ alkyl, $C_2$ to $C_6$ alkenyl, $C_2$ to $C_6$ alkynyl, $C_1$ to $C_6$ alkoxy, aryl, cycloalkyl, heterocyclic, and short chain peptides including glutathiyl, each of which groups may be substituted or unsubstituted.

The stabilising group, 'IR', may comprise or be selected from those stabilising groups described previously.

Appropriate short chain peptides for 'IR' may be or comprise those having between four to twenty, preferably four to sixteen or four to ten amino acid residues.

The amino acid chain joining the two cysteine residues may be as previously described in terms of amino acid residue length. The N-terminus cysteine may also have a capping group as previously described.

Therefore, in one embodiment, the anti-cancer agent of formula I may have a structure as shown in formula II:

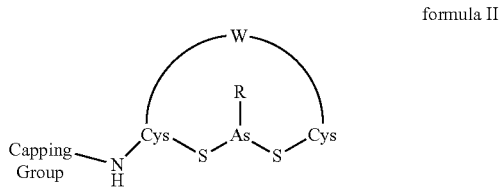

formula II wherein, the various atoms and groups are as described for formula I;
the capping group is formed from an amino reactive compound; and
W is between 2 to 20 amino acid residues.

It will be appreciated that the '—NH' group between the capping group and cystein residue may be the —NH which is part of the cystein residue itself. That is, the —NH may be the standard cysteine —$NH_2$ moiety to which the capping group has been bound to form '—NH-Capping Group'.

The number of amino acid residues represented by 'W' may be selected from any of those values previously discussed including less than 18 amino acid residues, or less than 16 amino acid residues, or less than 15 amino acid residues, or less than 14 amino acid residues. Any of these upper values may be coupled with a lower end range of two amino acid residues.

It will be appreciated that while the structures of formula I and II may be preferred, they are not the only structures considered appropriate for use in the present invention. Particularly, it is not required that the peptide has terminal cysteine residues but merely that two such amino acids are present and that they are separated by a sufficient number of residues to allow for cyclisation with the arsenic atom.

In one embodiment, the tumour homing peptide to which the arsenic atom will be bonded between two cysteine residues to form a bridge, may be selected from the group consisting of:
1. CAYHRLRRC;
2. CDCRGDCFC;
3. CPIEDRPMC;
4. CNRRTKAGC;
5. CGTKRKC;
6. CRGDGWC;
7. CVSNPRWKC;
8. CHVLWSTRC;
9. CLDGGRPKC;
10. GCSVSSVGALCTHV;
11. CRGDGWC;
12. CDCRGDCFC;
13. CVNHPAFAC;
14. CRGDRGPDC;
15. CRGDKTTNC;
16. CRGDHAGDC;
17. CLSYYPSYC;
18. CTPSPPFSHC;
19. CPHSKPCLC;
20. CSDSWHYWC;
21. CSDWQHPWC;
22. CSDYNHHWC;
23. CSDGQHYWC;
24. CYDSWHYWC;
25. CFDGNHIWC;
26. CTDFPRSFC;
27. CTQDRQHPC;
28. CLSRYLDQC;
29. CRGDCF;
30. CGNSNPKSC; and
31. CPHNLTKLC wherein the arsenic atom, when in the formed anti-cancer agent of the first aspect, will be bonded to and bridge between two of the cysteine residues of the above peptide sequences. One or both of the cysteine residues may be, but are not necessarily, a terminal residue.

Collectively, these tumour homing peptides may target a selection of cancers including but not limited to the following: leukemia/lymphomas, colon cancer, esophagus and gastroesophageal cancer, epidermal squamous cell cancers, melanoma, pancreatic islet tumours, breast carcinoma, prostate cancer, lung cancer, colorectal cancer, retinoblastoma, tumour metastasis, hepatic cancer, pancreatic cancer, brain cancer, mesothelioma, melanoma, ovarian and gastric cancer.

It will be appreciated that other such tumour homing peptides are commercially available for alternative cancer targets and can often be designed 'to order' for a specified target. In this respect, the tumour homing peptide component of the anti-cancer agent is not particularly limited and will be chosen from known peptides based on the desired cancer to be targeted.

In one preferred embodiment, the tumour homing peptide to which the arsenic atom will be bonded to form a bridge, is CAYHRLRRC (Motif: CAY); CDCRGDCFC (Motif: RGD) or CPIEDRPMC. These peptides are useful for targeting leukemia and lymphoma cells, angiogenic vasculature and colon cancer, respectively, and can therefore be cyclised with an arsenic atom, as previously described, to form anti-cancer agents effective against these targets.

In one embodiment, the arsenic of the anti-cancer agent is an arsenic(III) atom.

In one particularly preferred embodiment, the anti-cancer agent of the first aspect has the structure below:

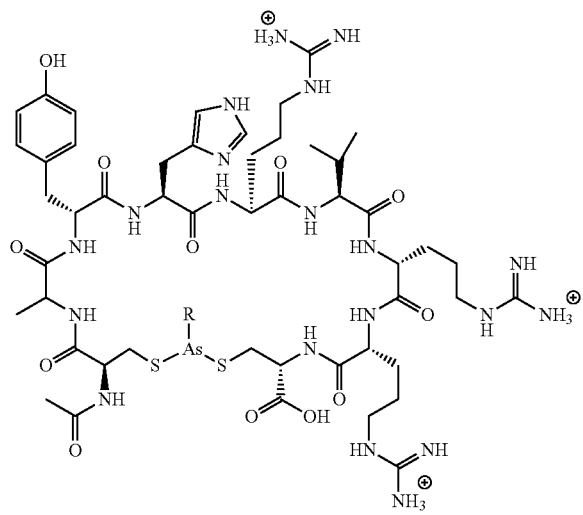

wherein R is a stabilising group selected from hydroxyl, methyl and substituted or unsubstituted phenyl.

In the experimental section which follows, references to HyAs(LHP), MeAs(LHP) and PhAs(LHP) are references to the above structure wherein R is hydroxyl, methyl and unsubstituted phenyl, respectively.

According to a second aspect of the invention, there is provided a pharmaceutical composition comprising an anti-cancer agent of the first aspect and a pharmaceutically acceptable carrier, diluent and/or excipient.

Suitably, the pharmaceutically acceptable carrier, diluent and/or excipient may be or include one or more of diluents, solvents, pH buffers, binders, fillers, emulsifiers, disintegrants, polymers, lubricants, oils, fats, waxes, coatings, viscosity-modifying agents, glidants and the like.

Diluents may include one or more of microcrystalline cellulose, lactose, mannitol, calcium phosphate, calcium sulfate, kaolin, dry starch, powdered sugar, and the Ike. Binders may include one or more of povidone, starch, stearic add, gums, hydroxypropylmethyl cellulose and the like. Disintegrants may include one or more of starch, croscarmellose sodium, crospovidone, sodium starch glycolate and the like. Solvents may include one or more of ethanol, methanol, isopropanol, chloroform, acetone, methylethyl ketone, methylene chloride, water, saline solutions and the like. Lubricants may include one or more of magnesium stearate, zinc stearate, calcium stearate, stearic acid, sodium stearyl fumarate, hydrogenated vegetable oil, glyceryl behenate and the like. A glidant may be one or more of colloidal silicon dioxide, talc or cornstarch and the like. Buffers may include phosphate buffers, borate buffers and carbonate buffers, although without limitation thereto. Fillers may include one or more gels inclusive of gelatin, starch and synthetic polymer gels, although without limitation thereto. Coatings may comprise one or more of film formers, solvents, plasticizers and the like. Suitable film formers may be one or more of hydroxypropyl methyl cellulose, methyl hydroxyethyl cellulose, ethyl cellulose, hydroxypropyl cellulose, povidone, sodium carboxymethyl cellulose, polyethylene glycol, acrylates and the like. Suitable solvents may be one or more of water, ethanol, methanol, isopropanol, chloroform, acetone, methylethyl ketone, methylene chloride and the like, Plasticizers may be one or more of propylene glycol, castor oil, glycerin, polyethylene glycol, polysorbates, and the like.

Reference is made to the Handbook of Excipients 6th Edition, Eds. Rowe, Sheskey & Quinn (Pharmaceutical Press), which provides non-limiting examples of excipients which may be useful according to the invention.

It will be appreciated that the choice of pharmaceutically acceptable carriers, diluents and/or excipients will, at least in part, be dependent upon the mode of administration of the formulation. By way of example only, the composition may be in the form of a solution for IV administration, an injectable liquid, a suppository, a slow release formulation, an osmotic pump formulation or any other form that is effective and safe for administration. A saline solution for IV administration is particularly preferred due to an advantageous solubility profile.

According to a third aspect of the invention there is provided a method of treating a cancer in a patient including the step of administering an anti-cancer agent of the first aspect or the pharmaceutical composition of the second aspect to the patient to thereby treat the cancer.

A fourth aspect of the invention resides in an anti-cancer agent of the first aspect for use in treating a cancer in a patient.

A fifth aspect of the invention resides in the use of an anti-cancer agent of the first aspect in the manufacture of a medicament for the treatment of a cancer.

In relation to the third to fifth aspects, in one embodiment the cancer may be a haematological malignancy or a solid tumour.

In a further embodiment the cancer is selected from a leukemia, multiple myeloma, and a lymphoma.

The cancer may be selected from the group consisting of squamous cell carcinoma, basal cell carcinoma, melanoma, tumours of the epithelial lining of glands or ducts, adenocarcinoma, papillary carcinoma, papillary adenocarcinoma tumours of the liver and biliary tract, hepatocellular carcinoma tumours of the gastrointestinal tract, squamous cell carcinoma of the oesophagus, adenocarcinoma of the oesophagus, colorectal carcinoma (colon cancer), gastric carcinoma (stomach cancer) tumours of the respiratory tract, bronchogenic carcinoma, small cell carcinoma, large cell carcinoma tumours of the urogenital tract, transitional cell carcinomas of the bladder, squamous cell carcinoma of the bladder, carcinoma of the prostate, carcinoma of the cervix, blood cells and related cells (leukemias), acute and chronic lymphocytic leukemia, polycythemia vera, cancers of lymphoid tissue, malignant lymphomas including Hodgkin's lymphoma and non-Hodgkin's lymphoma, follicular lymphoma, diffuse lymphoma, small lymphocytic lymphoma, large cell lymphoma, lymphoblastic lymphoma, multiple myeloma, tumours of connective tissue, cancers of bone osteosarcoma, tumours of the nervous system, neuroblastoma, retinoblastoma, glioblastoma, oligodendroglioma tumours associated with oncogenic viruses, Burkitts lymphoma, b cell lymphoma's in immuno-comprised individuals, nasopharyngeal carcinoma, esophagus and gastroesophageal cancers, epidermal squamous cell cancers, pancreatic islet tumours, breast carcinoma, ovarian cancer, lung cancer, colorectal cancer, retinoblastoma, hepatic cancer, pancreatic cancer, brain cancer, mesothelioma and hepatitis b virus hepatocellular carcinoma.

When the cancer is leukemia it may be a form selected from the group consisting of acute lymphoblastic leukemia (ALL), acute lymphoblastic B-cell leukemia, acute lymphoblastic T-cell leukemia, acute myeloblastic leukemia (AML), acute promyelocytic leukemia (APL), acute monoblastic leukemia, acute erythroleukemic leukemia, acute megakaryoblastic leukemia, acute myelomonocytic leukemia, acute undifferentiated leukemia, chronic myelocytic leukemia and chronic lymphocytic leukemia.

Preferably, the cancer is selected from the group consisting of chronic myeloid leukemia, t-cell lymphoma, myelodysplastic syndrome, colon cancer, pancreatic cancer, brain cancer, mesothelioma, acute promyelocytic leukemia (APL) and acute myeloid leukemia (AML).

The treatment of acute myeloid leukemia may, in embodiments, be highly preferred as this is a cancer which is known to be difficult to treat. Results provided herein, particularly in relation to Kasumi-1 cells, indicate that the anti-cancer agent of the first aspect can be highly effective against AML.

When the cancer is a solid tumour it may be one or more of a cancer of the digestive tract, oesophagus, liver, stomach, colon, skin, brain, bone, breast, lung, mesothelium and soft tissues, including but not limited to various sarcomas and prostate cancer.

In one embodiment, the cancer may be any cancer which is currently indicated for treatment by clinically available arsenic trioxide solutions or against which solutions of arsenic trioxide have been shown to demonstrate efficacy. In one embodiment, the lymphoma, leukemia or solid tumour in the patient is refractory to standard methods of treatment, or is a relapsed case of leukemia.

The anti-cancer agent may be used alone or in combination with other known therapeutic agents such as, for example, immunotherapeutics, monoclonal antibodies, chemotherapeutics, radioprotectants and radiotherapeutics. Particularly, the delivery of the anti-cancer agent may occur before, during or after the administration of one or more known anti-tumour agents including but not limited to hypomethylating agents, PD-1 inhibitors, PD-L1 inhibitors, mustard compounds, nitrogen mustard, chlorambucil, melphalan, cyclophosphamide, 6-mercaptopurine, 6-thioguanine, cytarabine, 5-fluorouracil, floxuridine, methotrexate, vincristine, vinblastine, taxol, etoposide, temiposide, dactinomycin, daunorubicin, doxorubicin, bleomycin, mitomycin, cisplatin, carboplatin, estramustine phosphate, hydroxyurea, BCNU, procarbazine, VM-26, interferons, and all-trans retinoic acid (ATRA), or other retinoids. Suitable hypomethylating agents may include decitabine, guancitabine, azacitidine and the like. Suitable examples of PD-1 inhibitors include pembrolizumab and nivolumab while appropriate PD-L1 inhibitors include atezolizumab, avelumab and durvalumab.

The therapeutic dose and dosing frequency of the anti-cancer agent in the treatment of various cancers will depend on the nature of the cancer, the severity of the condition as well as age, body weight, condition and response of the individual patient. Importantly, such dosing can conveniently be decided upon based on standard processes and following the guidelines of current dosing regimens for delivery of arsenic trioxide. Due to efficiency of delivery, it may be that dosing levels using the present anti-cancer agent are somewhat lower than current dosing regimens for delivery of arsenic trioxide but they remain a useful guide and final dosing can be adjusted based on standard testing models.

As used herein, the terms "subject" or "individual" or "patient" may refer to any subject, particularly a vertebrate subject, and even more particularly a mammalian subject, for whom arsenic therapy is desired. Suitable vertebrate animals include, but are not restricted to, primates, avians, livestock animals (e.g., sheep, cows, horses, donkeys, pigs), laboratory test animals (e.g., rabbits, mice, rats, guinea pigs, hamsters), companion animals (e.g., cats, dogs) and captive wild animals (e.g., foxes, deer, dingoes). A preferred patient is a human in need of arsenic therapy for a cancer. However, it will be understood that the aforementioned terms do not imply that symptoms are necessarily present.

According to a sixth aspect of the invention there is provided a process for producing an anti-cancer agent including the steps of:
(a) contacting a tumour homing peptide comprising two cysteine residues with an arsenic compound; and
(b) allowing the arsenic to become bound to each of the two cysteine residues to form a cyclised tumour homing peptide comprising a bound arsenic atom;
to thereby produce the anti-cancer agent.

The anti-cancer agent and arsenic compound may be as described for any embodiment of the first aspect.

The arsenic compound may be an oxide of arsenic or an arsenic halide. One non-limiting example of a suitable arsenic oxide is phenylarsine oxide.

In one embodiment, the arsenic compound may comprise an alkyl, hydroxyl or aryl group bonded to arsenic.

In one embodiment, the process may comprise the step (a)(i) of modifying a selected tumour homing peptide to present two cysteine residues. This may be useful when the desired tumour homing peptide does not already display two appropriate cysteine residues. The present invention is not limited to only tumour homing peptides which naturally comprise cysteine residues. The cysteine residues may be bonded to the tumour homing peptide in any of a number of chemical methods which are well known in the art. It is these two added cysteine residues which are subsequently bound to the arsenic in step (b) of the process.

The step of modifying the tumour homing peptide to present two cysteine residues may be a modification such that the tumour homing peptide presents both an N- and C-terminal cysteine residue.

The process may also include, prior to the step of contacting the tumour homing peptide with the arsenic compound, the step of reacting a capping compound with the free amino group of the N-terminus cysteine residue of the tumour homing peptide to form a capping group bonded to the nitrogen of said amino group.

A seventh aspect of the invention resides in an anti-cancer agent when produced by the process of the sixth aspect.

An eighth aspect of the invention resides in a method of delivering a therapeutically effective amount of arsenic to a patient including the step of administering to the patient an appropriate amount of the anti-cancer agent of the first aspect or the pharmaceutical composition of the second aspect, to thereby deliver the therapeutically effective amount of arsenic.

The method of the eighth aspect may be performed according to, and including any of the embodiments as described for, the first to fifth aspects.

A ninth aspect of the invention resides in a method of diagnosing a cancer including the steps of:
(iv) administering an anti-cancer agent of the first aspect comprising at least one radiolabelled atom, to a patient;
(v) allowing the anti-cancer agent to become localised to the cancer; and
(vi) detecting the presence of the at least one radiolabelled atom of the anti-cancer agent,
to thereby diagnose the cancer.

It is expected that a number of radiolabelled atoms or groups will be available to use as a marker in the method of the ninth aspect. Preferably, the radiolabelled atom or group will be or will be part of the stabilising group.

In a preferred embodiment, the stabilising group will be a substituted phenyl and the radiolabelled atom or group will be substituted on the phenyl ring. One preferred radiolabelled atom or group may be a radiolabelled fluorine atom presented on the phenyl ring stabilising group. The fluorine may be ortho, meta or para to the attachment of the phenyl ring to the arsenic but is preferably para. The fluorine isotope employed may be any of those know for use in medical imaging or detection but will preferably be $^{18}$F. Single Photon Emission Computed Tomography (SPECT) or Positron Emission Tomography (PET) or other methods well known in the art may be used for the detection step.

The step of allowing the anti-cancer agent to become localised to the cancer may be a step of allowing the anti-cancer agent to become bound to the cancer or to aggregate within or adjacent the cancer cells.

It will be appreciated, therefore, that the reference in the ninth aspect to the use of an anti-cancer agent of the first aspect includes all such agents described for the first aspect, and including those within the scope of formula I, but with the modification that at least one of those existing atoms or groups is radiolabelled.

The following experimental section describes in more detail the characterisation of certain of the compounds of the invention and their efficacy. The intention is to illustrate certain specific embodiments of the compounds of the invention and their efficacy without limiting the invention in any way

EXPERIMENTAL

Preparation of Arsenic-Peptide Complexes (As(LHP))
Materials

The commercially available reagents were of analytical grade or higher purity, as specified. Sodium meta-arsenite (NaAsO$_2$, ≥99%), triethylamine ((C$_2$H$_5$)$_3$N, ≥99%), sodium phosphate dibasic (Na$_2$HPO$_4$, ≥99%), sodium dihydrogen phosphate dihydrate (NaH$_2$PO$_4$.2H$_2$O, 99%), and phenylarsine oxide (PAO, C$_6$H$_5$AsO, ≥97%) and Trizma® base (≥99.9%, Tris) were obtained from Sigma Aldrich (USA). Arsenic(III) triiodide (AsI$_3$, ≥98%) was obtained from Strem Chemicals (USA), monomethylarsonic acid (MMA (V), CH$_5$AsO$_3$, >97%) was obtained from Wako Pure Chemical Industries (Japan), and formic acid (99%), hydrochloric acid (HCl, 32%) and sodium hydroxide (NaOH, >97%) from Ajax Finechem. The pre-acetylated peptides AcCAYHRLRRC, and AcCARHRYLRC (>98%) and CAYHRRLRC (>98%) were custom synthesised by Peptide 2.0 (USA). AcCAYHRLRRC (leukemia homing peptide) will be referred to herein as LHP and AcCARHRYLRC (scrambled peptide) will be referred to herein as sLHP. Milli-Q water (18.2Ω, Millipore) was used for all dilutions (unless otherwise specified) and to prepare NaOH, phosphate buffer and Tris.HCl buffer solutions.

Methods
Measurement of pH

Where noted, the pH was measured and/or confirmed with Mettler Toledo Seven Compact S220-Micro Kit following calibration with Mettler Toledo technical buffers (4.0, 7.0, and 9.2).

Preparation of Buffers

The phosphate buffers (pH 7 or pH 8, 0.1 M, 100 mL) were prepared using the appropriate volumes of stock solution A (NaH$_2$PO$_4$.2H$_2$O, 0.2 M) and stock solution B (Na$_2$HPO$_4$, 0.2 M) listed in Table 1. The pH was determined, as described previously, and adjusted by the dropwise addition of either Solution A or Solution B as required, prior to dilution to 100 mL with Milli-Q water (final concentration 0.1 M).

TABLE 1

Stock solution combinations for phosphate buffers at specific pH.

| PH, 25° C. | mL Solution A | mL Solution B |
|---|---|---|
| 7.0 | 19.50 | 30.50 |
| 8.0 | 2.65 | 47.35 |

The Tris-HCl buffer (pH 9) was prepared by adding approximately 5 mL HCl (0.2 M) to 50 mL Tris (0.2 M) while monitoring the pH, then diluting with Milli-Q water to 100 mL (final concentration 0.2 M).

Figure 1A:
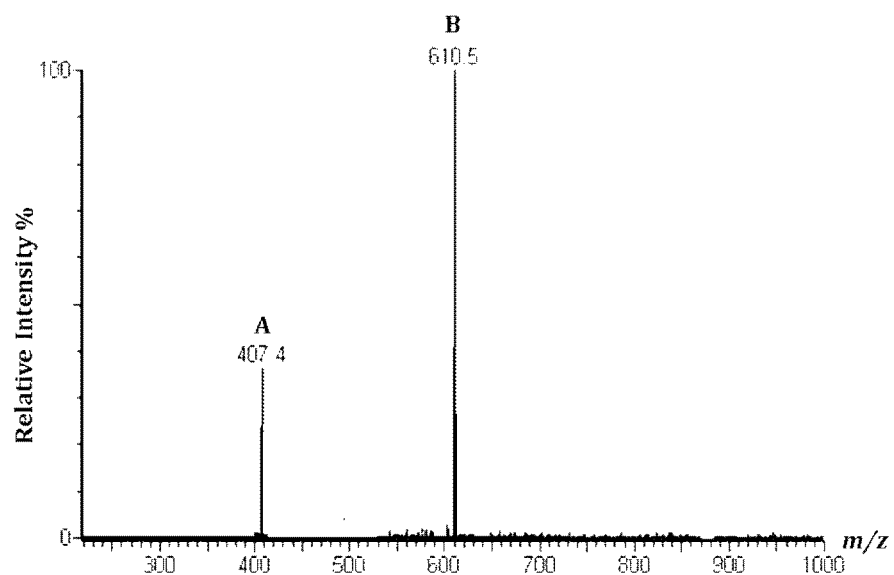
FIG. 1A shows the positive ion ESI-mass spectrum for LHP with peaks at m/z 407.4 and m/z 610.5 assigned $[LHP+3H^+]^{3+}$ and $[LHP+2H^+]^{2+}$, respectively.

Electrospray Ionisation-Mass Spectrometry (ESI-MS)
ESI-MS Analysis of As-LHP Complex Formation ESI-MS was used to detect binding of As species to LHP in order to optimise the complexation conditions. The peptide, CAYHRLRRC, was purchased with an acetylated N-terminus and in a linear conformation to allow the two Cys thiol groups to coordinate to As. Reactions were carried out under various conditions as described herein. Solutions were diluted in Milli-Q water (40×) prior to analysis. FIG. 1A shows the ESI-mass spectrum for LHP.

Operating Conditions for ESI-MS

All mass spectra were collected with a Micromass Quattro Micro triple-quadrupole mass spectrometer (Micromass, UK) employing electrospray ionisation in the positive ion mode. Heated dry nitrogen was the nebulising and drying gas for all experiments. A capillary voltage of 3.00 kV, cone voltage of 35 V, source temperature of 80° C., desolvation temperature of 120° C. and desolvation gas flow of 400 L/h were employed to collect the spectra.

A baseline spectrum for Milli-Q water was collected. The source was rinsed thoroughly with Milli-Q water prior to sample injection until the spectrum resembled the baseline spectrum. Each sample was injected at a flow rate of 10 μL/min using a 1-mL syringe (SGE Analytical Science, Australia). Spectra of the As-LHP products were collected in the m/z range of 300 to 1000. Data acquisition was conducted in continuum mode and typically 80 scans were summed to obtain representative spectra. The spectra were processed with MassLynx software (Waters, 2003). Background subtraction was carried out with a polynomial order of 1 with 40% below the curve, and smoothed with the Savitsky-Golay algorithm. Centroid spectra were then generated with the centre function (Top, area), and each peak was annotated with its respective m/z ratio and intensity.

Method Development for the Formation of As-LHP Complexes and Precursors

Formation of HyAs(LHP)

Table 2 contains the conditions under which triplicate reactions were performed using the reactants, AsI$_3$ and LHP, to prepare HyAs(LHP). All reaction vials were flushed with N$_2$ prior to incubation. A representative aliquot was analysed by ESI-MS at the specified time points (30 min, 1 h, 2 h, 4 h, 8 h, 16 h, 24 h, 48 h) in order to monitor the reaction progress.

TABLE 2

Conditions for triplicate samples for As-LHP preparation

| Trial | Concentrations | Ratio As:LHP | Solvent | Temp (°C.) | PH |
|---|---|---|---|---|---|
| 1 | 5 mM for both reactants | 1:1 | NaOH (20 mM) | 20, 37 | pH 10 |
| 2 | 0.10 mM-3.00 mM | 1:1 | NaOH (20 mM) | 22, 37, 60 | pH 10 |
| 3 | 3 mM As LHP various | 1:2 1:3 1:5 1:10 | NaOH (20 mM) | 22, 37, 60 | pH 10 |
| 4 | As various 3 mM LHP | 2:1 3:1 5:1 10:1 | NaOH (20 mM) | 23, 37, 60 | pH 10 |
| 5 | As various 3 mM LHP | 2:1 3:1 5:1 | Milli-Q water | 24, 37, 60 | pH 7 |
| 6 | As various 3 mM LHP | 2:1 3:1 5:1 | Phosphate buffer ($H_2PO_4^-$/$HPO_4^{2-}$ 0.1M) | 24, 37, 60 | pH 7 |
| 7 | As various 3 mM LHP | 2:1 3:1 5:1 | Triethylamine | 24, 37 | PH 8 |
| 8 | As various 3 mM LHP | 2:1 3:1 5:1 | Phosphate buffer ($H_2PO_4^-$/$HPO_4^{2-}$ 0.1M) | 24, 37 | PH 8 |
| 9 | As various 3 mM LHP | 2:1 3:1 5:1 | Tris.HCl buffer (0.1M) | 24, 37 | PH 9 |

Formation of MeAs(LHP)

MeAs(LHP) preparation was examined by mixing monomethylarsenic acid (MMA(V), 3 mM) with LHP (12 mM) where the excess LHP was to allow for the oxidation of the peptide in the reduction of MMA(V). The compounds were mixed in phosphate buffer ($H_2PO_4^-$/$HPO_4^{2-}$, 0.1 M, pH 8), flushed with $N_2$ and incubated at 37° C. or 60° C. for 1 h, 4 h, 8 h, 16 h, or 24 h. The products were analysed by ESI-MS.

Formation of PhAs(LHP)

Based on the results from the formation of HyAs(LHP), attempts to produce PhAs(LHP), involved a solution of phenylarsine oxide (PAO) (10 mM in phosphate buffer, $H_2PO_4^-$/$HPO_4^{2-}$, 0.1 M, pH 8), prepared by heating until dissolved (80-90° C., 4-8 h). After cooling to room temperature PAO (10 mM) was added to LHP (3 mM), the vials were flushed with $N_2$ and incubated at 37° C. or 60° C. for 1 h, 4 h, 8 h, 16 h, or 24 h. The products were analysed by ESI-MS.

Testing for Formation of PhAs(CAYHRRLRC)

In order to examine the influence of the acetyl group in the complexation of PhAs to LHP, the reaction was attempted with the non-acetylated peptide, CAYHRRLRC. PAO (10 mM) was prepared in phosphate buffer ($H_2PO_4^-$/$HPO_4^{2-}$, 0.1 M, pH 8) and cooled, as previously described. CAYHRRLRC (3 mM) was then added, flushed with $N_2$, and the resultant solution was incubated at 37° C. or 60° C. for 1 h, 4 h, 8 h, 16 h, or 24 h. The aliquots were analysed by ESI-MS.

Preparation of PhAs(sLHP)

PhAs(sLHP) was prepared by reacting PAO (10 mM, as previously described, in phosphate buffer, $H_2PO_4^-$/$HPO_4^{2-}$, 0.1 M, pH 8) and sLHP (3 mM). The vials were flushed with $N_2$ and incubated at 37° C. for 8-16 h. Product was analysed by ESI-MS.

Purification of the various As-LHP complexes

Analytical High Performance Liquid Chromatography (HPLC)

A Shimadzu analytical HPLC system with SCL 10A VP system controller, SIL 10 AD VP auto injector, and LC 10AT VO liquid chromatography unit was used with a DGU 14A degasser and an SPD M10A VP diode array detector. A Waters Sunfire C18 column, 5 μm, 4.6×250 mm (No. 186002560) was used following equilibration with $H_2O$ (0.1% TFA) for 20 mins. A gradient elution with ACN/$H_2O$ each with 0.1% TFA was carried out. All solvents were degassed by filtration and sonication prior to use. The samples were filtered through a 0.20 μm filter (Sartorius) prior to analysis. A solution of free LHP was analysed to establish its elution time.

Preparatory High Performance Liquid Chromatography (HPLC)

Based on the elution profile obtained from the analytical HPLC, purification of the As reaction products was performed using a preparative HPLC employing a Waters Prep LC System was used with a Waters Sunfire Prep C18, OBD 5 μm, 19×150 mm column (No. 186002568) and a 2489 UVNisible detector set to A 220 nm. All solvents were pre-filtered and sonicated prior to sparging with He on the instrument. Each sample was filtered through a 0.20 μm filter (Sartorius) prior to analysis. The column was equilibrated with $H_2O$ (0.1% TFA), for 30 mins prior to running the sample. The flow rate was maintained at 20 mL/min. Table 3 represents the solvent gradient utilised. A solution of free LHP was analysed as a standard. Fractions were collected and analysed by ESI-MS.

TABLE 3

Solvent gradient used for HPLC purification of AsLHP complexes

| Time (min) | % Milli-Q water (0.1% TFA) | % ACN (0.1% TFA) |
|---|---|---|
| 0 | 100 | 0 |
| 2 | 95 | 5 |
| 32 | 65 | 35 |
| 37 | 100 | 0 |
| 40 | 100 | 0 |

Drying the as Complexes

To obtain purified compounds, the identified HPLC fractions were freeze-dried overnight using an Alpha 1-2 LDplus freeze-drier (Christ).

Characterisation of As-LHP Complexes

ESI-MS

Solutions of the As-peptide complexes (100 μM, 0.5% formic acid) were prepared and analysed by ESI-MS according to the operating conditions previously described.

XAS

XAS analysis was performed on solid and solution As-LHP samples. The solid samples were prepared by thoroughly mixing the As-LHP with solid boron nitride (Sigma Aldrich). The dilution ratio was initially determined using the XAFSmass program although it was found that an additional 10× dilution was optimal for analysis in fluorescence mode. This resultant mixture was mounted in 1-mm thick aluminium sample holders and sealed with Kapton tape. The solution samples were prepared for XAS analysis by mixing the As solution (600 μL) with ethylene glycol (300 μL) to prevent crystallisation during rapid freezing. The resultant solution (1 mM final As concentration) was transferred by syringe to the sample holder which was sealed with Kapton tape. The sample was then rapidly submerged in liquid nitrogen and transferred to the liquid helium cryostat where it was analysed at 10° K.

In addition, X-ray absorption spectra were collected for the As standards: solid and solution standards were prepared as described for the As-LHP complexes. The standards included: $AsI_3$, $As_2S_3$, $NaAsO_2$, $NaAsO_4$, MMA(V), PAO, $As(GS)_3$, $MeAs(GS)_2$, and $PhAs(GS)_2$. Arsenic K-edge XAS data were collected at the Australian National Beamline Facility (ANBF, beamline 20B) KEK, Tsukuba, Japan with a beam energy of 2.5 GeV, and beam current of 300-400 mA. A Si[111] channel-cut monochromator was detuned by 50% to reject harmonics. All spectra were recorded in fluorescence mode at ~10° K (maintained with a closed-cycle He CryoIndustries REF-1577-D22 cryostat) using a 36-element Ge-array detector (Eurisys/Canberra Industries) and a 1-mm vertical slit width. Arsenic K-edge EXAFS spectra were collected at the following energy ranges: pre-edge region 11640-11840 eV (10 eV steps); XANES region 11840-11890 eV (0.25 eV steps); and EXAFS region 11890-12468 eV (0.05 Å-1 steps in k-space to 14.2 Å-1). A solid sodium arsenate standard was simultaneously analysed in transmission mode downstream of the sample for calibration whereby the energy of the first peak of the first derivative spectrum (corresponding to the edge energy) was defined as 11871.7 eV. An average of 2-3 scans were collected for all data analyses. Data processing was performed with EXAFSPAK. The DATFIT module of EXAFSPAK was used for multiple linear regression analysis. Background subtraction and normalization were achieved using BACKSUB and FEFF 8.2 was used to calculate the theoretical phase and amplitude functions for fitting the EXAFS data.

NMR Spectroscopy Characterisation

As-LHP samples were analysed in 90% $H_2O$/10% $D_2O$, (pH ~4 adjusted with HCl), or 100% $D_2O$. NMR experiments were carried out using a Varian Unity 500-MHz spectrometer and Vnmrj 2.1B software. Suppression of residual water signal was achieved either by presaturation or by excitation sculpting using a selective square pulse on water 1.5 s long. Proton resonance assignment was obtained by $^1H$ and $^1H$ COSY, TOCSY and NOESY experiments. Carbon assignment was obtained by $^1H$ and $^{13}C$ COSY, TOCSY and NOESY experiments. NOESY experiments were performed with pulse sequences established from the COSY and TOCSY experiments. Spectral processing was performed using ACD/NMR Processor Academic Edition® (2013, ACD Labs, Toronto, Canada). All peaks were calibrated to the water peak at 4.8 ppm.

Graphite Furnace Atomic Absorption Spectroscopy

The solutions were analysed for As using a Perkin-Elmer AAnalyst 600 atomic absorption spectrometer equipped with Winlab 32 AA Furnace program incorporating Zeeman-effect background correction, an AS-800 autosampler and an AA Accessory 7 cooling system. An electrodeless As discharge lamp (Perkin-Elmer) set at a wavelength of 193.7 nm and a slit width of 0.7 nm, gave an instrument energy reading of approximately 54 W. A certified, matrix-matched, arsenic standard solution (Lot #J2-AS02116), purchased from Inorganic Ventures, USA, was used to produce the calibration curve. A Pd/Mg matrix modifier solution (1 mg/mL Pd, 1 mg/mL $Mg(NO_3)_2$) was prepared using Pd and Mg matrix modifier solutions (purchased from Inorganic Ventures, USA). The autosampler volumes dispatched were chemical modifier (5 μL) and sample (20 μL). Arsenic was atomised from the surface of pyrolytic graphite-coated tubes with inserted pyrolytic L'vov platforms using the furnace operating conditions presented in Table 4.

TABLE 4

| Graphite furnace operating conditions | | | | |
|---|---|---|---|---|
| Stage | Temperature ° C. | Ramps | Holds | Gas flow mL · min$^{-1}$ |
| Dry 1 | 110 | 1 | 30 | 250 |
| Dry 2 | 130 | 15 | 30 | 250 |
| Ash | 1200 | 10 | 20 | 250 |
| Atomisation | 2000 | 0 | 5 | 0 |
| Clean out | 2450 | 1 | 3 | 250 |

Results

Formation of as-LHP Complexes

Formation of HyAs(LHP)

Figure 1B:
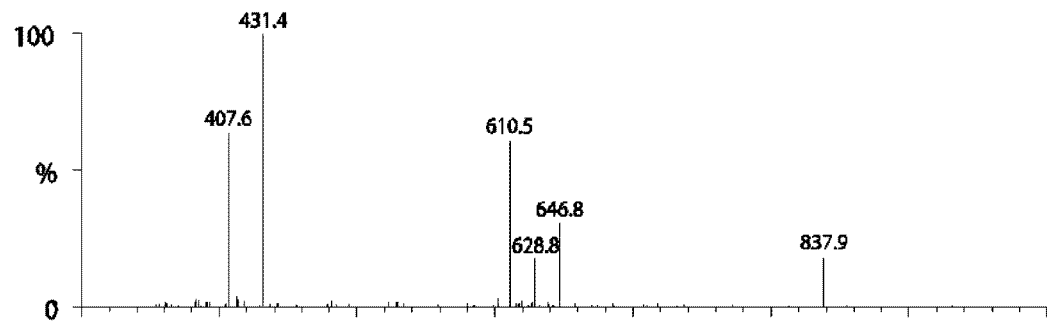
FIG. 1B depicts the ESI-MS results for the 8 h reactions of $AsI_3$ and LHP in (a) phosphate buffer (pH 8) and (b) triethylamine (pH 8) with peaks at m/z 431.4 and m/z 646.8 assigned $[HyAs(LHP)+3H^+]^{3+}$ and $[HyAs(LHP)+2H^+]^{2+}$, respectively, confirming the production of the desired product, HyAs(LHP). Ions at m/z 407.6, m/z 610.5, and m/z 628.8 are assigned to the free peptide, $[LHP+3H^+]^{3+}$, $[LHP+2H^+]^{2+}$, and $[LHP.2H_2O+2H^+]^{2+}$, respectively. The ion at m/z 837.9 is identified as $[HyAs(LHP)_2+3H^+]^{3+}$.
Figure 1B:
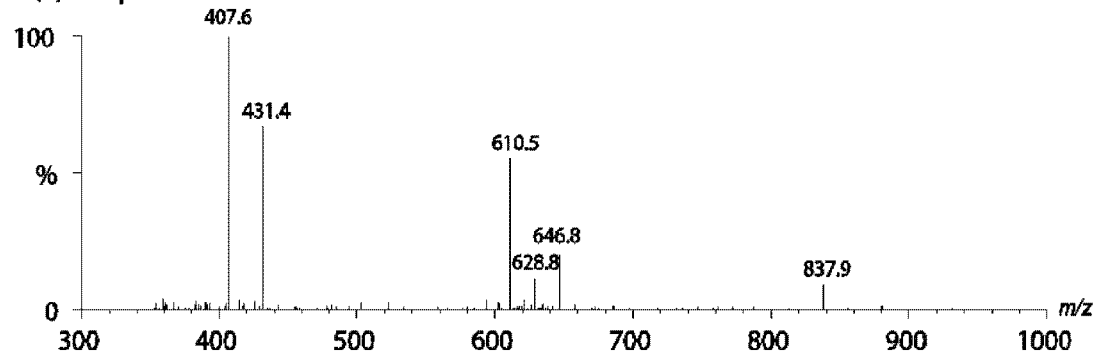
Figure 1C:
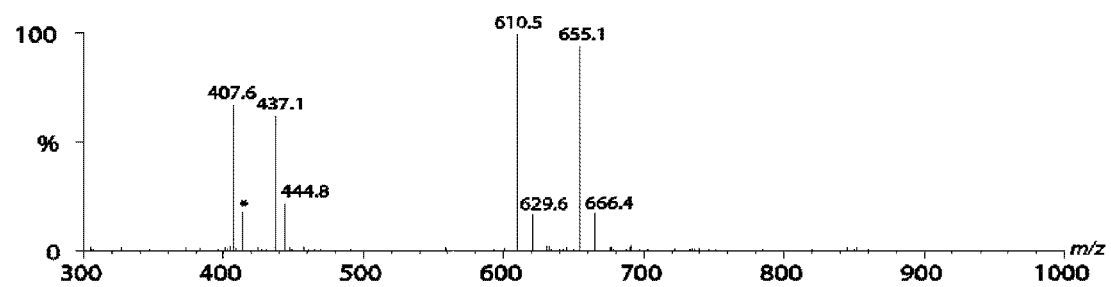
FIG. 1C is the ESI-MS result for the reaction of MMA(V) and LHP in phosphate buffer (pH 8) following 16 h incubation at 37° C. Ions at m/z 437.1 $[MeAs(LHP)+3H^+]^{3+}$, m/z 444.8 $[MeAs(LHP)+Na^++2H^+]^{3+}$, m/z 655.1 $[MeAs(LHP)+2H^+]^{2+}$, and m/z 666.4 $[MeAs(LHP)+Na^++H^+]^{2+}$, confirming the production of the desired product, MeAs(LHP). The free peptide ions occur at m/z 407.6 $[LHP+3H^+]^{3+}$, *=m/z 414.9 $[LHP+Na^++2H^+]^{3+}$, m/z 610.5 $[LHP+2H^+]^{2+}$, m/z 629.6 $[LHP+Na^++H^+]^{2+}$.

Analyses of the products from Trial 1 showed no evidence for the desired As-LHP complex. ESI-MS produced spectra for the free peptide (FIG. 1A) for both temperatures at all time points. Similarly, spectral analysis of the products from Trials 2-6 showed only the existence of the free peptide for all concentrations, temperatures and time points, failing to produce the desired As-LHP complex. As the 60° C. tests over 4 h showed signs of peptide degradation this temperature testing was discontinued. Trial 9 produced no sign of As-LHP complexes for all samples in Tris.HCl buffer (pH 9). The reactions attempted in triethylamine (Trial 7) and in the pH 8 phosphate buffer (Trial 8), however, immediately produced a white precipitate. A sample of this precipitate was dissolved in Milli-Q water/0.5% formic acid and ESI-MS analysis showed small signals of ions that could be attributed to the desired product in both cases, although the abundant peaks were again those of the free peptide. When the reaction was performed at 24° C. the resultant precipitate did not dissolve even after 24 h suggesting that it was not the desired product. Upon incubation of the reaction solution at 37° C., the precipitate dissolved by the 30 min time-point and the sample for this and the 1 and 2 h time-points produced ESI-MS spectra that included dominant peaks that could be assigned to the free peptide and smaller peaks that indicated the formation of the desired product. The samples following incubation for 4 hours at 37° C. for the reactions undertaken at pH 8 produced the spectra in FIG. 1B, confirming formation of HyAs(LHP)) with an abundant molecular ion at m/z 431.4 and a moderately abundant ion at m/z 646.8 corresponding to $[HyAs(LHP)+3H^+]^{3+}$ and $[HyAs(LHP)+2H^+]^{2+}$, respectively. The small peak at m/z 837.9 was assigned as $[HyAs(LHP)_{2+3}H^+]^{3+}$ indicative of the formation of $HyAs(LHP)_2$, and demonstrating that purification of the reaction would be required in order to isolate the desired product, HyAs(LHP). The presence of ions associated with the free peptide at m/z 407.6 and m/z 610.5 corresponding to $[LHP+3H^+]^{3+}$ and $[LHP+2H^+]^{2+}$, respectively, is most likely due to the loss of the associated arsenic in the ionisation process. Analysis of the arsenic concentration in the HPLC-purified product was performed with GFAAS to confirm the purity. The ESI-MS spectra for the 24 and 48 h time periods showed signs of peptide degradation.

Formation of MeAs(LHP)

Figure 10:
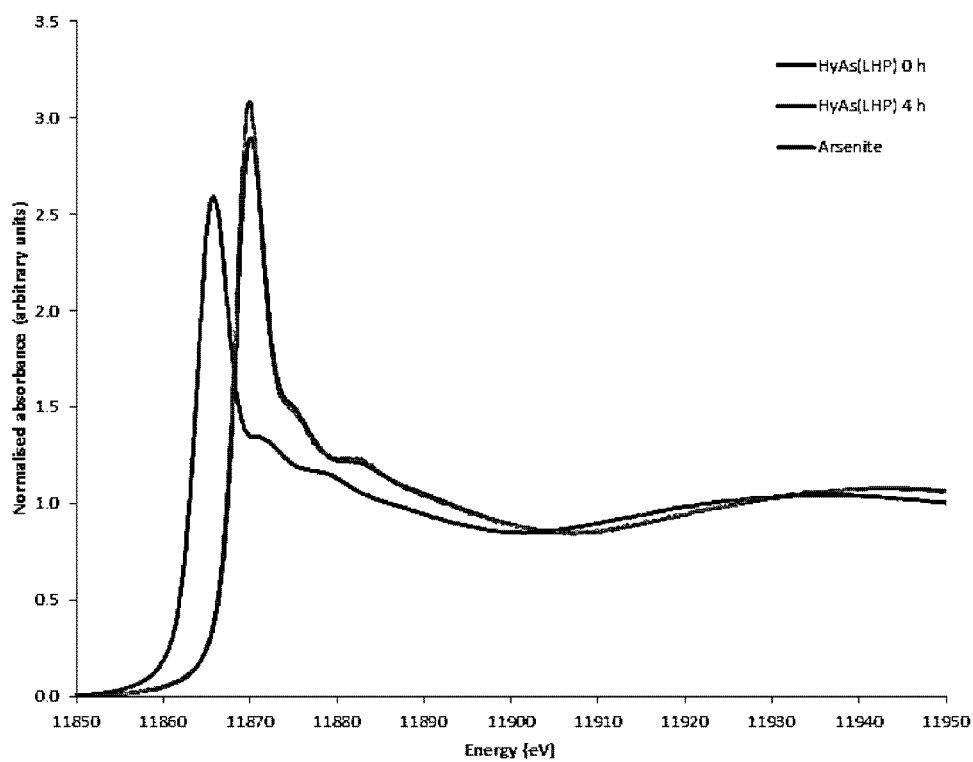
FIG. 10 is the As K-edge XANES spectra for HyAs(LHP) in Milli-Q water at 0 h (blue, left-most trace and peak) and 4 h (red, follows arsenite trace with lower peak value) showing lack of stability over this time period. The 4 hour spectrum is similar to the spectrum of arsenite (green)

The MMA(V) and LHP reaction remained colourless throughout. Small peaks indicative of the MeAs(LHP) product were detected after 4-h of incubation at 37° C. with the abundance of these peaks increasing after incubation of 8 h. There was no significant difference between the 8-h and 16-h incubation, but the longer incubation period once again produced peptide degradation. FIG. 10 depicts the ESI-MS spectrum from the reaction following incubation overnight at 37° C. (16 h) confirming the production of the desired product, MeAs(LHP), with the molecular ion, [MeAs(LHP)+2H$^+$] at m/z 655.1 and [MeAs(LHP)+3H$^+$]$^{3+}$ at m/z 437.1. The abundant ions at m/z 407.6 and m/z 610.5, indicative of the free peptide, [LHP+3H$^+$]$^{3+}$ and [LHP+2H$^+$]$^{2+}$, are consistent with the ionisation process. The other ions present (m/z 414.9 [LHP+Na$^+$+2H$^+$]$^{3+}$, m/z 444.8 [MeAs(LHP)+Na$^+$+2H$^+$]$^{3+}$, m/z 629.6 [LHP+Na$^+$+H$^+$]$^{2+}$, and m/z 666.4 [MeAs(LHP)+Na$^+$+H$^+$]$^{2+}$) are assigned as the analogous peaks with Na$^+$ replacing one of the H$^+$ ions in each case. Interestingly, for this reaction there was no evidence for a dipeptide product.

Formation of PhAs(LHP)

Figure 1D:
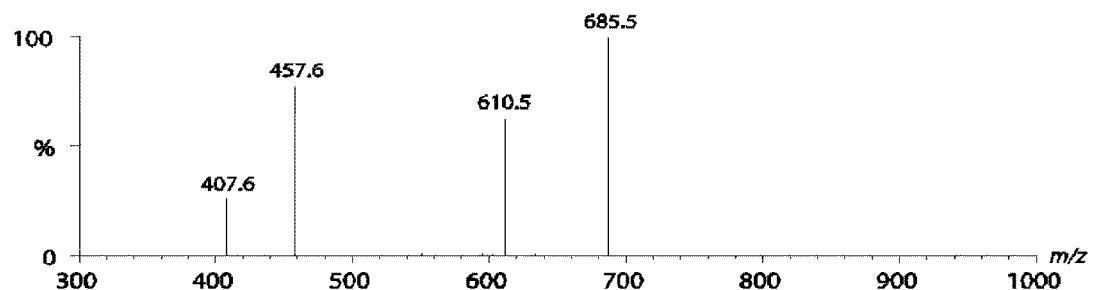
FIG. 1D shows the ESI-MS results for the products from the reaction of PAO and LHP in phosphate buffer (pH 8) following 4 h incubation at 37° C. with ions at m/z 457.6 $[PhAs(LHP)+3H^+]^{3+}$ and m/z 685.5 $[PhAs(LHP)+2H^+]^{2+}$, confirming the production of the desired product, PhAs(LHP). The free peptide ions occur at m/z 407.6 $[LHP+3H^+]^{3+}$, and m/z 610.5 $[LHP+2H^+]^{2+}$.

The reaction of PAO and LHP to produce PhAs(LHP) resulted in immediate precipitation following mixing. As was observed in the case of HyAs(LHP) the ESI-MS analysis of the precipitate showed large ion peaks attributable to the free peptide. Following 1 h incubation at 37° C., the precipitate dissolved and following 4 h incubation at 37° C., ESI-MS analysis (FIG. 1D) showed an abundant peak at m/z 685.5 identified as [PhAs(LHP)+2H$^+$]$^{2+}$ with a moderately abundant ion at m/z 457.6 ([PhAs(LHP)+3H$^+$]$^{3+}$). As was observed for the reactions of HyAs(LHP) and MeAs(LHP), the free peptide was also present in the ESI-MS spectrum as evidenced by the typical indicative peaks at m/z 407.6 [LHP+3H$^+$]$^{3+}$, and m/z 610.5 [LHP+2H$^+$]$^{2+}$, which is removed following HPLC purification, as described in the following paragraph. The 8-h and 16-h incubation periods at 37° C. produced similar ESI-MS results as that for the 4-h incubation but at 24 h there were, once again, signs of product degradation.

Purification of As-LHP complexes
Analytical High Performance Liquid Chromatography (HPLC)

Figure 2A:
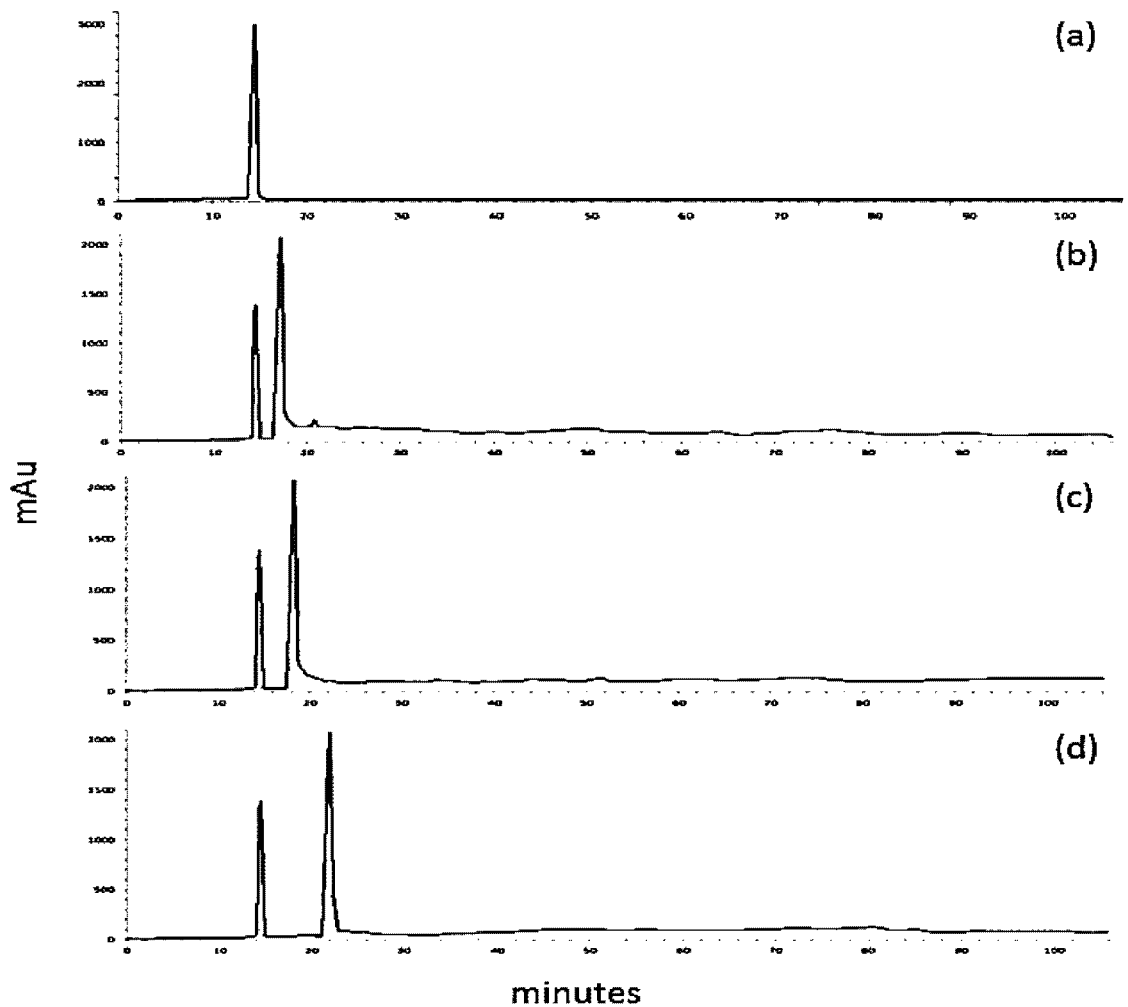
FIG. 2A is a series of HPLC traces from the analytical HPLC for (a) LHP (peak at approx. 15 min in top trace; 14 min and 17 min in second trace; 14 and 19 min in third trace; and 15 and 22 min in last trace); (b) HyAs(LHP); (c) MeAs(LHP), (d) PhAs(LHP). The free peptide (LHP) appears at 14.5 min in all chromatograms, with the specified complexes appearing at the following times: (b) HyAs(LHP) peak at 17.2 min (c) MeAs(LHP) at 18.1 min and (d) PhAs(LHP) at 22.1 min.

The HPLC purification of the As-peptide reaction solutions produced sharp, well separated, peaks. In each chromatogram the free peptide appears at 14.5 min. The peak for HyAs(LHP) (b) appears at 17.2 min while MeAs(LHP) (c) and PhAs(LHP) elute at 18.1 min and 22.1 min, respectively. The HPLC traces are shown in FIG. 2A.

Preparatory High Performance Liquid Chromatography (HPLC)

Upscaling of the reaction and purification by preparatory HPLC resulted in similar elution profiles to those produced by analytical HPLC with the free peptide eluting at 16.9 min, HyAs(LHP) at 18.1 min, MeAs(LHP) at 19.6 min and PhAs(LHP) eluting at 22.8 min. Following freeze-drying of the desired fraction, to remove the solvent, a white solid was produced, corresponding to each of the AsLHP complexes.

Characterisation of the As-LHP Complexes
ESI-MS

Figure 2B:
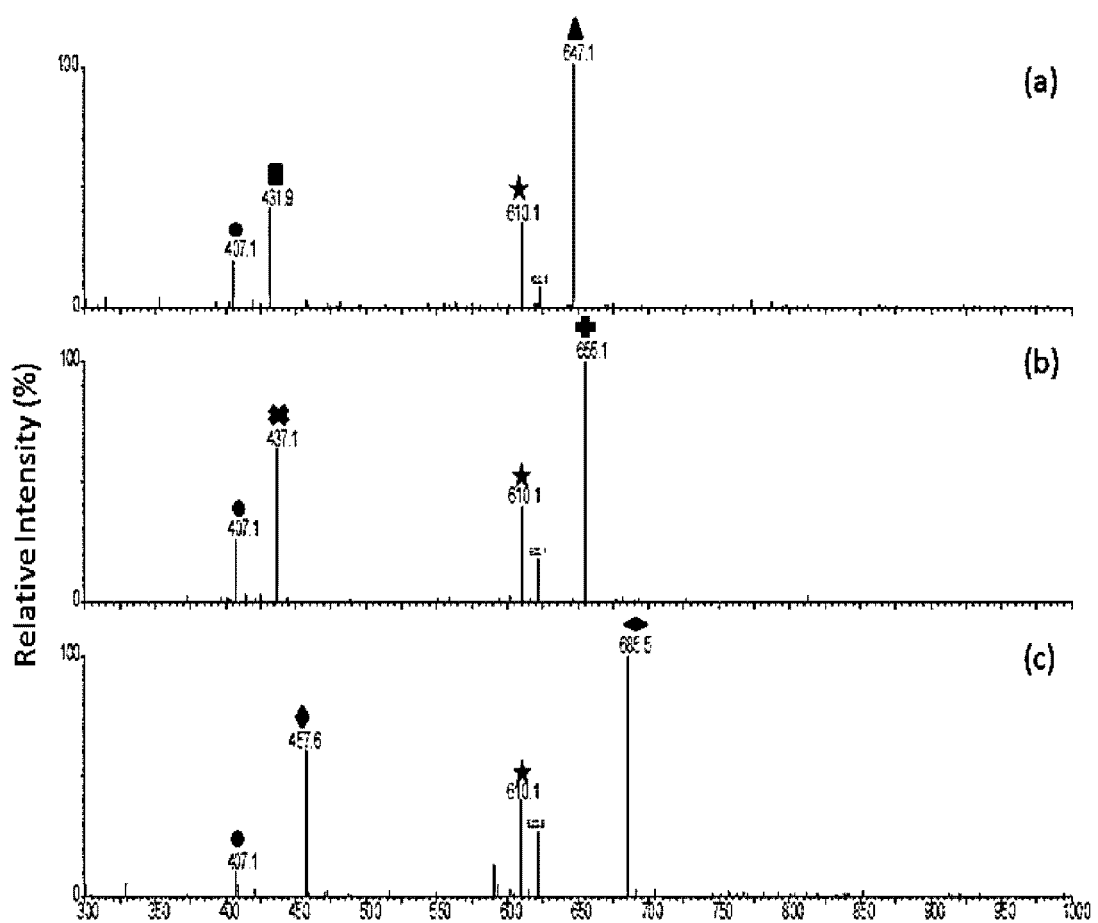
FIG. 2B is a series of positive ion ESI mass spectra characterising the compounds following purification (a) HyAs(LHP); (b) MeAs(LHP), (c) PhAs(LHP). circle=$[LHP+3H^+]^{3+}$, rectangle=$[HyAs(LHP)+3H^+]^{3+}$, star=$[LHP+2H^+]^{2+}$, triangle=$[HyAs(LHP)+2H^+]^{2+}$, X=$[MeAs(LHP)+3H^+]^{3+}$, cross=$[MeAs(LHP)+2H^+]^{2+}$, vertical diamond=$[PhAs(LHP)+3H^+]^{3+}$, horizontal diamond=$[PhAs(LHP)+2H^+]^{2+}$.

The ESI-mass spectra (FIG. 2B) of HyAs(LHP) (a), MeAs(LHP) (b) and PhAs(LHP) (c) all exhibit peaks at m/z 407.4 and 610.5 that can be attributed to LHP and identified as [LHP+3H$^+$]$^{3+}$ and [LHP+2H$^+$]$^{2+}$, respectively. The presence of the free LHP is likely due to the loss of the associated As during the ionisation process. The low abundance ion at m/z 622.3, identified as [LHP+H$^+$+Na$^+$]$^{2+}$, is present in all As(LHP) reactions and final product spectra. HyAs(LHP) (a) exhibits an abundant ion at m/z 647.1 with a moderately abundant ion at m/z 431.4 assigned to [HyAs(LHP)+2H$^+$]$^{2+}$ and [HyAs(LHP)+3H$^+$]$^{3+}$, respectively, confirming the production of the desired product. Analysis of the systems corresponding to MeAs(LHP) (b) and PhAs(LHP) (c) show that each have abundant ions associated with the 2+ charged ion at m/z 655.1 identified as [MeAs(LHP)+2H$^+$]$^{2+}$ and m/z 685.5 identified as [PhAs(LHP)+2H$^+$]$^{2+}$ with moderately abundant 3+ ions at m/z 437.1 ([MeAs(LHP)+3H$^+$]$^{3+}$ and m/z 457.6 ([PhAs(LHP)+3H$^+$]$^{3+}$).

X-Ray Absorption Spectroscopy (XAS)

Figure 3:
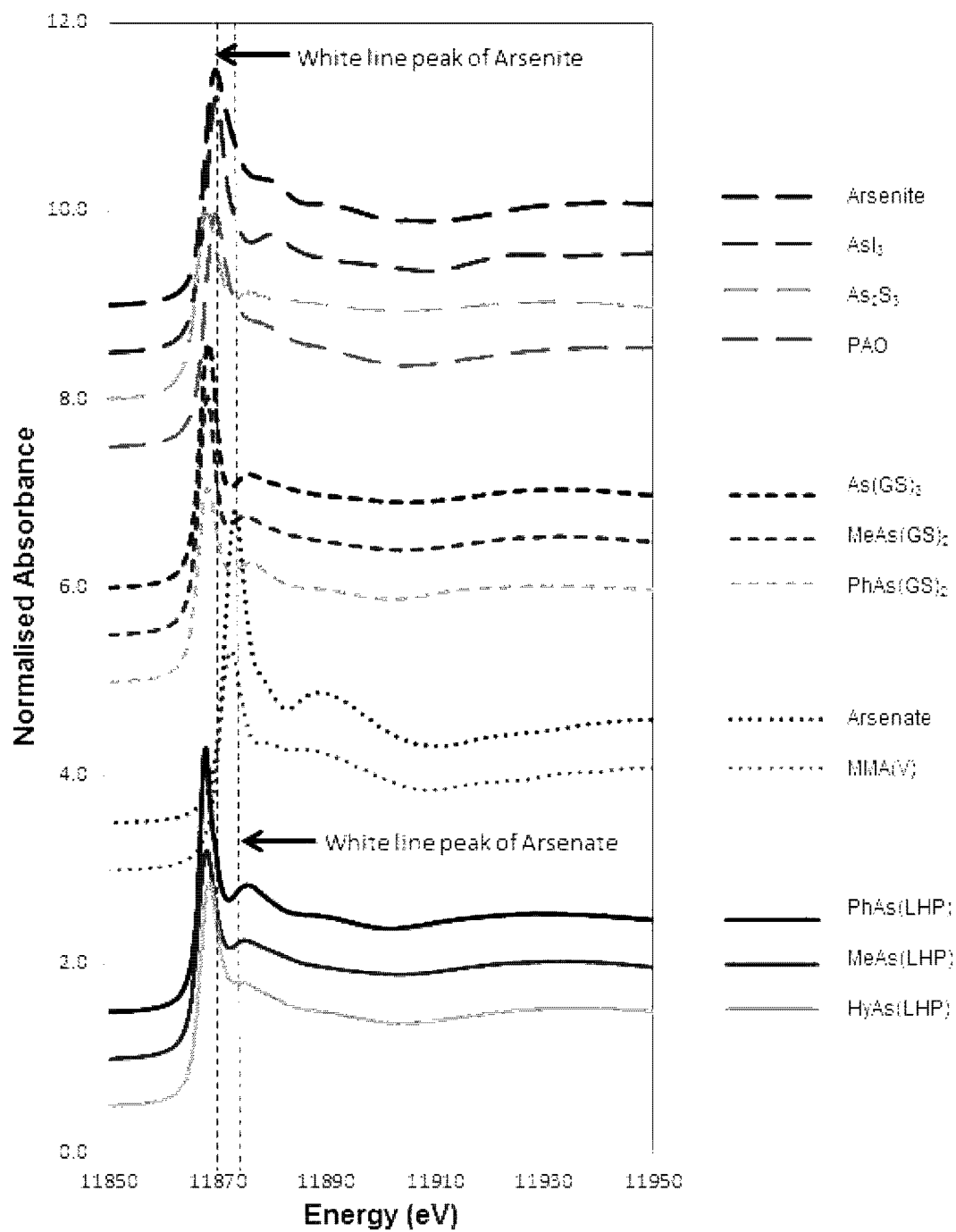
FIG. 3 is a representation of the As K-edge XANES spectra obtained from solid samples of As standards and As-LHP compounds, indicating the structural integrity of arsenic LHP complexes wherein the oxidation state is $As^{3+}$ and the arsenic is bound to two sulfur atoms and the R group.

FIG. 3 shows the comparison of the As K-edge XANES spectra obtained from solid samples of the As standards and the As peptide anti-cancer agents of the first aspect, HyAs (LHP), MeAs(LHP) and PhAs(LHP). The corresponding energies of the edges (obtained from the first peak of the first derivative spectrum) and the white line peaks for all the solid samples are listed in Table 5, below. The edge energies of the As(III) compound, sodium arsenite (11867.89 eV, dashed black line, FIG. 3), and the As(V) compound, sodium arsenate (11871.38 eV, dotted black line, FIG. 3) differed by 3.49 eV. Inspection of the edge energies for the As(III) complexes reveals that the sulfur-bound As(III) compounds (short dashed lines, FIG. 3) exhibit edge energies lower (11866.09 eV to 11867.07 eV) than those of the oxygen-bound As(III) compounds (11867.89 eV to 11868.64 eV, dashed lines, FIG. 3). The edge energy for HyAs(LHP)(solid green line, FIG. 3) was 11866.97 eV which lies at the high end of the range for the sulfur-bound As(III) compounds but is significantly lower than that exhibited by the oxygen-bound As(III) compound, sodium arsenite. The profile of the spectra for the sulfur-bound As(III) complexes also exhibited a characteristic trough at approximately 11871.7 eV whereas the spectra for the oxygen-bound As(III) compounds did not exhibit this pronounced trough in the post-edge region (FIG. 3). The spectra obtained for MeAs(LHP) (solid red line) and PhAs(LHP) (solid black line) both exhibited the characteristic post edge trough of the sulfur-bound As(III) complexes. This depression was not as marked in the spectrum of HyAs(LHP) (solid green line), perhaps due to the presence of the oxygen in this structure.

TABLE 5

Arsenic K-edge and white line peak XANES energies of solid samples of As-LHP anti-cancer agents and As standards

| As oxidation state | Compound | K-edge energy | White line peak | Coordinating Atoms |
|---|---|---|---|---|
| III | PhAs(LHP) | 11865.90 | 11868.1 | Ph, 2S |
| III | As$_2$S$_3$ | 11866.09 | 11868.2 | 3S |
| III | MeAs(LHP) | 11866.27 | 11868.3 | C, 2S |
| III | PhAs(GS)$_2$ | 11866.37 | 11868.4 | Ph, 2S |
| III | MeAs(GS)$_2$ | 11866.44 | 11868.4 | C, 2S |
| III | HyAs(LHP) | 11866.97 | 11868.7 | O, 2S |
| III | Me$_2$As(GS) | 11867.01 | 11868.3 | 2C, S |
| III | As(GS)$_3$ | 11867.07 | 11868.4 | 3S |
| III | AsI$_3$ | 11867.27 | 11869.3 | 3I |
| III | Arsenite | 11867.89 | 11869.8 | 3O |
| III | PhAsO | 11868.64 | 11869.6 | Ph, =O, |
| V | DMA(V) | 11869.47 | 11872.0 | 2C, =O, O |
| V | MMA(V) | 11870.64 | 11872.6 | C, =O, 2O |
| V | Arsenate | 11871.38 | 11873.6 | =O, 3O |

The methylated arsenic (V) compound, MMA(V) (dotted red line), exhibited an edge energy at 11870.64 eV, 2.75 eV higher than the monomethylated arsenic (III) complex, MeAs$^{III}$(GS)$_2$ (11866.44 eV, short dashed red line, FIG. 3). The edge energy for MeAs(LHP) (solid red line, FIG. 3) occurred at 11866.27 eV and corresponded to that of sulfur-bound As complexes. Additionally, the post-edge profile of the XAS spectrum of MeAs(LHP) closely resembled that of the MeAs$^{III}$(GS)$_2$ spectrum. PhAsO (dashed blue line, FIG. 3) exhibited an edge energy of 11868.64 eV which is closest to that of arsenite. This is representative of the fact that the arsenic is bound to the electronegative O in each case. The PhAs(LHP) compound (solid black line) exhibited an edge energy (11865.90 eV) which occurred at the lower range of the C/S-bound As(III) standards. The shape of the PhAs (LHP) spectrum resembled that of the MeAs$^{III}$(GS)$_2$ spectrum (short dashed red line) and that of the PhAs$^{III}$(GS)$_2$ spectrum (dashed green line) but the intensity of the white line peak was greater than either of the standards.

Figure 4:
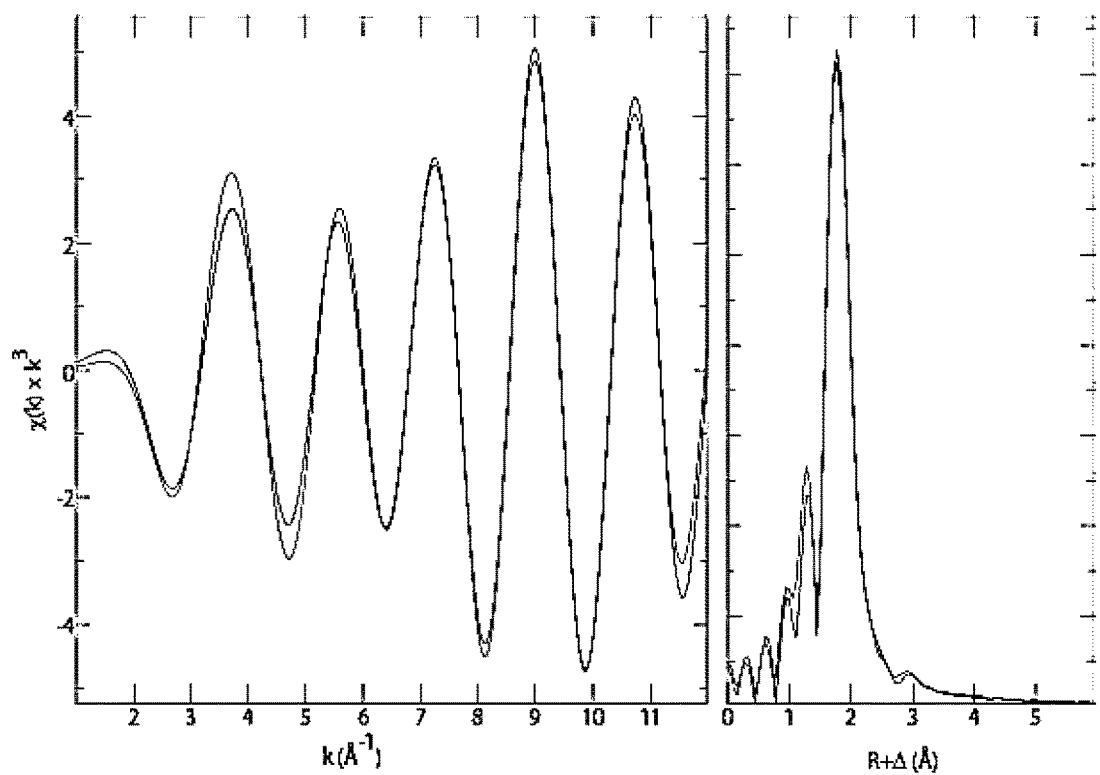
FIG. 4 is a graphical representation of an EXAFS analysis (left) and corresponding Fourier transform (right) of a solid sample of HyAs(LHP) showing experimental (black) and calculated (red) data for Fit 3 (2S and 1C) as shown in table 6; confirming that the $As^{3+}$ is bound to 2 sulfur atoms and 1 oxygen atom.

Table 6 represents the summary of the curve-fitting simulations performed for EXAFS data obtained from HyAs (LHP). These correspond to As(III) which is typically coordinated to three atoms in a trigonal planar or trigonal pyramidal manner. Simulation of three sulfur atoms coordinated to arsenic (Fit 2) resulted in an increased fit-error when compared to that for two sulfur atoms (Fit 1) suggesting that it was more likely that two sulfur atoms were bound to arsenic. Fitting of a third backscatterer to arsenic indicated that the third atom was likely to be either oxygen or carbon (Fits 3 and 4). The scenario of 2 sulfur atoms and 1 carbon atom initially produced a negative Debye-Waller factor; as such the factor was subsequently fixed to obtain the result shown in Fit 4 (Table 6). FIG. 4 shows the experimental and calculated EXAFS and Fourier Transform analyses for Fit 3, showing reasonable agreement for the radial distribution below 2.5 Å. Other possible configurations that were also examined included 1 sulfur and 2 oxygen atoms (Fit 5), and 1 sulfur and 2 carbon atoms with the latter discounted due to the physically infeasible negative Debye-Waller factors produced. Fixing the Debye-Waller factor to reduce this error resulted in unreasonable $E_0$ values.

TABLE 6

Summary of EXAFS fitting results for solid state HyAs(LHP).

| Fit Number | Scatterers N | Interatomic distance (R) | Debye-Waller factor ($\delta 2$, Å-2) | $-\Delta E_0$ (eV) | Fit error (%) |
|---|---|---|---|---|---|
| 1 | 2S | 2.265(3) | 0.0016(2) | 9.8(7) | 47 |
| 2 | 3S | 2.295(4) | 0.0053(3) | 11.0(7) | 57 |
| 3 | 2S | 2.238(3) | 0.0019(2) | 14.6 (fixed) | 34 |
|   | 1P | 1.778(4) | 0.0010(5) | | |
| 4 | 2S | 2.244(2) | 0.0016(2) | 13.5(5) | 37 |
|   | 1C | 1.847(8) | 0.002(fixed) | | |
| 5 | 1S | 2.207(6) | 0.002(fixed)* | 20(1) | 60 |
|   | 2P | 1.747(5) | | | |

*The Fit for 1S and 2O along with that for 2S and 1C produced negative Debye-Waller factors prior to fixing. All attempts for 1S and 2C produced negative Debye-Waller factors.

Figure 5:
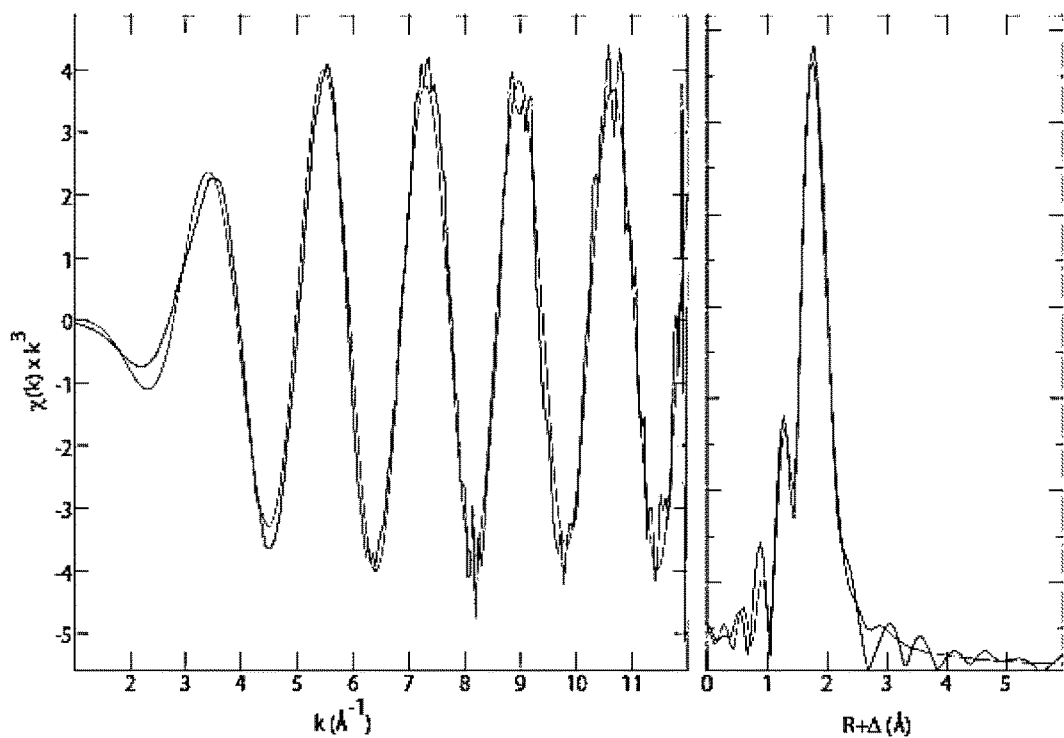
FIG. 5 is a graphical representation of an EXAFS analysis (left) and corresponding Fourier transform (right) of the solid sample of MeAs(LHP) showing experimental (black) and calculated (red) data using a single scattering fit (the first coordination shell) for Fit 4 (2S and 1C) as shown in table 7; confirming that the $As^{3+}$ is bound to 2 sulfur atoms and 1 carbon atom.

Table 7 (below) shows a summary of the simulations of potential models to the EXAFS spectra produced for the MeAs(LHP). Similarly, initial fitting of arsenic coordinated solely to sulfur confirmed that a model with two sulfur atoms produced closer fits (Fit 1 versus Fit 2) since the coordination of As to three sulfur atoms increased the fit error. Attempts to examine the scenarios for a combination of 1 sulfur and either 2 oxygen atoms or 2 carbon atoms bonded to arsenic produced results that were not feasible for the Debye-Waller factor, the $E_0$, or both of these parameters. Furthermore, this could not be corrected by fixing the parameters. Fitting for arsenic bound to two sulfur atoms and either one oxygen or one carbon atom produced feasible results. In conclusion, the best fits were obtained for As(III) bound to two sulfurs and either one oxygen (Fit 3) or one carbon (Fit 4, as shown in FIG. 5).

TABLE 7

Summary of EXAFS fitting results for solid state MeAs(LHP).

| Fit Number | Scatterers N | Interatomic distance (R) | Debye-Waller factor ($\delta 2$, Å-2) | $-\Delta E_0$ (eV) | Fit error (%) |
|---|---|---|---|---|---|
| 1 | 2S | 2.250(1) | 0.0018(1) | 12.9(4) | 25 |
| 2 | 3S | 2.245(2) | 0.0047(1) | 13.8(3) | 28 |
| 3 | 2S | 2.246(1) | 0.00106(8) | 14.4(3) | 21 |
|   | 1O | 1.898(4) | 0.0025(8) | | |
| 4 | 2S | 2.245(1) | 0.00109(7) | 14.6(3) | 19 |
|   | 1C | 1.952(6) | 0.002(fixed) | | |

*The fitting for 1S and 2O along with that for 1S and 2C produced negative Debye-Waller factors and/or unfeasible $E_0$ values. The initial attempt to fit 2S and 1 C produced negative Debye-Waller factors prior to fixing.

Figure 6:
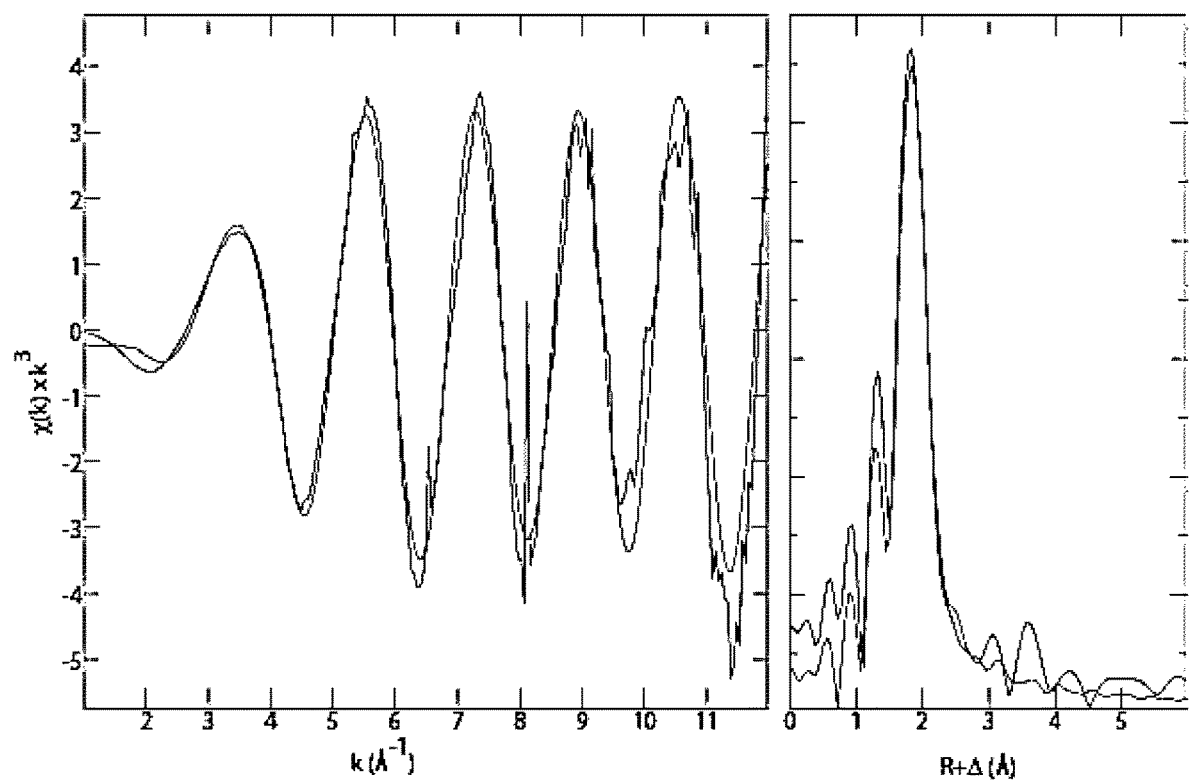
FIG. 6 is a graphical representation of an EXAFS analysis (left) and corresponding Fourier transform (right) of the solid sample of PhAs(LHP) showing experimental (black) and calculated (red) data using a single scattering fit (the first coordination shell) for Fit 4 (2S and 1C) as shown in table 8; confirming that the $As^{3+}$ is bound to 2 sulfur atoms and 1 carbon atom.

Table 8 shows the summary of the simulations obtained from models of As coordination from the EXAFS spectrum of PhAs(LHP). Once again the best fit was obtained when two sulfur atoms were coordinated to arsenic (Fit 1) rather than three sulfur atoms (Fit 2). Poor results were obtained for models in which As was coordinated to either one sulfur and two oxygen atoms or one sulfur and two carbon atoms (fits not shown). While the models that included arsenic bound to two sulfur atoms and either one oxygen atom or one carbon atom initially produced an unreasonable Debye-Waller factor, this was improved when this factor was fixed and promising fits were obtained (Fits 3 and 4), although the fit error for 2S and 1O in comparison to 2S and 1C was significantly larger. As such the results for Fit 4 are shown in FIG. 6.

TABLE 8

Summary of EXAFS fitting results for solid state PhAs(LHP).

| Fit | Scatterers N | Interatomic distance (R) | Debye-Waller factor ($\delta 2$, Å-2) | $-\Delta E_0$ (eV) | Fit error (%) |
|---|---|---|---|---|---|
| 1 | 2S | 2.266(2) | 0.0027(1) | 10.6(6) | 43 |
| 2 | 3S | 2.257(3) | 0.0058(2) | 12.6(6) | 53 |
| 3 | 2S | 2.251(4) | 0.0027(2) | 14(1) | 66 |
|   | 1O | 1.80(5) | 0.002(fixed) | 14(1) | |
| 4 | 2S | 2.253(2) | 0.0022(1) | 14.2(4) | 36 |
|   | 1C | 1.94(7) | 0.002 (fixed) | 14.2(4) | |

*The fitting for 1S and 2O along with that for 1S and 2C produced negative Debye-Waller factors and/or unfeasible $E_0$ values. The initial attempt to fit 2S and 1 C along with that for 2S and 1O produced negative Debye-Waller factors prior to fixing.

Nuclear Magnetic Resonance Spectroscopy

Assignments of $^1$H NMR resonances to residues in the free peptide, AcCAYHRLRRC, were made using combined—$^1$H and $^1$H 2-D COSY, TOCSY and NOESY NMR spectral data (Table 9). The $^{13}$C NMR assignments were made by $^1$H and $^{13}$C 2-D COSY, TOCSY, NOESY, and HMBC NMR spectral data. Spectra were also obtained from CAYHRRLRC under the same conditions in order to specifically identify and assign the individual cysteine residues in the peptide, AcCAYHRLRRC.

TABLE 9

$^1$H and $^{13}$C Chemical Shift Assignments of LHP, 22 mM, 90% H$_2$O, 10% D$_2$O, pH 3.85, T 298.1K

| Residue | $^1$H | $\delta$ chemical shift (ppm) | $^{13}$C | $\delta$ chemical shift (ppm) |
|---|---|---|---|---|
| Ac | CH$_3$ | 2.08 | CH$_3$ | 26.62 |
|   |   |   | C=O | 172.13 |

TABLE 9-continued

¹H and ¹³C Chemical Shift Assignments of LHP,
22 mM, 90% H₂O, 10% D₂O, pH 3.85, T 298.1K

| Residue | ¹H | δ chemical shift (ppm) | ¹³C | δ chemical shift (ppm) |
|---|---|---|---|---|
| Cys-1 | NH | 7.84 | Cα | 61.53 |
|  | Hα | 4.41 | Cβ | 31.01 |
|  | Hβ | 3.04, 3.14 | C=O | 173.35 |
| Ala-2 | NH | 8.49 | Cα | 57.55 |
|  | Hα | 4.37 | Cβ | 21.61 |
|  | Hβ | 1.48 | C=O | 174.44 |
| Tyr-3 | NH | 8.21 | Cα | 63.91 |
|  | Hα | 4.21 | Cβ | 28.29 |
|  | Hβ | 3.05 | Cγ | 132.15 |
|  | Hδ | 6.84 | Cδ | 131.33 |
|  | Hε | 7.10 | Cε | 119.43 |
|  |  |  | Cξ | 160.72 |
|  |  |  | C=O | 174.11 |
| His-4 | NH | 8.14 | Cα | 60.23 |
|  | Hα | 4.52 | Cβ | 36.59 |
|  | Hβ | 2.96, 3.08 | Cγ | 137.31 |
|  | CHδ | 8.62 | Cδ | 123.90 |
|  | NHδ | 7.25 | Cε | 139.22 |
|  | CHε | 3.98 | C=O | 173.14 |
|  | NHε | 8.46 |  |  |
| Arg-5 | NH | 8.20 | Cα | 60.10 |
|  | Hα | 4.08 | Cβ | 31.92 |
|  | Hβ | 1.90, 1.97 | Cγ | 26.99 |
|  | Hγ | 1.53 | Cδ | 44.21 |
|  | Hδ | 2.95 | Cξ | 161.09 |
|  |  |  | C=O | 173.26 |
| Leu-6 | NH | 8.19 | Cα | 59.21 |
|  | Hα | 4.22 | Cβ | 43.22 |
|  | Hβ | 1.49 | Cγ | 27.41 |
|  | Hγ | 1.48 | Cδ | 25.13 |
|  | Hδ | 0.75, 0.80 | C=O | 175.62 |
| Arg-7 | NH | 8.13 | Cα | 60.13 |
|  | Hα | 4.20 | Cβ | 32.25 |
|  | Hβ | 2.11, 2.16 | Cγ | 27.22 |
|  | Hγ | 1.49 | Cδ | 43.38 |
|  | Hδ | 3.08 | Cξ | 161.32 |
|  |  |  | C=O | 172.74 |
| Arg-8 | NH | 8.15 | Cα | 60.07 |
|  | Hα | 4.20 | Cβ | 32.23 |
|  | Hβ | 2.11, 2.16 | Cγ | 27.18 |
|  | Hγ | 1.49 | Cδ | 43.29 |
|  | Hδ | 3.08 | Cξ | 161.26 |
|  |  |  | C=O | 172.53 |
| Cys-9 | NH | 7.91 | Cα | 64.21 |
|  | Hα | 4.52 | Cβ | 27.43 |
|  | Hβ | 2.97, 2.99 | C=O | 171.20 |

The NMR spectra of MeAs(LHP), and PhAs(LHP) produced the same patterns of chemical shifts for all the amino acid residues apart from the two cysteines for which there were chemical shifts consistent with binding of As to the sulfhydryl groups (Tables 10 and 11 below). Peaks were also assigned to the methyl group for MeAs(LHP) and the phenyl ring for PhAs(LHP).

TABLE 10

¹H and ¹³C Chemical Shift Assignments of R group
and Cysteine residues for MeAs(LHP), 22 mM,
90% H₂O, 10% D₂O, pH 3.85, T 298.1K

| R group or residue | ¹H | δ chemical shift (ppm) | ¹³C | δ chemical shift (ppm) |
|---|---|---|---|---|
| Me | CH3 | 4.58 | CH3 | 84.81 |
| Cys-1 | NH | 7.84 | Cα | 61.53 |
|  | Hα | 4.46 | Cβ | 38.21 |
|  | Hβ | 3.25, 3.35 | C=O | 173.35 |
| Cys-9 | NH | 7.91 | Cα | 64.21 |
|  | Hα | 4.56 | Cβ | 34.63 |
|  | Hβ | 3.19, 3.21 | C=O | 171.20 |

TABLE 11

¹H and ¹³C Chemical Shift Assignments of R group
and Cysteine residues for PhAs(LHP), 22 mM,
90% H₂O, 10% D₂O, pH 3.85, T 298.1K

| R group or residue | ¹H | δ chemical shift (ppm) | ¹³C | δ chemical shift (ppm) |
|---|---|---|---|---|
| Ph | m-H | 7.52 | C (As) | 138.81 |
|  | p-H | 7.53 | C (m) | 131.7 |
|  | o-H | 7.78 | C (p) | 128.9 |
|  |  |  | C (o) | 130.3 |
| Cys-1 | NH | 7.85 | Cα | 61.54 |
|  | Hα | 4.41 | Cβ | 38.24 |
|  | Hβ | 3.28, 3.38 | C=O | 173.35 |
| Cys-9 | NH | 7.91 | Cα | 64.21 |
|  | Hα | 4.52 | Cβ | 34.65 |
|  | Hβ | 3.21, 3.24 | C=O | 171.20 |

Graphite Furnace Atomic Absorption Spectroscopy

GFAAS was carried out to confirm the purity of the As-peptide products and the results are shown in table 12, below. Good agreement between the theoretically and experimentally determined As concentrations is seen.

TABLE 12

GFAAS data determining arsenic microanalysis for
the various As containing peptides of the invention.

| Sample | As theoretical % | As experiment % | Experiment/ theoretical % |
|---|---|---|---|
| HyAs(LHP) | 0.0573 | 0.0472 | 82.4 |
| MeAs(LHP) | 0.0574 | 0.0566 | 98.6 |
| PhAs(LHP) | 0.0548 | 0.0547 | 99.8 |

Investigation of Isomers of PhAs(LHP)
Method

A Shimadzu analytical HPLC system with Prominence-i LC2030C system controller, auto injector and liquid chromatograph unit was used for the purification of PhAs(LHP). A Waters Sunfire C18 column, 5 μm, 4.6×250 mm (No. 186002560) was used following equilibration with H₂O (0.1% TFA) for 20 mins. All solvents were degassed by filtration and sonication prior to use. The sample of PhAs (LHP) was freshly prepared from the reaction of LHP (3 mM) and PAO (10 mM) in MilliQ water (total volume 1 mL) incubated at 37° C. overnight. It was then filtered through a 0.2-μm filter (Sartorius) prior to being injected onto the column and analysed in order to determine elution times of the fractions of interest. The reverse-phase analytical elution gradient used for optimal peak separation is listed in Table 13, below.

TABLE 13

Reverse-phase analytical and preparatory HPLC eluent gradient used for analysis and purification of PhAs(LHP).

| Time (min) | Solvent A (%) | Solvent B (%) |
|---|---|---|
| 0.01 | 100 | 0 |
| 2.00 | 80 | 20 |
| 20.00 | 74 | 26 |
| 20.01 | 0 | 100 |
| 23.01 | 100 | 0 |

Based on the elution profile obtained from the analytical HPLC, purification of PhAs(LHP) was performed using preparative HPLC employing a Shimadzu SIL-10AP auto sampler, Shimadzu LC-20AP preparative liquid chromatograph, Shimadzu FCV-200AL quaternary valve, Shimadzu SPD-M20A diode array detector, Shimadzu DGU-20A5R degassing unit, Shimadzu CDM-20A communications bus module, LabSolutions Software and a Luna 5u C18(2) column (250×21.20 mm, 5 micron, Phenomenex). The column was equilibrated with $H_2O$ (0.1% TFA, 20 min). A solution (6 mL) of the PhAs(LHP), prepared according to the optimum reaction conditions (as determined from the results of the method development), was injected onto the column and separated using the eluent gradients detailed in Table 13. The flow rate was maintained at 15 mL/min and the fractions were detected at A 254 nm. The major fractions were collected and characterised by ESI-MS. Where required, the identified HPLC fractions were dried using an Alpha 1-2 LDplus Freeze Dryer (Christ) to obtain pure compounds.

Results

Figure 7:
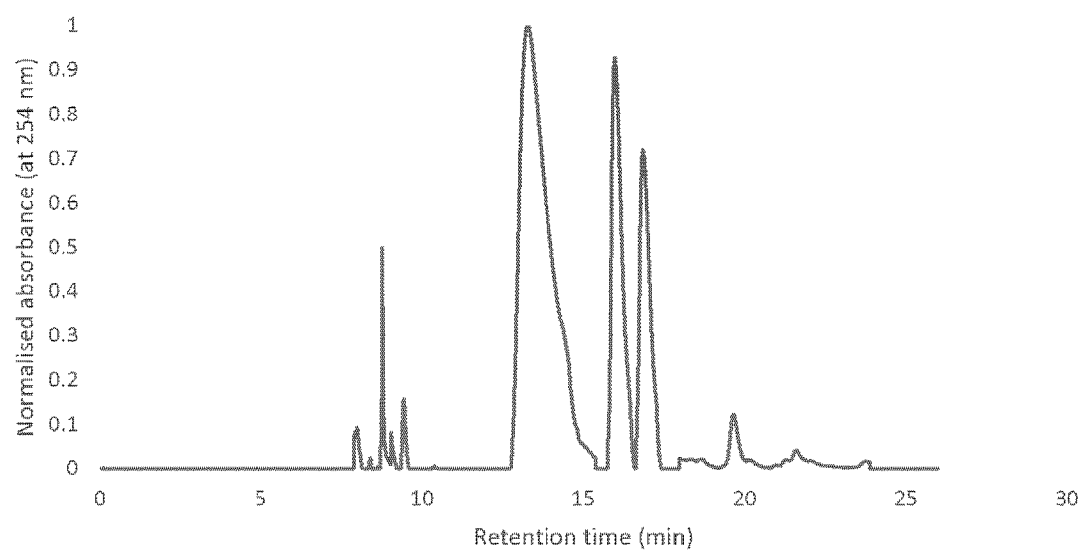
FIG. 7 is the reverse-phase preparative HPLC chromatogram of the reaction products of PAO (10 mM) with LHP (3 mM) performed in MilliQ water at 37° C. The identities of each major fraction were confirmed by ESI-MS. PAO was eluted at 13.28 mins, PhAs(LHP) was eluted at 15.99 and 16.86 mins. The identities of the components of the minor fractions were unconfirmed.
Figure 8:
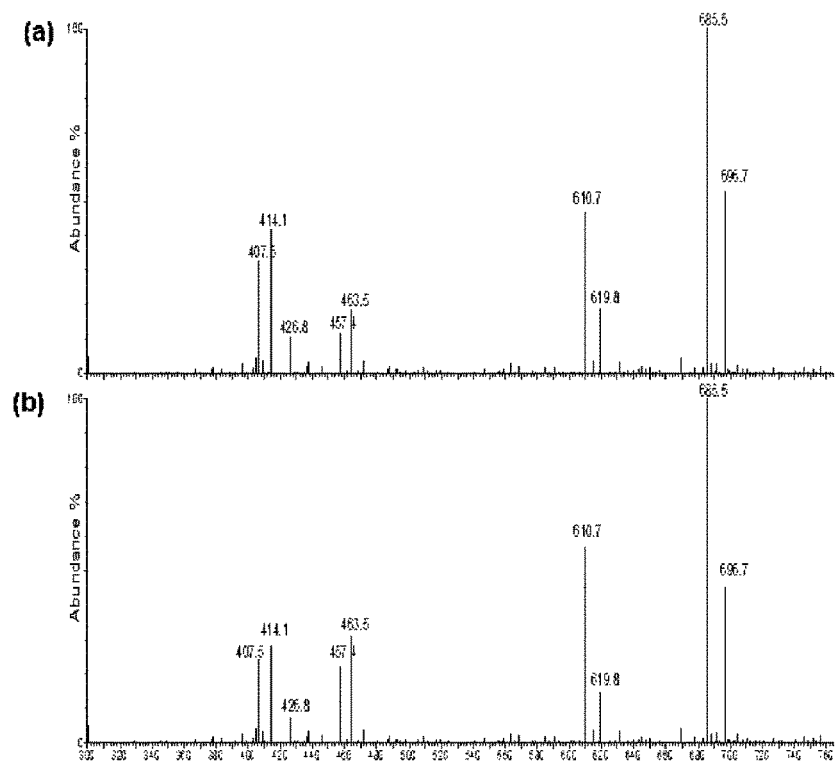
FIG. 8 is the positive ion ESI mass spectra of (a) Fraction 1 and (b) Fraction 2. Peaks are identified as: m/z 407.5= $[LHP+3H^+]^{3+}$, m/z 414.1=$[LHP+2H^++Na^+]^{3+}$, m/z 457.4= $[PhAs(LHP)+3H^+]^{3+}$, m/z 463.5=$[PhAs(LHP)+3H^++H_2O]^{3+}$, m/z 610.7=$[LHP+2H]^{2+}$, m/z 619.8=$[LHP+2H^++H_2O]^{2+}$, m/z 685.5=$[PhAs(LHP)+2H^+]^{2+}$, m/z 696.7=$[PhAs(LHP)+H^++Na^+]^{2+}$, confirming each of the fractions as the same compound, PhAs(LHP)

Using the above separation process, two peaks (eluting at 15.99 and 16.86 mins, preparatory HPLC, FIG. 7) were evident. When isolated and collected, each peak was identified by ESI-MS as PhAs(LHP). The spectra (FIG. 8) for the two fractions were similar with ESI-MS peaks that could be attributed to LHP and to PhAs(LHP). The peaks exhibited at m/z 407.5, 414.1, 610.7 and 619.8 are attributed to LHP, and are identified as $[LHP+3H^+]^{3+}$, $[LHP+2H^++Na^+]^{3+}$, $[LHP+2H^+]^{2+}$, and $[LHP+2H^++H_2O]^{2+}$, respectively. The presence of the free peptide is a result of the ionisation process. The peaks exhibited at m/z 457.4, 463.5, 685.5 and 696.7 are indicative of PhAs(LHP), and are identified as $[PhAs(LHP)+3H^+]^{3+}$, $[PhAs(LHP)+3H^++H_2O]^{3+}$, $[PhAs(LHP)+2H]^{2+}$, and $[PhAs(LHP)+H^++Na^+]^{2+}$, respectively.

Figure 9:
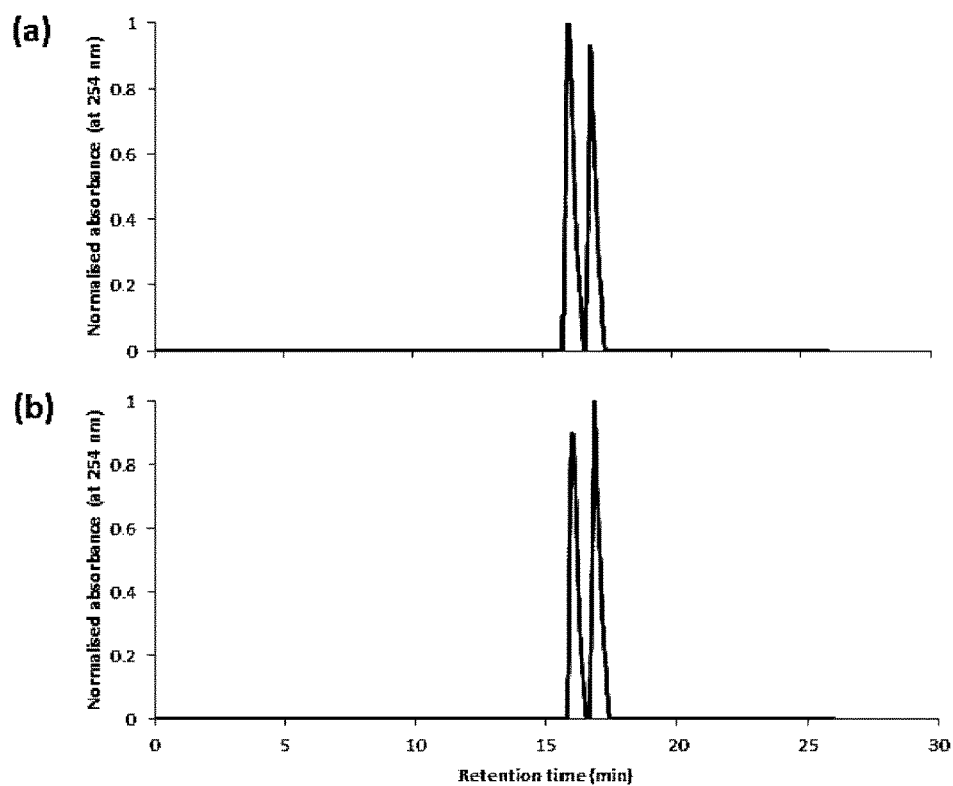
FIG. 9 is the reverse-phase analytical HPLC chromatogram of the isolated fractions identified as PhAs(LHP). (a) Fraction 1: PhAs(LHP) eluted at 15.97 and 16.85 min (b) Fraction 2: PhAs(LHP) eluted at 15.97 and 16.87 min, demonstrating the spontaneous interconversion of the two isomers.

The resulting compounds (isolated and dried) from each fraction were dissolved in MilliQ water (3 mM) and re-examined by analytical HPLC. In each case the HPLC chromatogram (FIG. 9) confirmed the presence of two peaks, as had previously been observed in the initial preparatory HPLC chromatogram. The elution times were consistent with the elution of PhAs(LHP). This indicates that there are spontaneously converting isomers of PhAs(LHP) and is consistent with a chiral centre at the As atom which is bound to three different moieties (the phenyl group and the two asymmetric ends of the peptide) and contains a lone pair. This is indicated below wherein (a) is the R isomer and (b) is the S isomer.

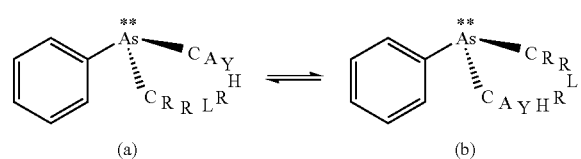

(a)        (b)

Stability Studies of as-LHP Complexes

Method

The stability of As-LHP complexes was studied by XAS. Samples were prepared by dissolving HyAs(LHP), MeAs(LHP) or PhAs(LHP) (1.5 mM) in Milli-Q water which was maintained at 37° C. Immediately prior to analysis the arsenic-peptide solution (600 μL) was mixed with ethylene glycol (300 μL) to prevent crystallisation during rapid freezing. The resultant solution (1 mM final As concentration) was transferred by syringe to the sample holder which was sealed with Kapton tape. The sample was then rapidly submerged in liquid nitrogen and transferred to the liquid helium cryostat where it was analysed at 10° K.

Arsenic K-edge XAS data were collected at the Australian National Beamline Facility (ANBF, beamline 20B) KEK, Tsukuba, Japan with a beam energy of 2.5 GeV, and beam current of 300-400 mA. A Si[111] channel-cut monochromator was detuned by 50% to reject harmonics. All spectra were recorded in fluorescence mode at ~10° K (maintained with a closed-cycle He CryoIndustries REF-1577-D22 cryostat) using a 36-element Ge-array detector (Eurisys/Canberra Industries) and a 1-mm vertical slit width. XAS spectra were obtained at the zero time point and then at a later time point, 4 h or 14 h. The spectra from the two time points were processed and analysed using EXAFS PAK.

The stability of the two most promising As-LHP complexes was also studied in cell medium (IMDM). Samples were prepared by dissolving MeAs(LHP) or PhAs(LHP) (1.5 mM) in IMDM which was maintained at 37° C. The same protocol was followed as that for the Milli-Q water stability studies. XAS spectra were obtained at the zero time point and then at 24 h. As with the Milli-Q water samples, the spectra from the two time points were processed, fitted and quantified using EXAFSPAK.

Results

FIG. 10 shows the comparison of the spectra obtained for two time points (0 h, blue, and 4 h, red) of HyAs(LHP) in Milli-Q water. The spectrum for the 4-h sample is clearly different to that obtained for the 0-h sample indicating that the complex is not stable in Milli-Q water for 4 h. The spectrum for the 4-h sample is similar to that obtained for arsenite in Milli-Q water suggesting that the LHP is no longer bound to arsenic. The shift in the edge is indicative of arsenic bound to oxygen atoms rather than sulfur atoms (the latter would be the case for the intact HyAs(LHP) complex).

Figure 11:
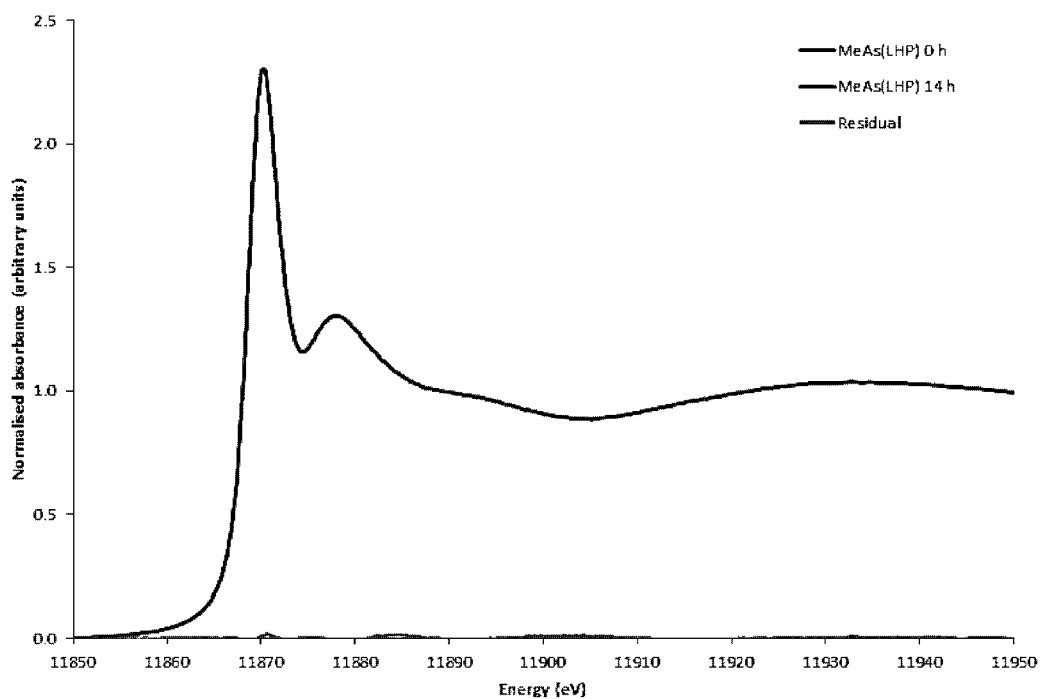
FIG. 11 is the As K-edge XANES spectra for MeAs(LHP) in Milli-Q water at 0 h (blue, not visible due to overlap with 14-h spectrum) and 14 h (red) showing good stability over this time period. The residual between the two spectra is depicted in green.

FIG. 11 depicts the spectra obtained for two time points (0 h, blue, and 14 h, red) of MeAs(LHP) in Milli-Q water. The two spectra were 93% comparable with the residual plotted in green depicting the small anomalies between the two spectra.

Figure 12:
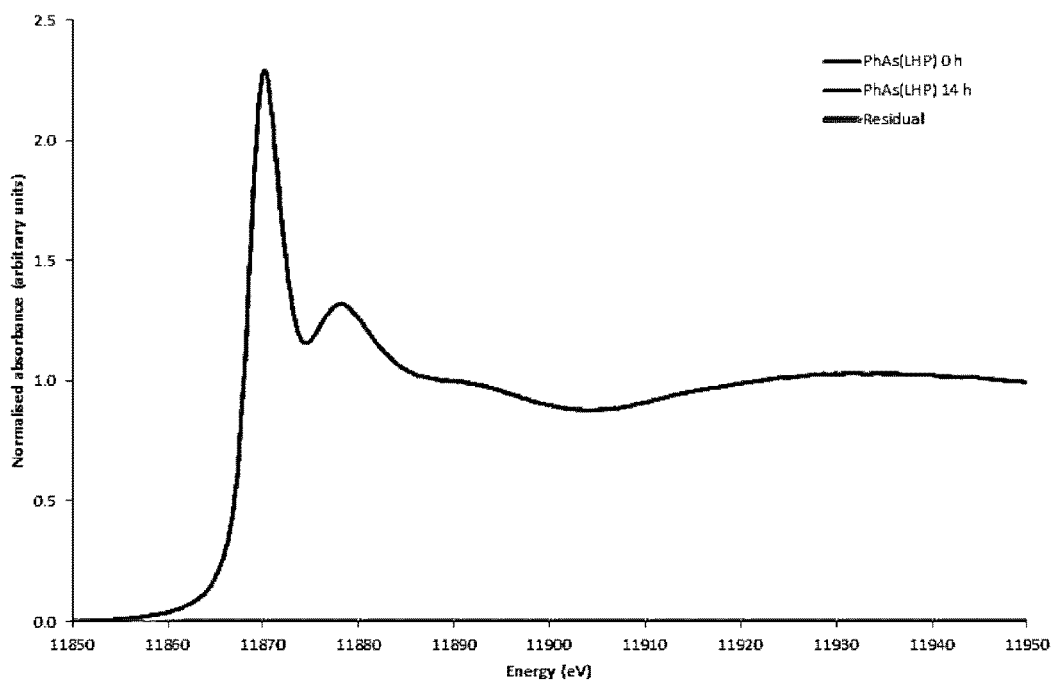
FIG. 12 is the As K-edge XANES spectra for PhAs(LHP) in Milli-Q water at 0 h (blue, not visible due to overlap with 14-h spectrum) and 14 h (red) showing excellent stability over this time period. The residual between the two spectra is depicted in green.

FIG. 12 shows the comparison of the spectra obtained for two time points (0 h, blue, and 14 h, red) of PhAs(LHP) in Milli-Q water. The agreement between the two spectra is close to 100%, with the residual, very close to zero throughout, exhibiting no significant residual features. This indicates that the PhAs(LHP) complex is stable in Milli-Q water for 14 h.

Figure 13:
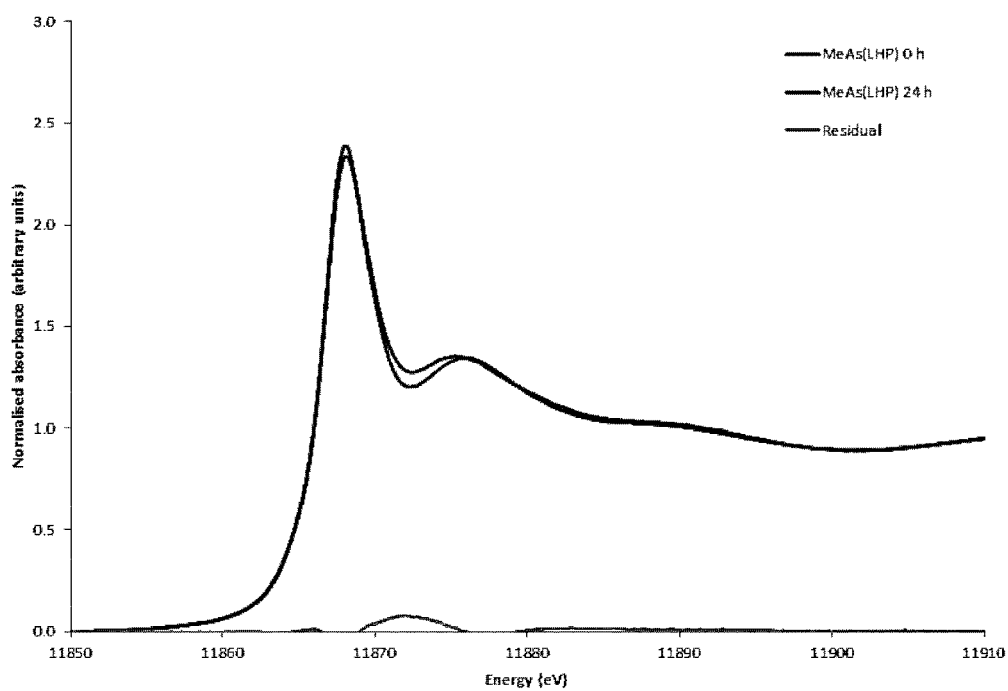
FIG. 13 is the As K-edge XANES spectra for MeAs(LHP) in IMDM (cell medium) at 0 h (blue, slightly higher peak and lower trough of overlapping traces) and 24 h (red) showing reasonable stability over this time period. The residual between the two spectra (green), shows anomalies between the two spectra particularly in the region of the post-edge trough.

FIG. 13 depicts the spectra obtained for two time points (0 h, blue, and 24 h, red) of MeAs(LHP) in IMDM (cell medium). The two spectra were 82% comparable with the residual plotted in green depicting the anomalies between the two spectra. The most significant change can be clearly seen in a reduction in the post edge trough.

Figure 14:
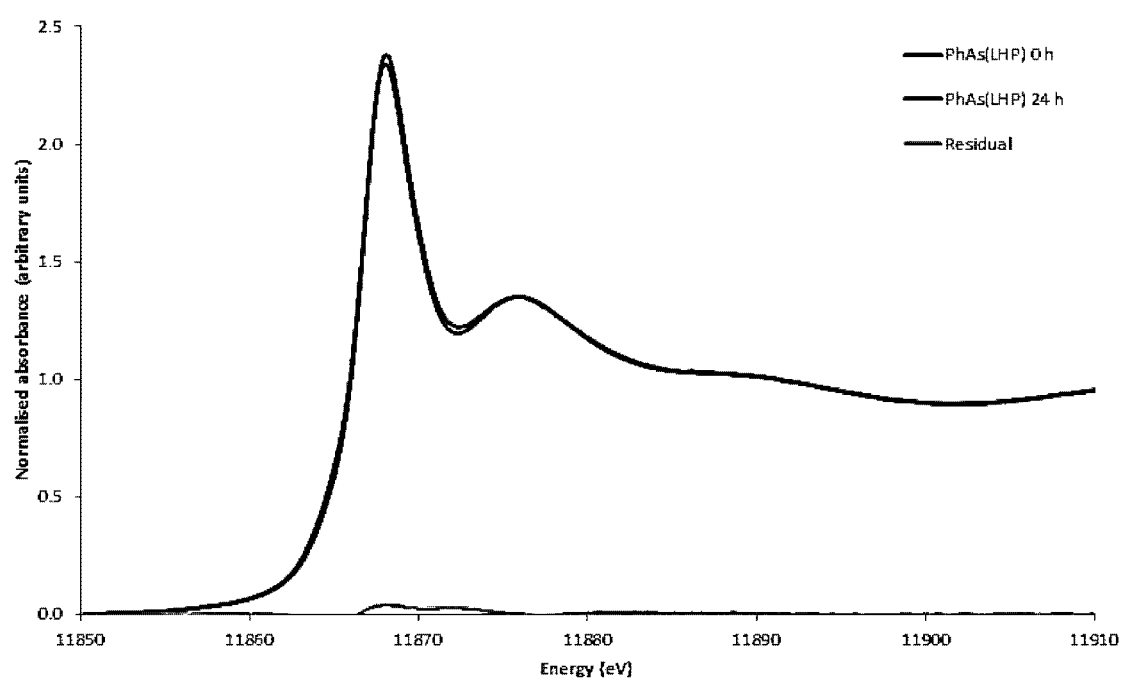
FIG. 14 is the As K-edge XANES spectra for PhAs(LHP) in IMDM at 0 h (blue, only slightly visible due to overlap with 24-h spectrum, slightly lower peak and lower trough of overlapping traces) and 24 h (red) showing good stability over this time period. The residual between the two spectra is depicted in green.

FIG. 14 shows the comparison of the spectra obtained for two time points (0 h, blue, and 24 h, red) of PhAs(LHP) in IMDM (cell medium). The agreement between the two spectra is 97% with the residual (green), containing minor residual features. This indicates that the PhAs(LHP) complex is reasonably stable in IMDM for 24 h.

Cytotoxicity (MTT) Testing of As(LHP) Complexes

Methods

Cell Lines and Culture Procedures

All cell culturing and cell assays were performed in a biological safety cabinet (class II, Email Westinghouse Pty Ltd) using sterile technique.

Human Chronic Myeloid Leukemia (K562) Cells

K562 cells are human chronic myeloid leukemia cells/bone marrow cells derived from a 53 year old female, originally obtained from the ATCC. This cell line was chosen as it is a target of LHP and so, potentially, the As-LHP complexes. Toxicity and $IC_{50}$ values were established for arsenite, $AsI_3$, PAO, LHP, HyAs(LHP), MeAs(LHP), PhAs(LHP), acetarsol, ATO, sLHP, and PhAs(sLHP) using the MTT assay.

K562 cells were grown from semi-permanents (purchased from ATCC). The cells were grown in growth medium (GM) containing IMDM (Iscove's modified Dulbecco's Medium, Invitrogen, 500 mL), Fetal bovine serum (FBS, Bovogen, Thermo Scientific, 10% v/v) and penicillin/streptomycin (Gibco, Life Technologies, 10 mL/500 mL IMDM, 200 IU/mL and 200 µg/mL respectively). K562 cultures were grown in cell culture flasks (Greiner) with 75 cm$^2$ surface area, at 37° C. in a 5% $CO_2$ incubator (Heraeus, Thermo Scientific, USA). The cells were subcultured, typically twice a week. The cell suspension was centrifuged (1500 rpm, 5 mins, Heraeus Labofuge 300), the pellet resuspended in GM (5 mL) and 2 drops were added to GM (25 mL) in the cell culture flask.

Human Acute Promyelocytic Leukemia (HL-60) Cells

HL-60 cells are human acute promyelocytic leukemia cells derived from a 36-year-old Caucasian female with acute promyelocytic leukemia. HL-60 cells were grown from semi-permanents (originally purchased from ATCC). These APL cells are another leukemia cell line known to be targeted by the CAYHRLRRC peptide and represent the condition currently treated with As therapy, namely ATO. The cells were grown in growth medium (GMH) containing IMDM (500 mL), FBS (20% v/v) and penicillin/streptomycin (10 mL/500 mL IMDM, 200 IU/mL and 200 µg/mL, respectively). The cells were subcultured, typically twice a week in the same manner as the K562 cells using GMH.

Human Acute Myeloblastic Leukemia (Kasumi-1) Cells

Kasumi-1 cells were purchased from CellBank Australia. Kasumi-1 cells are human acute myeloblastic leukemia cells/bone marrow cells derived from a 7 year old Japanese male. This cell line was chosen to explore the potential of PhAs(LHP) as a treatment for AML. The Kasumi-1 cells were grown in growth medium (GM1) containing RPMI-1640 (Roswell Park Memorial Institute Medium, Invitrogen, 500 mL), FBS (20% v/v) and penicillin/streptomycin (10 mL/500 mL IMDM, 200 IU/mL and 200 µg/mL respectively). Kasumi-1 cells were grown in cell culture flasks with 75 cm$^2$ surface area, at 37° C. in a 5% $CO_2$ incubator. The cells were subcultured, typically twice a week. Briefly, half the cell suspension was replaced with fresh GM1 to maintain the cell density between $3 \times 10^5$ and $3 \times 10^6$ cells/mL.

Human T-Cell Leukemia (KARPAS 45) Cells

KARPAS 45 cells are human T-cell leukemia cells/bone marrow cells derived from a 2-year old male prior to therapy, and were grown from semi-permanents (purchased from CellBank Australia) in growth medium (GMK) containing RPMI-1640, FBS (20% v/v), Glutamine (2 mM, Gibco, Life Technologies) and penicillin/streptomycin (10 mL/500 mL IMDM, 200 IU/mL and 200 µg/mL respectively). KARPAS 45 cultures were grown in cell culture flasks with 75 cm$^2$ surface area, at 37° C. in a 5% $CO_2$ incubator. The cells were subcultured, typically twice a week by replacing half the volume with fresh GMK.

Human Liver Cancer (HepG2) Cells

HepG2 cells are human liver carcinoma cells derived from a 15 year old Caucasian male. They are adherent, epithelial-like cells and were grown from semi-permanents (originally purchased from ATCC). The cells were grown in growth medium (GMA) containing DMEM (Dulbecco's modified Eagle's Medium, Life Technologies, 500 mL), FBS (50 mL, 10% v/v) and penicillin/streptomycin (10 mL, 200 IU/mL and 200 µg/mL, respectively). The cells were subcultured, typically twice a week, before reaching confluence. The cell medium was removed, discarded and the cells rinsed with PBS, which was then also removed and discarded. Trypsin (5 mL, 0.25% w/v in PBS, Gibco, Life Technologies) was added and the flask was incubated until the cells had detached. GMA (5 mL) was added to the flask and the contents of the flask were transferred to a sterile tube and centrifuged (1500 rpm, 5 mins). Following removal of the supernatant, the pellet was resuspended in GMA (5 mL) and 1-2 drops of the cell solution was added to GMA (25 mL) in the cell culture flask.

A549 Human Lung Cancer Cells

A549 cells are human lung carcinoma cells derived from a 58 yr old male. They are adherent epithelial-like cells and were grown from semi permanents purchased from CellBank Australia. The cells were grown and subcultured in the same manner as for the HepG2 cells, above. These cells were also chosen to represent fast-growing cells derived from a solid tumour that should not be recognised or targeted by the As-peptide complex.

Chinese Hamster Solid Tumour Cells

Chinese hamster (CH) solid tumour cells were chosen as a non-human cell line (which should not be targeted). They are adherent epithelial-like cells, and were grown from semi-permanents. The cells were grown and subcultured in the same manner as for the HepG2 cells, above.

Human Peripheral Blood Mononuclear Cells (hPBMC)

Blood (40 mL) was drawn from a healthy volunteer. Sterile PBS (15 mL) was added to 20 mL of blood. Each tube was inverted 3-4 times to mix. The blood was underlaid with approximately 15 mL Ficoll-Paque™ PLUS (GE Healthcare) and centrifuged (1700 rpm, Heraeus Labofuge 400 R centrifuge) for 30 mins (brake off). The mononuclear cell layer was transferred to new tubes and washed twice with sterile PBS (50 mL). The tubes were gently inverted to mix and then centrifuged (1500 rpm, 15 min). The mononuclear cells were resuspended in PBS (equivalent to the original blood volume) and counted with a haemocytometer. Following centrifugation, the cells were resuspended in sufficient RPMI-1640 to produce the required cell population. A calibration assay was performed and it was determined that $10^6$ cells/well produced the optimal absorbance (1.00-2.00) for the MTT assay controls using hPBMC.

MTT Cytotoxicity Assays

The cytotoxicities of the compounds were assessed by adaptations of the MTT assay described by Carmichael et al. (Cancer Res. 1987, 47, 936) and Mosman (J. Immunol. Methods 1983, 65, 55). The MTT assay is based on the conversion of a tetrazolium salt, into formazan by living cells and allows the cell survival to be quantified via colourimetric assessment. This assay establishes an $IC_{50}$ for each compound to enable comparison of toxicities of different compounds toward the cell line employed in the assay.

This assay was used to compare the toxicities of the arsenic peptide complexes with other arsenic compounds in order to examine their targeting ability and potential as anti-leukemia treatments. The cytotoxicities of the two isomers of PhAs (LHP) were assessed on K562 and HL-60 cells by the MTT assay, as previously described. Treatment solutions were freshly prepared in IMDM immediately prior to treatment and were serially diluted.

Cytotoxicity assays were performed testing various concentration ranges of sodium arsenite (arsenite, Sigma Aldrich), phenylarsine oxide (PAO, Sigma Aldrich), Ask, acetarsol (acetarsone, Sigma Aldrich), ATO (Phenasen formulation obtained from Phebra), scrambled LHP (sLHP), LHP (both obtained from Peptide 2.0, USA), PhAs(LHP) and PhAs(sLHP).

Protocol for MTT Cytotoxicity Assays on K562 Cells

K-562 cells ($8 \times 10^5$ cells) were seeded in growth medium (5 mL) in 60-mm cell culture dishes and incubated at 37° C., 5% $CO_2$ for 24 h. The compounds tested were arsenite, $AsI_3$, ATO, Acetarsol, LHP, HyAs(LHP), MeAs(LHP), PhAs (LHP), sLHP and PhAs(sLHP). Treatment solutions were freshly prepared in IMDM immediately prior to treatment. Compounds were serially diluted in IMDM to achieve a range of concentrations for analysis. The cell suspension from each dish was centrifuged (1200 rpm, 5 min, Heraeus Labofuge 300) and the pellets were resuspended in treatment solutions (3 mL) or, in the instance of control cells, IMDM (3 mL), and returned to the dishes for incubation (37° C., 5% $CO_2$). After 24 h the cell solutions were centrifuged (1200 rpm, 5 min). The cells were washed twice by addition of sterile PBS followed by centrifugation (1200 rpm, 5 min). The cells were resuspended in IMDM (5 mL) and returned to fresh dishes. MTT (400 µL, 2 mg/mL, IMDM) was added to each dish and the dishes were incubated. After 4 h the solutions were centrifuged (1200 rpm, 5 min) and DMSO (1.8 mL) was added to the pellets to dissolve the formazan crystals. Each solution was pipetted (200 µL/well) into a 96-well plate (1 tube/column, Cellstar, Greiner Bio-one, Australia).

Protocol for MTT Cytotoxicity Assays on HL-60 Cells

The compounds tested included: arsenite, ATO, Acetarsol, LHP, PhAs(LHP), sLHP and PhAs(sLHP). Due to the expense of the peptide and the improved stability of the PhAs(LHP) complex over HyAs(LHP) and MeAs(LHP), it was decided to discontinue testing the latter two complexes. Treatment solutions were freshly prepared in IMDM immediately prior to treatment. Compounds were serially diluted in IMDM to achieve a range of concentrations for analysis. Due to the loss of cells through transfer between dishes and tubes, an alternative MTT protocol by Tada et al. (*J. Immunol. Methods* 1986, 93, 157) was initially trialled with K562 cells. As it was determined that the resultant $IC_{50}$ values were comparable with the previous method, the new protocol was used for the MTT assays conducted with HL-60 cells. HL-60 cell solution ($2 \times 10^5$ cells/50 µL, IMDM) was added to each well (rows 2-7, columns B-I, 96 well flat bottom plate, Greiner). The treatment solutions (50 µL) were then added to each of the wells in columns 3-11 (most dilute in column 3, most concentrated in column 11), while IMDM (50 µL) was added to the control wells (Column 2). The plates were incubated (37° C., 5% $CO_2$) for 24 h, after which MTT solution (20 µL, 5 mg/mL, IMDM) was added to each well and the plates were returned to the incubator to allow for formazan development. After 4 h, solubilising solution (100 µL, 10% SDS in 0.01 M HCL) was added to each well and the plates were incubated overnight.

Protocol for MTT Cytotoxicity Assays on Kasumi-1 Cells

Kasumi-1 cells were seeded at a density of $2 \times 10^5$ cells/well. Compounds assessed included: sodium meta arsenite (arsenite, Sigma Aldrich), arsenic trioxide (ATO, Phebra), phenylarsine oxide (PAO, Sigma Aldrich), the leukemia homing peptide (LHP) and the scrambled leukemia homing peptide (sLHP) obtained from Peptide 2.0, USA; and PhAs (LHP) and PhAs(sLHP), which were synthesised, purified and characterised. Treatment solutions were freshly prepared in RPMI-1640 immediately prior to treatment. Compounds were serially diluted in RPMI-1640 to achieve a range of concentrations for analysis. MTT assays were performed, in the same manner as the HL-60 cells, at least 3 times to obtain a mean and standard deviation for the $IC_{50}$ values.

Protocol for MTT Cytotoxicity Assays on KARPAS 45 Cells

Treatment solutions were freshly prepared in RPMI-1640 immediately prior to treatment and compounds were serially diluted in RPMI-1640 to achieve a range of concentrations for analysis. The compounds tested were arsenite, ATO, Acetarsol, LHP, PhAs(LHP), sLHP and PhAs(sLHP). KARPAS 45 cell solution ($6 \times 10^5$ cells/50 µL, RPMI-1640) was added to each well (rows 2-4, columns B-I, 96 well flat bottom plate, Greiner). The treatment solutions (50 µL) were added to each of the wells in columns 3-11 (most dilute in column 3, most concentrated in column 11), while RPMI-1640 (50 µL) was added to the control wells (Column 2). The rest of the assay was conducted in the same manner as that for HL-60 cells outlined in the previous paragraph with the exception that the MTT solution was prepared in RPMI-1640.

Protocol for MTT Cytotoxicity Assays on HepG2, A549 and Chinese Hamster Solid Tumour Cells The cell solution ($1 \times 10^4$ cells/100 µL GMA) was added to each well (rows 2-7, columns B-I, 96 well flat bottom plate, Greiner) and incubated for 24 h. GMA was removed and freshly prepared treatment solutions (100 µL, compounds serially diluted in DMEM) were added to each of the wells in columns 3-11 (most dilute in column 3, most concentrated in column 11), while DMEM (100 µL) was added to the control wells (Column 2). The compounds tested were arsenite, ATO, PAO, Acetarsol, LHP, and PhAs(LHP). The rest of the assay was carried out using the same protocol as that used for the HL-60 cells with the exception that the MTT solution was prepared using DMEM.

Protocol for MTT Cytotoxicity Assays on hPBMC

Treatment solutions were freshly prepared on the day of treatment in the same manner as for HL-60 cells. The compounds tested were arsenite, ATO, PAO, acetarsol, LHP, and PhAs(LHP). The hPBMC cell solution ($1 \times 10^6$ cells/50 µL, RPMI-1640) was added to each well (rows 2-4, columns B-I, 96 well flat bottom plate, Greiner) and the rest of the assay was carried out using the same protocol as that for the HL-60 cells.

MTT Colourimetric Assessment and $IC_{50}$ Calculations

Colourimetric assessment and calculations for assays on K562 cells

The absorbance was measured at 570 nm and 630 nm (BMG LabTech Polarstar Omega microplate reader). The percentage of cell survival was then determined by Equation 1.

$$\text{Cell survival}(\%) = \frac{A_{५-0} - A_{650}(\text{treated cells})}{A_{५-0} - A_{650}(\text{control cells})} \times 100 \qquad \text{Equation 1}$$

The calculated cell viability was plotted against the treatment concentrations to determine the $IC_{50}$ value of each species. All MTT assays were performed at least 3 times to provide the necessary power required to perform statistical analysis. Statistical analyses were performed using one-way ANOVA and Tukey's multiple comparison test (GraphPad Prism).

Colourimetric Assessment and Calculations for Assays on HL-60, Kasumi-1, KARPAS 45, HepG2, A549, CH Solid Tumour Cells and hPBMC, Absorbance readings were recorded at 570 nm and 690 nm (BMG LabTech Polarstar Omega microplate reader) and concentration-response curves (using Equation 2 to calculate cell viability) were produced in order to calculate the $IC_{50}$ value for each compound. MTT assays were performed at least 3 times, unless otherwise stated. Statistical analyses were performed using one-way ANOVA and Tukey's multiple comparison test (GraphPad Prism).

$$\text{Cell survival}(\%) = \frac{A_{5-0} - A_{690}(\text{treated cells})}{A_{5-0} - A_{690}(\text{control cells})} \times 100 \quad \text{Equation 2}$$

Results

MTT Results and $IC_{50}$ Values for Isomers of PhAs(LHP) Towards K562 and HL60 Cells $IC_{50}$ values obtained from MTT cell cytotoxicity studies of the PhAs(LHP) isomer fractions on both K562 and HL-60 cells indicated that the products resulting from each HPLC fraction exhibit the same toxicities (Table 14).

TABLE 14

$IC_{50}$ values obtained from MTT cytotoxicity assays of the two compounds resulting from the fractions identified as PhAs(LHP).

| Cell line | Fraction 1 $IC_{50}$ value (µM)* | Fraction 2 $IC_{50}$ value (µM)* |
|---|---|---|
| K562 | 0.47 ± 0.02 | 0.48 ± 0.04 |
| HL-60 | 0.64 ± 0.02 | 0.63 ± 0.03 |

*Results are presented as the mean and standard deviation of three assays.

As it was evident that racemisation occurred at room temperature and above, and that this did not effect the biological activity, all further testing was performed on the racemic mixture (unresolved isomer fractions).

MTT Results and $IC_{50}$ Values for K562 Cells

Figure 15:
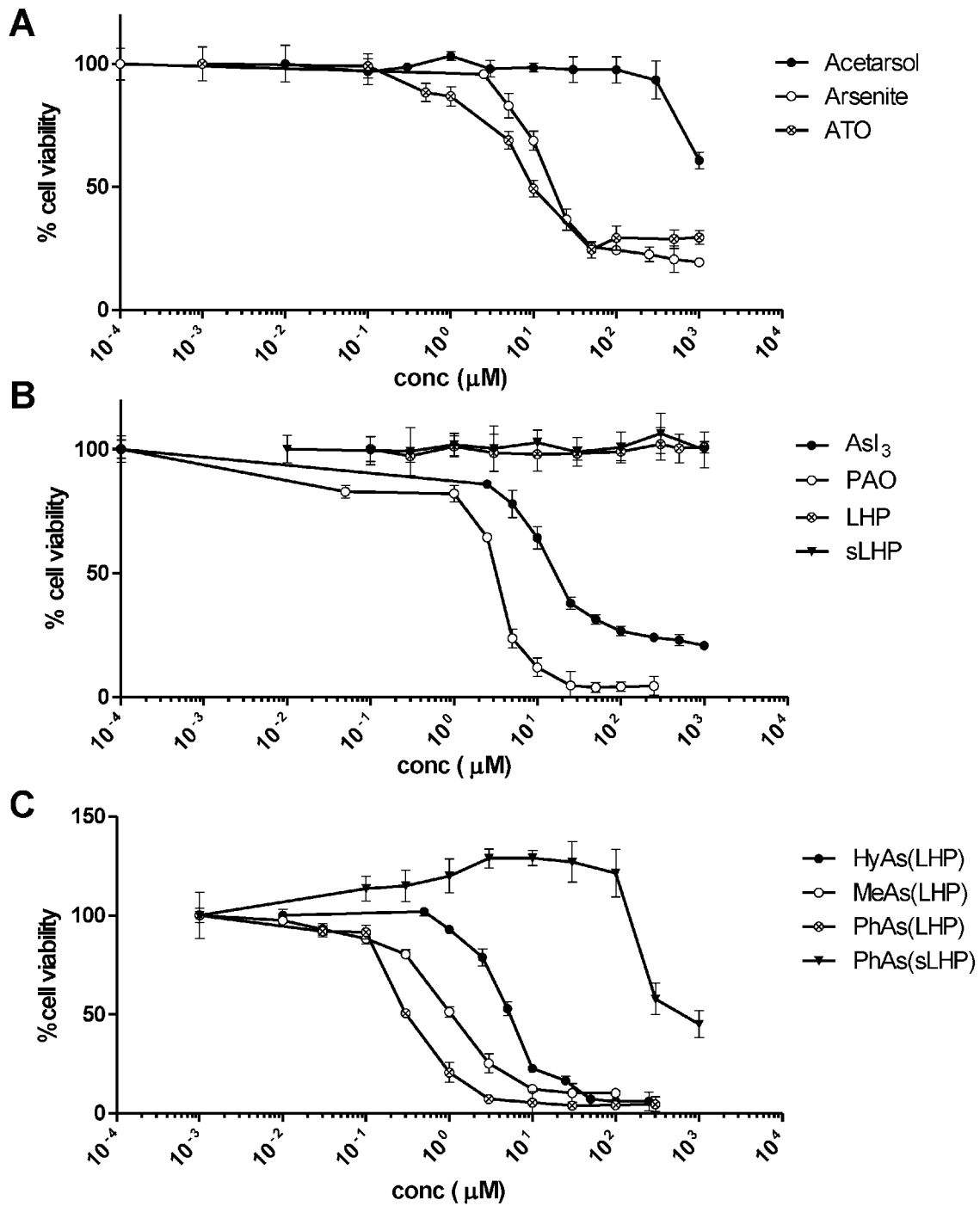
FIG. 15 is a series of concentration-response curves produced for MTT assays on K562 cells following 24-h treatment. Compounds tested included: (A) Current arsenic drugs: Acetarsol, arsenite, ATO, (B) Starting materials and peptides: Ask, PAO, LHP, sLHP, (C) Arsenic peptides: HyAs(LHP), MeAs(LHP), PhAs(LHP), and PhAs(sLHP); These curves are used to calculate the $IC_{50}$ for each compound whereby a lower $IC_{50}$ indicates a more toxic compound.
Figure 16:
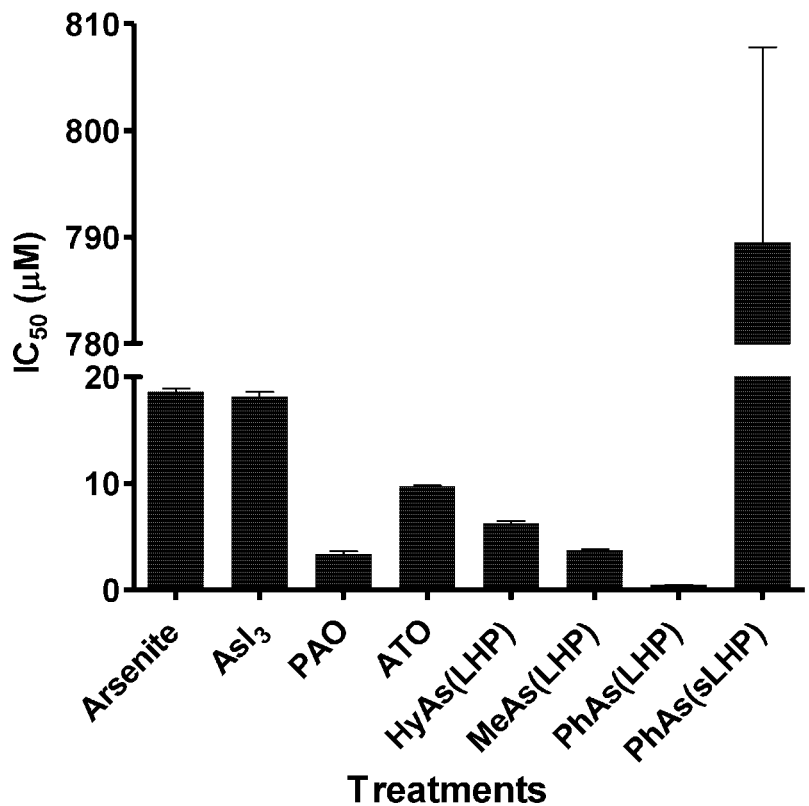
FIG. 16 shows the results of a comparison of $IC_{50}$ values of the specified As compounds obtained from MTT assays on K562 cells following 24-h treatment, showing the improved toxicity of the arsenic peptide complexes.

The concentration-response curves resulting from the MTT assays on K562 cells following a 24-h treatment are depicted in FIG. 15. Arsenic treatment, resulting in cell death, produced typical concentration-response curves for the majority of the compounds tested. The $IC_{50}$ values obtained for arsenite, $AsI_3$, ATO, PAO, HyAs(LHP), MeAs(LHP), PhAs(LHP) and PhAs(sLHP) on K562 cells following 24-h treatments are shown in FIG. 16 and table 15. The $IC_{50}$ values for arsenite and $AsI_3$ were very similar (18.63±0.49 µM and 18.14±0.75 µM, respectively). ATO treatment produced an $IC_{50}$ value of 9.74±0.16 µM, approximately half that of arsenite ($NaAsO_2$) which is consistent with ATO containing twice the arsenic atoms as arsenite. PAO ($IC_{50}$: 3.40±0.42 µM) was three times more toxic than ATO indicating that there is possibly greater uptake of this compound due to the increased lipophilicity associated with the presence of the phenyl group. Alternatively, the phenyl may be directly involved in the interaction with the cell target.

TABLE 15

The $IC_{50}$ values obtained from triplicate MTT assays following 24-h treatment of K562 cells.

| Treatment | $IC_{50}$ (PM) |
|---|---|
| Arsenite | 18.63 ± 0.49 |
| $AsI_3$ | 18.14 ± 0.75 |
| ATO | 9.74 ± 0.16 |
| PAO | 3.40 ± 0.42 |
| HyAs(LHP) | 6.21 ± 0.47 |
| MeAs(LHP) | 3.74 ± 0.17 |
| PhAs(LHP) | 0.487 ± 0.025 |
| PhAs(sLHP) | 790 ± 32 |

It is noteworthy that HyAs(LHP) treatment produced an 1050 (6.21±0.47 µM) that was 60% of that for ATO even though it contains half the number of arsenic atoms than ATO. This suggests that the presence of the peptide may contribute to the uptake of HyAs(LHP); however, the poorer stability of the complex is most likely influencing the toxicity. The $IC_{50}$ value obtained for MeAs(LHP) ($IC_{50}$: 3.74±0.17 µM) was 60% that of HyAs(LHP) and 37% that of ATO which could be attributed to the extra stability of this compound due to the presence of the methyl group on the arsenic. PhAs(LHP) proved to be the most toxic compound tested (ICH: 0.487±0.025 µM). The presence of the phenyl ring also increases the stability of this complex. It was twenty times more toxic than ATO and seven times more toxic than PAO. Interestingly the arsenic compound with the scrambled peptide (PhAs(sLHP), $IC_{50}$: 790±32 µM) proved to be 1600 times less toxic than PhAs(LHP) in the K562 cells indicating that the peptide configuration plays an important role in the toxicity of PhAs(LHP) toward K562 cells.

Acetarsol, was tested up to 1000 µM and failed to produce 50% inhibition with 60.5% of K562 cells still viable at this high concentration. At 1000 µM, acetarsol turned the solution acidic (the medium turned yellow, pH 6.87) so it is highly likely that the low pH is contributing to the reduction in the cell number rather than the compound itself. Due to the pH changes, higher concentrations were not tested to establish an $IC_{50}$. LHP and sLHP were non-toxic up to 1000 µM on K562 cells, and therefore cannot be contributing to the toxicity displayed by the As(LHP) complexes. The cell viability for both of these compounds remained close to or above 100% in all MTT assays.

The established $IC_{50}$ values for each compound were statistically compared. The value for PhAs(sLHP) was statistically higher than all other compounds (P<0.0001). Due to the large $IC_{50}$ value and corresponding standard deviation for PhAs(sLHP) the results of this compound were omitted from the statistical comparisons between the $IC_{50}$ values of the other compounds. Table 16 contains the statistical analysis results.

The $IC_{50}$ values for arsenite and A513 were not statistically different from each other. Similarly, the values obtained for PAO and MeAs(LHP) were not statistically different. Importantly the analysis showed that the differences between the $IC_{50}$ values for all the other compounds were statistically significant (P<0.0001).

TABLE 16

Results of the statistical analysis comparing the $IC_{50}$ values obtained from MTT assays following 24-h treatment of K562 cells.

| Tukey's Multiple Comparison Test | Mean Difference | Q | Significant | P |
|---|---|---|---|---|
| Arsenite vs AsI₃ | 0.4867 | 1.997 | No | Ns |
| Arsenite vs PAO | 15.23 | 62.50 | Yes | <0.0001 |
| Arsenite vs ATO | 8.887 | 36.46 | Yes | <0.0001 |
| Arsenite vs HyAs(LHP) | 12.42 | 50.96 | Yes | <0.0001 |
| Arsenite vs MeAs(LHP) | 14.89 | 61.10 | Yes | <0.0001 |
| Arsenite vs PhAs(LHP) | 18.14 | 74.45 | Yes | <0.0001 |
| AsI₃ vs PAO | 14.75 | 60.51 | Yes | <0.0001 |
| AsI₃ vs ATO | 8.400 | 34.47 | Yes | <0.0001 |
| AsI₃ vs HyAs(LHP) | 11.93 | 48.96 | Yes | <0.0001 |
| AsI₃ vs MeAs(LHP) | 14.40 | 59.10 | Yes | <0.0001 |
| AsI₃ vs PhAs(LHP) | 17.66 | 72.45 | Yes | <0.0001 |
| PAO vs ATO | −6.347 | 26.04 | Yes | <0.0001 |
| PAO vs HyAs(LHP) | −2.813 | 11.54 | Yes | <0.0001 |
| PAO vs MeAs(LHP) | −0.3433 | 1.409 | No | Ns |
| PAO vs PhAs(LHP) | 2.910 | 11.94 | Yes | <0.0001 |
| ATO vs HyAs(LHP) | 3.533 | 14.50 | Yes | <0.0001 |
| ATO vs MeAs(LHP) | 6.003 | 24.63 | Yes | <0.0001 |
| ATO vs PhAs(LHP) | 9.257 | 37.98 | Yes | <0.0001 |
| HyAs(LHP) vs MeAs(LHP) | 2.470 | 10.13 | Yes | <0.0001 |
| HyAs(LHP) vs PhAs(LHP) | 5.723 | 23.48 | Yes | <0.0001 |
| MeAs(LHP) vs PhAs(LHP) | 3.253 | 13.35 | Yes | <0.0001 |

MTT Results and $IC_{50}$ Values for HL-60 Cells

Figure 17:
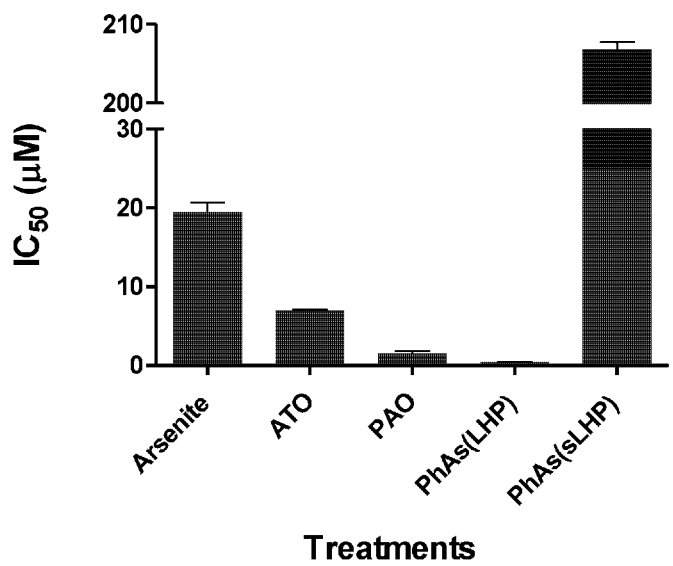
FIG. 17 is a representation of the results of a comparison of $IC_{50}$ values of the specified As compounds obtained from MTT assays on HL-60 cells following 24-h treatment, showing good toxicity of PhAs(LHP) which contains the targeting peptide and the greatly reduced toxicity of PhAs (sLHP) which contains the scrambled peptide (no longer targeting)

The $IC_{50}$ values obtained for arsenite, ATO, PAO, PhAs(LHP) and PhAs(sLHP) in HL-60 cells following a 24-h treatment are shown in FIG. 17. ATO produced an $IC_{50}$ value (7.0±0.1 µM), a little less than half that obtained for arsenite (20±1 µM) which is consistent with ATO containing double the number of arsenic atoms as arsenite. The fact that it is not exactly half suggests that the anion acts via a different mode in the two cell lines; either by a different uptake mechanism or mode of action for toxicity. The $IC_{50}$ value obtained for PAO (1.5±0.3 µM) is approximately a thirteenth that for arsenite and about a quarter of the $IC_{50}$ value of ATO. The compound of interest, PhAs(LHP), with an $IC_{50}$ value of 0.5±0.1 µM, showed three times greater toxicity toward HL-60 cells than the PAO starting material implying that the presence of LHP may be aiding the uptake and/or toxicity in these cells. This is again supported by the result for the scrambled peptide compound, PhAs(sLHP), which exhibited an $IC_{50}$ value of 205±4 µM, one hundred and thirty times that of PAO and over four hundred times that of PhAs(LHP). The large $IC_{50}$ suggests that the extra bulk of the scrambled peptide most likely impedes uptake and, therefore, hinders cytotoxic activity. Uptake assays were conducted to further explore these results.

The peptides, LHP and sLHP, were tested but were not toxic up to 1000 µM with the cell viability remaining close to 100% throughout the concentration ranges tested. Acetarsol, tested up to 1000 µM, failed to induce toxicity required to obtain an $IC_{50}$ value.

The $IC_{50}$ values for each compound were statistically compared across the group and not surprisingly, the value for PhAs(sLHP) was statistically different to all the other arsenic compounds assayed (P<0.0001). Due to the large $IC_{50}$ value for PhAs(sLHP) the results of this compound were omitted from further statistical analyses for the other compounds. Importantly the analysis showed that the differences between most results were statistically significant as listed in Table 17. It was found that the $IC_{50}$ value for arsenite was significantly different from all the other compounds tested (P<0.0001 for all other compounds). ATO was also found to be significantly different to all other compounds (P<0.0001) but PAO was not deemed significantly different to PhAs(LHP).

TABLE 17

Results of the statistical analysis comparing the $IC_{50}$ values obtained from MTT assays following 24-h treatment of HL-60 cells.

| Tukey's Multiple Comparison Test | Mean Difference | Q | Significant | P |
|---|---|---|---|---|
| Arsenite vs ATO | 12.56 | 35.90 | Yes | <0.0001 |
| Arsenite vs PAO | 18.01 | 51.46 | Yes | <0.0001 |
| Arsenite vs PhAs(LHP) | 19.03 | 54.39 | Yes | <0.0001 |
| ATO vs PAO | 5.444 | 15.56 | Yes | <0.0001 |
| ATO vs PhAs(LHP) | 6.472 | 18.49 | Yes | <0.0001 |
| PAO vs PhAs(LHP) | 1.028 | 2.937 | No | ns |

MTT Results and $IC_{50}$ Values for Kasumi-1 Cells

Figure 18:
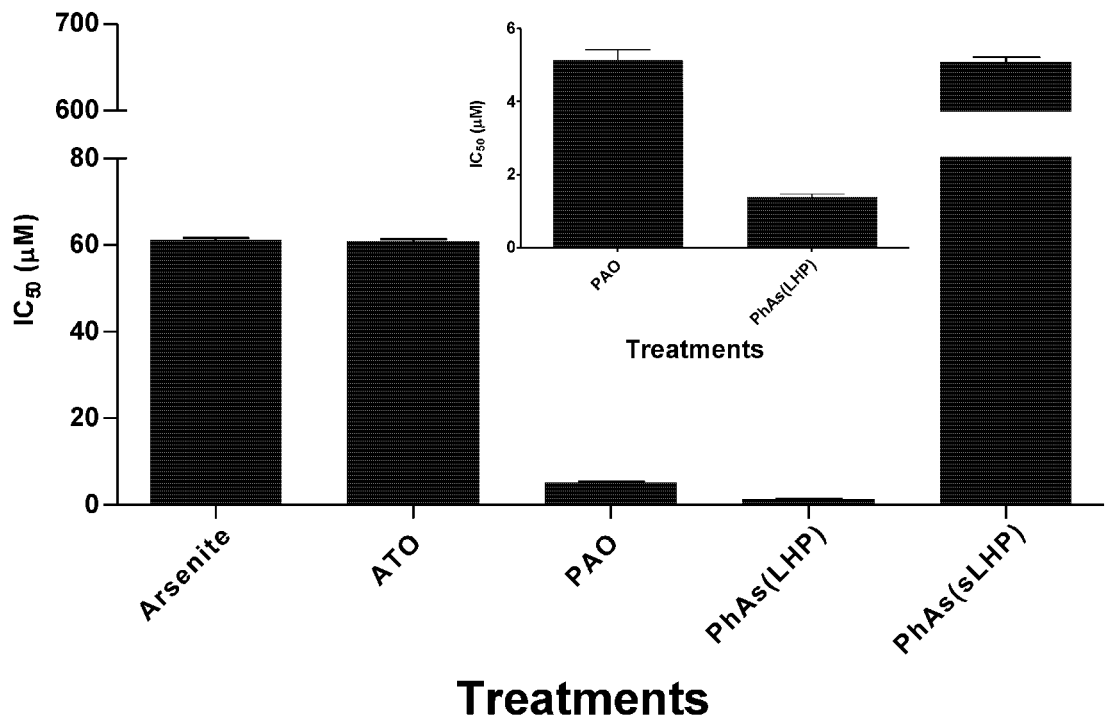
FIG. 18 shows a comparison of $IC_{50}$ values of the specified As compounds obtained from MTT assays on Kasumi-1 cells following 24-h treatment showing substantially improved toxicity of PhAs(LHP) versus its derivative PhAs (sLHP), arsenite, ATO, and PAO.

All arsenic treatments produced typical concentration-response curves. $IC_{50}$ values are summarized in FIG. 18 for arsenite, ATO, PAO, PhAs(LHP) and PhAs(sLHP). The precursor peptides, LHP and sLHP, were non-toxic up to 1000 µM on Kasumi-1 cells. The percentage of MTT conversion remained close to or above 100% in all three MTT assays conducted for each of these peptides.

The least toxic arsenic compound tested was PhAs(sLHP) (1050=650±0.6 µM) and was significantly less toxic than all other arsenic compounds tested (Table 18). This large $IC_{50}$ value indicates that the coordinated non-targeting peptide is not recognised by these cells, and that its bulky presence inhibits uptake into the cells. The large $IC_{50}$ value for PhAs(sLHP) was excluded from the statistical analysis of the $IC_{50}$ values for the other As compounds to prevent this high number from distorting the analysis. The compound of interest, PhAs(LHP) ($IC_{50}$=1.4±0.1 µM), was 3.6 times more toxic than PAO ($IC_{50}$=5.1±0.5 µM, P<0.001) indicating that the peptide is likely aiding the uptake of As into these cells. It was approximately forty times more toxic than ATO (61±1 µM, P<0.001). PhAs(LHP) was about 460 times more toxic than the analogous compound, PhAs(sLHP) (P<0.001), containing the scrambled peptide indicating that the peptide configuration plays an important role in the toxicity of PhAs(LHP) toward these cells.

These results suggest the potential for PhAs(LHP) to be used for the treatment of AML, which currently exhibits a poor cure rate (only 27% survival rate).

TABLE 18

Results of the statistical analysis comparing the $IC_{50}$ values obtained from MTT assays following 24-h treatment of Kasumi-1 cells.

| Tukey's Multiple Comparison Test | Mean difference | q | Significant? | P< |
|---|---|---|---|---|
| Arsenite vs ATO | 0.3738 | 0.1383 | No | ns |
| Arsenite vs PAO | 56.11 | 20.75 | Yes | <0.0001 |
| Arsenite vs PhAs(LHP) | 59.87 | 22.14 | Yes | <0.0001 |
| Arsenite vs PhAs(sLHP) | −594.7 | 219.9 | Yes | <0.0001 |
| ATO vs PAO | 55.74 | 20.62 | Yes | <0.0001 |
| ATO vs PhAs(LHP) | 59.49 | 22.00 | Yes | <0.0001 |
| ATO vs PhAs(sLHP) | −595.0 | 220.1 | Yes | <0.0001 |
| PAO vs PhAs(LHP) | 3.753 | 1.388 | No | ns |
| PAO vs PhAs(sLHP) | −650.8 | 240.7 | Yes | <0.0001 |
| PhAs(LHP) vs PhAs(sLHP) | −654.5 | 242.1 | Yes | <0.0001 |

MTT Results and $IC_{50}$ Values for KARPAS 45 Cells

Figure 19:
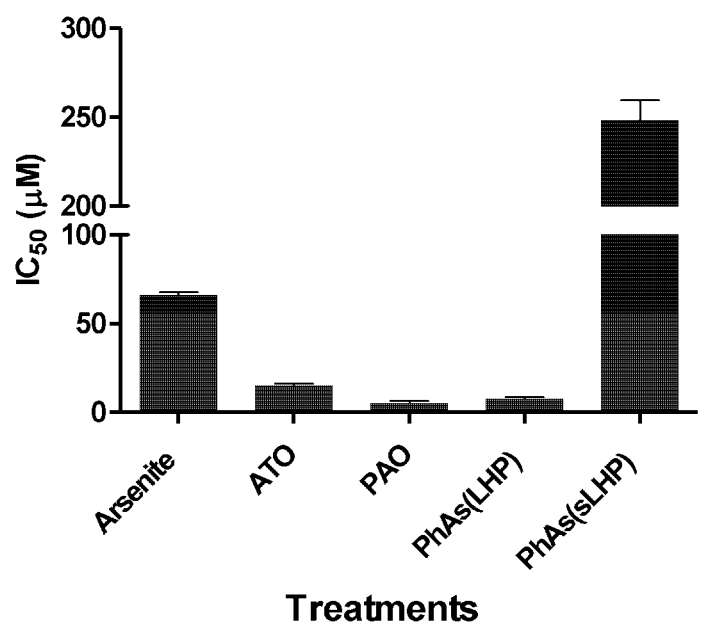
FIG. 19 is a representation of the results of a comparison of $IC_{50}$ values of the specified As compounds obtained from MTT assays on KARPAS 45 cells following 24-h treatment, showing good toxicity of PhAs(LHP) which contains the targeting peptide and the greatly reduced toxicity of PhAs (sLHP) which contains the scrambled peptide (no longer targeting)

The $IC_{50}$ values were obtained for arsenite, ATO, PAO, PhAs(LHP) and PhAs(sLHP) following the 24-h treatment of KARPAS 45 cells, and are shown in FIG. 19. The $IC_{50}$ value for ATO ($IC_{50}$: 15.1±1.8 µM) was surprisingly 23% of the value for arsenite ($IC_{50}$: 66.2±2.6 µM), which infers that the anion acts differently to ATO in this cell line, either by mode of uptake or mode of action. PAO ($IC_{50}$: 5.1±2.3 µM)

was approximately three times more toxic than ATO indicating that the toxicity is influenced by the lipophilicity influencing the uptake of this compound. Alternatively, the PAO is more toxic once it is in the cell. The compound of interest, PhAs(LHP) (IC$_{50}$: 7.8±1.2 µM), was about twice as toxic as ATO but slightly less toxic than PAO. This can be put into context when compared with the result for the arsenic scrambled peptide complex. The arsenic compound with the scrambled peptide, (PhAs(sLHP), IC$_{50}$: 248±19 µM) proved to be 32 times less toxic than PhAs(LHP) in the KARPAS 45 cells indicating that the peptide configuration must play an important role in the toxicity of PhAs(LHP) toward these cells. This also shows that the greater molecular weight (resulting from the peptide) reduces uptake unless the peptide is in the correct configuration to target the macropinocytotic pathway.

Acetarsol, was tested up to 1000 µM and failed to produce an IC$_{50}$ value. Due to the changes in the pH of the cell medium, higher concentrations were not tested. LHP and sLHP were non-toxic up to 1000 µM on KARPAS 45 cells. The cell viability for both of these compounds remained close to or above 100% in all three MTT assays.

The IC$_{50}$ values of the compounds were statistically compared across the group. The value for PhAs(sLHP) was statistically different to all other compounds (P<0.0001). Due to the large IC$_{50}$ value and corresponding standard deviation for PhAs(sLHP), the results of this compound were omitted from the statistical comparisons between the IC$_{50}$ values of the other compounds. Importantly the analysis showed that the differences between most results were statistically significant, as depicted in table 19. It was found that the IC$_{50}$ value for arsenite was significantly different from all the other compounds tested (P<0.0001). The IC$_{50}$ value associated with PAO was significantly lower than that of ATO (P<0.001) but was not found to be significantly lower than that of PhAs(LHP). The IC$_{50}$ value of PhAs(LHP) was significantly lower than that of ATO (P<0.05) and arsenite (P<0.0001).

TABLE 19

Results of the statistical analysis comparing the IC$_{50}$ values obtained from MTT assays following 24-h treatment of KARPAS 45 cells.

| Tukey's Multiple Comparison Test | Mean Difference | q | Significant | P |
| --- | --- | --- | --- | --- |
| Arsenite vs ATO | 51.16 | 42.91 | Yes | <0.0001 |
| Arsenite vs PAO | 61.08 | 51.23 | Yes | <0.0001 |
| Arsenite vs PhAs(LHP) | 58.47 | 49.04 | Yes | <0.0001 |
| ATO vs PAO | 9.917 | 8.318 | Yes | <0.0001 |
| ATO vs PhAs(LHP) | 7.303 | 6.126 | Yes | <0.05 |
| PAO vs PhAs(LHP) | -2.613 | 2.192 | No | ns |

MTT Results and IC$_{50}$ Values for HepG2 Cells

Figure 20:
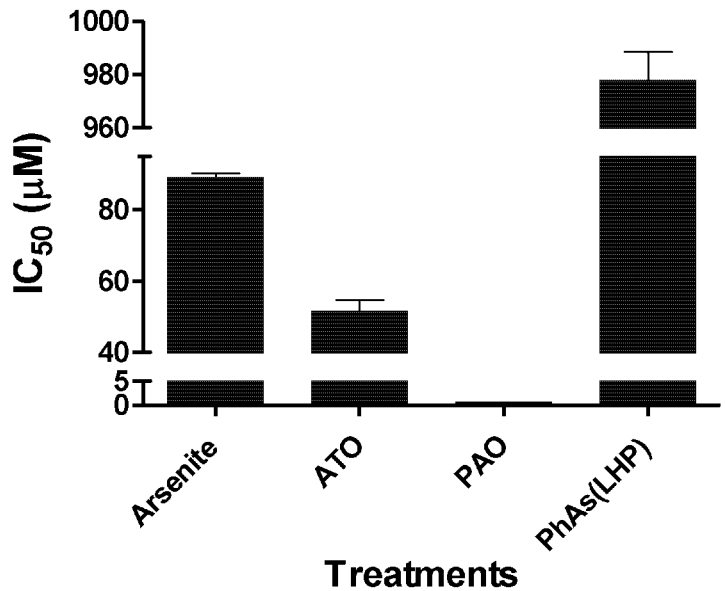
FIG. 20 is a representation of the results of a comparison of $IC_{50}$ values of the specified As compounds obtained from MTT assays on HepG2 cells following 24-h treatment; indicating that PhAs(LHP) is less toxic toward these fast growing cancer cells, that are not targeted by the peptide.

FIG. 20 shows the IC$_{50}$ values that were obtained for arsenite, PAO, ATO, and PhAs(LHP) from MTT assays following the 24-h treatment of HepG2 cells. ATO produced an IC$_{50}$ value of 52±3 µM, which was 1.7 times more toxic than arsenite with an IC$_{50}$ value of 89±1 µM. The compound of interest, PhAs(LHP), produced a very high IC$_{50}$ value of 978±11 µM, and was about nineteen times less toxic than ATO (IC$_{50}$: 52±3 µM) and over one thousand five hundred times less toxic than PAO (IC$_{50}$: 0.63±0.01 µM). As PAO is the starting material for PhAs(LHP) these results, once again, strongly indicate that the conjugation to the leukemia homing peptide plays an important role in the targeting ability and toxicity of PhAs(LHP) toward cells and again implies that the greater molecular weight complex, PhAs(LHP), is not toxic toward the cells that do not recognise the peptide.

Acetarsol and LHP, were both tested up to 1000 µM, but failed to produce IC$_{50}$ values. Instead the viability of HepG2 cells remained close to or above 100% in all three MTT assays for each of these compounds.

The IC$_{50}$ values obtained from MTT assays following 24-h treatment of HepG2 cells were statistically compared across the group and the value for PhAs(LHP) was found to be significantly different in comparison to all other compounds (P<0.0001).

IC$_{50}$ Values for A549 Human Lung Cancer Cells for PhAs(LHP)

The IC$_{50}$ value for PhAs(LHP) in A549 cells is 234±5 µM. Once again this shows comparatively low toxicity of the complex towards human solid tumour cells versus leukemia cells.

MTT Results and IC$_{50}$ Values for CH Solid Tumour Cells

Figure 21:
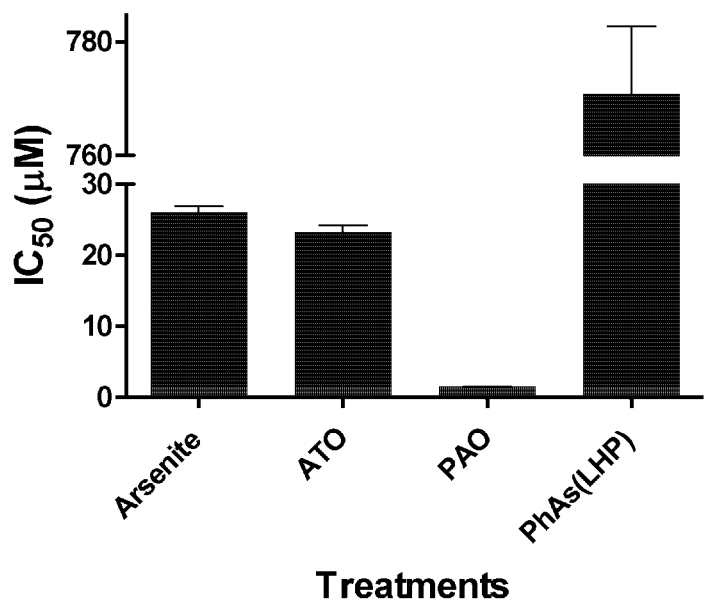
FIG. 21 is a representation of the results of a comparison of $IC_{50}$ values of the specified As compounds obtained from MTT assays on Chinese hamster (CH) solid tumour cells following 24-h treatment, indicating that PhAs(LHP) is less toxic toward these fast growing cancer cells, that are not targeted by the peptide.

IC$_{50}$ values obtained for arsenite, PAO, ATO, and PhAs(LHP) following the 24-h treatment of CH solid tumour cells are shown in FIG. 21. The compound of interest, PhAs(LHP), produced a high IC$_{50}$ of 770±12 µM, and was about thirty four times less toxic than ATO (IC$_{50}$: 23.3±0.9 µM) and over five hundred times less toxic than PAO (IC$_{50}$: 1.49±0.03 µM). This suggests that the greater molecular weight of the PhAs(LHP) complex hinders cell uptake; which is expected, since the peptide should not be recognised by the receptor for uptake by the macropinocytotic pathway of these non-human tumour cells.

Acetarsol, was tested up to 1000 µM and failed to produce an IC$_{50}$ value. LHP was non-toxic up to 1000 µM on CH solid tumour cells. The cell viability for both of these compounds remained close to or above 100% in triplicate MTT assays.

The IC$_{50}$ values for each compound were statistically compared across the group and the value for PhAs(LHP) was significantly higher than all the other arsenic compounds assayed (P<0.0001).

MTT Results and IC$_{50}$ Values for hPBMC

Figure 22:
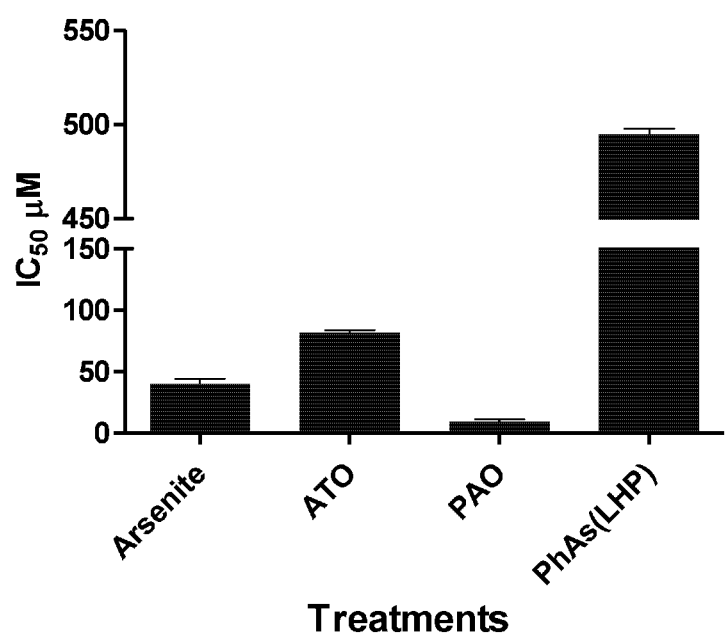
FIG. 22 is a representation of the results of a comparison of $IC_{50}$ values of the specified As compounds obtained from MTT assays on hPBMC following 24-h treatment, indicating that PhAs(LHP) is less toxic toward these normal cells.

The IC$_{50}$ values obtained for arsenite, ATO, PAO, PhAs(LHP) and PhAs(sLHP) on hPBMC following 24-h treatment are shown in FIG. 22. Interestingly, ATO produced an IC$_{50}$ value (81.7±4.0 µM) approximately twice that obtained for arsenite (40.1±7.7 µM) despite containing double the number of arsenic atoms as arsenite. Once again this suggests that the anion acts in a different mode against these two cell lines; either by a different uptake mechanism or mode of action for toxicity. PAO was the most toxic compound with an IC$_{50}$ value of 9.3±3.3 µM which is approximately a quarter of that for arsenite and about a tenth of the value for ATO.

Most importantly, the compound of interest, PhAs(LHP), produced a high IC$_{50}$ value of 495±6 µM. This appears to confirm the targeting ability of the peptide toward leukemia cells over healthy cells.

Once again acetarsol and LHP were both tested up to 1000 µM and failed to produce IC$_{50}$ values.

The results of the statistical analyses undertaken on the IC$_{50}$ values obtained following 24-h treatment of hPBMC are listed in table 20. It was found that the value for every compound was significantly different to each of the other values (P<0.0001).

TABLE 20

Results of the statistical analysis comparing the $IC_{50}$ values obtained from MTT assays following 24-h treatment of hPBMC.

| Tukey's Multiple Comparison Test | Mean Difference | Q | Significant | P |
|---|---|---|---|---|
| Arsenite vs ATO | −41.65 | 13.33 | Yes | <0.0001 |
| Arsenite vs PAO | 30.74 | 9.837 | Yes | <0.0001 |
| Arsenite vs PhAs(LHP) | −454.6 | 145.5 | Yes | <0.0001 |
| ATO vs PAO | 72.39 | 23.17 | Yes | <0.0001 |
| ATO vs PhAs(LHP) | −413.0 | 132.2 | Yes | <0.0001 |
| PAO vs PhAs(LHP) | −485.4 | 155.3 | Yes | <0.0001 |

Comparison of the $IC_{50}$ Values of the Arsenic Compounds Tested Across the Various Cell Lines Table 21 shows a summary of the $IC_{50}$ values obtained from MTT assays following the 24-h treatment with the four specified arsenic compounds in six different cell lines. The $IC_{50}$ values for arsenite across the 7 cell lines ranges between 18.6±0.5 μM for K562 cells and 89±1 μM for HepG2 cells. There appears to be no apparent difference between leukemia and non-leukemia cell types following treatment with arsenite. Surprisingly, arsenite is less toxic toward the fast growing HepG2 cells than it is toward the static hPBMC.

ATO produced $IC_{50}$ values ranging from 7.0±0.1 μM for HL-60 cells to 82±4 for hPBMC. Since the hPBMC are static cells, the differences in these values are not surprising because arsenic is well known for its interaction with a number of cell division molecules, for example, tubulin and these targets would not be available in static cells. ATO displayed slightly greater toxicity toward K562 cells, HL-60 cells and KARPAS 45 cells (9.7±0.2 μM, 7.0±0.1 μM, and 15±2 μM, respectively). The toxicity was significantly lower toward the Kasumi-1 cells (61±1 μM), the HepG2 cells (52±3 μM) and the hPBMC (82±4 μM).

PAO has produced low μM $IC_{50}$ values ranging between 0.63±0.01 μM and 9±3 μM. This high toxicity towards all cell types is most likely related to the increased lipophilicity, previously mentioned, due to the presence of the phenyl group.

All the $IC_{50}$ values obtained for the arsenic scrambled peptide complex, PhAs(sLHP), were very large, ranging from 205±4 μM in HL-60 cells to 960±10 μM in HepG2 cells (table 21)

Figure 23:
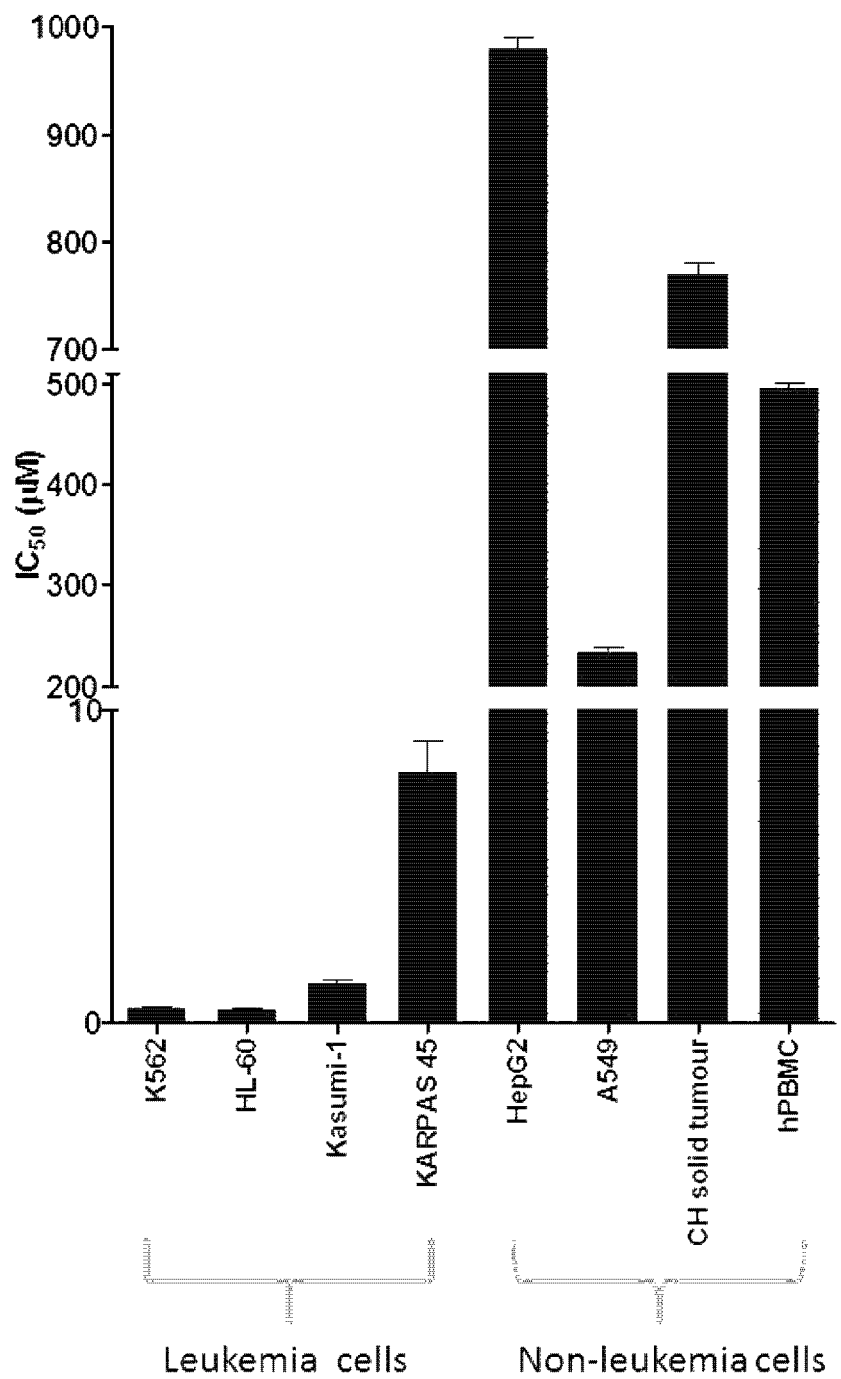
FIG. 23 is a comparison of $IC_{50}$ values for PhAs(LHP) across cell lines following 24-h treatment, showing the good toxicity of PhAs(LHP) against the leukemia cell lines (K562, HL-60, Kasumi-1 and KARPAS 45 which are targeted by the peptide), greatly reduced toxicity in the adherent fast growing cancer cell lines (HepG2, A549 and CH solid tumour cells which are not targeted by the peptide) and also reduced toxicity in the normal blood cells (hPBMC, which are also not targeted by the peptide)

The high selective toxicity (as graphically depicted in FIG. 23) of PhAs(LHP) toward leukemia cells in comparison to non-leukemia cells, is noteworthy. PhAs(LHP) displays an $IC_{50}$ value in the nM range toward both myeloid leukemic K562 cells and HL-60 cells with $IC_{50}$ values approximately 1000 times greater in hPBMC, approximately 1500 times greater in CH solid tumour cells, almost 2000 times greater in HepG2 cells, and 470 times greater in A549 cells, indicating the potential of this compound as a treatment for myeloid leukemias. The result for the Kasumi-1 cells is particularly promising. While PhAs(LHP) does not display an $IC_{50}$ value in the nM range toward the lymphoid leukemic KARPAS 45 cells, the $IC_{50}$ value is approximately 64 times greater in hPBMC indicating a good therapeutic window for this compound such that it may also be a potential treatment for T-cell leukemias.

The large differences between the results for leukemic cancer cells and the fibroblastic cells could be an indication that PhAs(LHP) would be less toxic toward tissue. Surprisingly, the $IC_{50}$ value obtained for the fast growing non-leukemia HepG2 cells, was much greater than the value obtained for the static hPBMC, opening up the possibility that PhAs(LHP) may decrease the side effects commonly associated with the toxicity of arsenic treatments toward fast growing cells. Animal testing and analysis of tissue samples will be necessary to further examine this hypothesis.

Summary of as Uptake Following 24-h as Treatment of Different Cell Types

Figure 24:
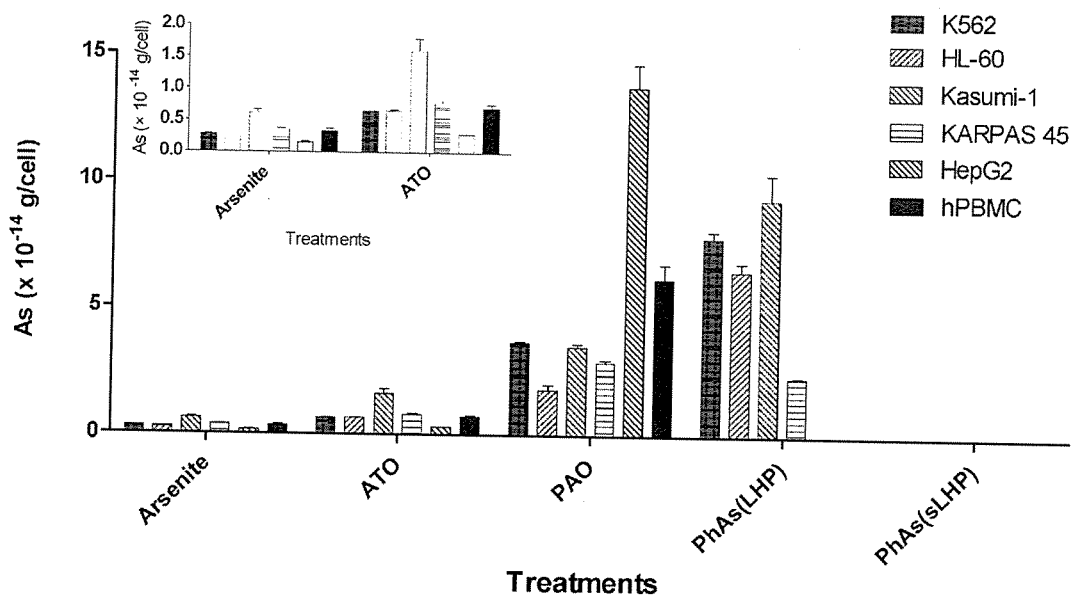
FIG. 24 is a graphical summary of the cellular As concentrations associated with the specified cell lines following 24-h treatment (1.5 µM As). The results are represented as the mean and standard deviation of triplicate samples. The results show selective As uptake in leukemia cell lines following treatment with PhAs(LHP) and no detectable As uptake in the non-leukemia cells.

FIG. 24 summarises the cellular As concentrations associated with the different cell types following 24-h treatment with the various As compounds (1.5 μM As). The leukemia cell lines, K562, HL-60, Kasumi-1 and KARPAS 45, are depicted in red (lighter of the filled in blocks), and the non-leukemia cell types are depicted in black (darkest shading), with the cancerous adherent cells, HepG2, in the diagonal stripes, and the normal cells, hPBMC, in solid black.

Following PhAs(LHP)-treatment, significant (P<0.001) cellular As concentrations were detected in the four leukemia cell lines (K562, HL-60, Kasumi-1 and KARPAS 45) but, most importantly, there were no detectable cellular As concentrations associated with either non-targeted, malignant cells, HepG2, or in the non-targeted, normal, non-cancerous hPBMC. The cellular As concentration resulting from PhAs(LHP) treatment was highest in the Kasumi-1 cells. This concentration was 1.2 times higher than the cellular As concentration associated with the K562 cells (P<0.05), 1.4 times greater than the HL-60 cells (P<0.001) and 4.0 times higher than the cellular As concentration associated with the KARPAS 45 cells (P<0.001).

TABLE 21

Comparison of the $IC_{50}$ values (μM) obtained from MTT assays of the specified arsenic compounds following 24-h treatment of the cell lines.

| | | LHP[†] target | Arsenite | ATO | PAO | PhAs(LHP) | PhAs(sLHP) |
|---|---|---|---|---|---|---|---|
| Leukemia cells | K562 | *** | 18.6 ± 0.5 | 9.7 ± 0.2 | 3.4 ± 0.4 | 0.49 ± 0.02 | 790 ± 30 |
| | HL-60 | ** | 20 ± 1 | 7.0 ± 0.1 | 1.5 ± 0.3 | 0.5 ± 0.1 | 205 ± 4 |
| | Kasumi-1 | ? | 61.2 ± 0.6 | 61 ± 1 | 5.1 ± 0.5 | 1.4 ± 0.1 | 660 ± 10 |
| | KARPAS 45 | ? | 66 ± 3 | 15 ± 2 | 5 ± 2 | 8 ± 1 | 250 ± 20 |
| Non-leukemia cells | HepG2 | No | 89 ± 1 | 52 ± 3 | 0.63 ± 0.01 | 978 ± 11 | 960 ± 10 |
| | A549 | No | | | | 234 ± 5 | |
| | CH solid tumour | No | 26.1 ± 0.8 | 23.3 ± 0.9 | 1.49 ± 0.03 | 770 ± 12 | |
| | hPBMC | No | 40 ± 8 | 82 ± 4 | 9 ± 3 | 495 ± 6 | 665 ± 8 |

[†]LHP target: * highly recognised target,  recognised target, ? not known.

Treatment with PhAs(sLHP) resulted in no detectable As uptake in any of the cell types tested, indicating that the uptake of the As-peptide was highly dependent on the amino acid sequence of the peptide.

The cellular As concentrations following arsenite-treatment were all very small ($<4\times10^{-14}$ g/cell). The greatest cellular As concentration, associated with the KARPAS 45 cells, was 2.2 times more than the least amount, associated with the HepG2 cells. The concentration in the HepG2 cells was significantly lower than that observed for all other cell types ($P<0.01$). There was also no identifiable trend for the hPBMC.

Interestingly, ATO treatment resulted in greater uptake in the leukemia cells and in the normal hPBMC than the adherent cancer cell line, HepG2. The cellular As concentrations associated with the K562, HL-60 cells, and hPBMC were similar ($P>0.05$). The highest cellular As concentration was found in the Kasumi-1 cells, significantly higher than the cellular As concentrations associated with each of the other cell types ($P<0.001$). It was 5.5 times greater than the cellular As concentration associated with the HepG2 cells.

Large variations were evident in the cellular As concentrations following PAO treatment, with the HepG2 cells now exhibiting a significantly greater As concentration than all the other cell types, ($P<0.001$). This concentration was 2.2 times higher than the cellular As concentration associated with the PAO-treated hPBMC, 3.8 times higher than the K562 cells, 3.9 times greater than the Kasumi-1 cells, 4.8 times higher than the KARPAS 45 cells, and 7.6 times greater than the HL-60 cells. It was interesting that the second greatest cellular As concentration was exhibited by hPBMC and that this was significantly higher than the cellular As concentrations associated with the leukemia cell lines ($P<0.001$).

Investigations into the Fate of PhAs(LHP) in Leukemia Cells

Method

The cell lines, K562 and HL-60, were obtained and maintained as previously described. Glutaraldehyde (25% solution), Spurr's low viscosity embedding resin, 3-mm gold Finder grids, and toluidine blue were sourced from Proscitech (Kirwan, Australia). Thin-sectioned cells were prepared for microprobe SRXRF analysis using procedures documented previously. Briefly the cells were treated in cell culture flasks (75 cm$^2$) with either IMDM (for the control cells, 4 h or 24 h) or PhAs(LHP) (10 μM in IMDM, 4 h or 24 h). The cells were washed with PBS (2 times) using centriguation and the final cell pellet was fixed in gluteraldehyde (1 mL, 2% v/v in PBS) for 2 h at room temperature; and dehydrated in ethanol (30%×2, 50%×2, 70%×2, 80%×2, 90%×2, 95%×2, 100%×4). Infiltration was achieved by rocking the cells in 50% ethanol/50% Spurr's resin overnight and then replacing with 100% Spurr's resin (×2 over 2 days) to ensure the removal of all traces of water. On the final day, the cells were embedded in 100% Spurr's resin, centrifuged (8000 g, 1 h) and cured at 60° C. overnight in a Beem capsule. Thin sections (1 μm) of the cell pellet were cut using an ultramicrotome (Leica EM UC7). The thin-sections were stained with toluidine blue before mounting on silicon nitride membranes.

The gold Finder grids were attached to kinematic mounts designed to fit both the light microscope (Leica DMXRE Epi-fluorescence/visual microscope) and the X-ray microprobe (2-ID-D). Optical micrographs and XY coordinates were obtained in order to locate suitable cells for analysis. Those cells that exhibited an intact appearance, a clearly defined nucleus and were located away from other cells and cellular debris were chosen for analysis.

Microprobe SR-XRF was performed at beamline 2-ID-D at the Advanced Photon Source, Argonne National Laboratory (Lemont, Ill., USA). The 11.9-keV X-ray beam was focused to a spot size of 0.3×0.3 μm$^2$ using two zone plates. The samples were housed in a helium atmosphere and the distributions of the elements from P (2.1 keV) to As (11.9 keV) were mapped by raster scanning the sample in 0.3 μm steps, with the aid of a XYZ motorised stage. Fluorescent X-rays were detected using a dwell time of 2.5 s/pt and an energy dispersive Vortex EM (Hitachi High-Technologies Science America, Northridge, Calif.) silicon drift detector. Elemental distribution maps were processed using MAPS Version 1.7.3.02 software package (S. Vogt, Advanced Photon Source). Conversion of elemental fluorescence intensities to absolute densities in microgram per square centimetre (μg/cm$^2$) was performed by comparing X-ray fluorescence intensities with those from thin film standards, NBS-1832 and NBS-1833 (NIST, Gaithersburg, Md., USA).

Results

Figure 25:
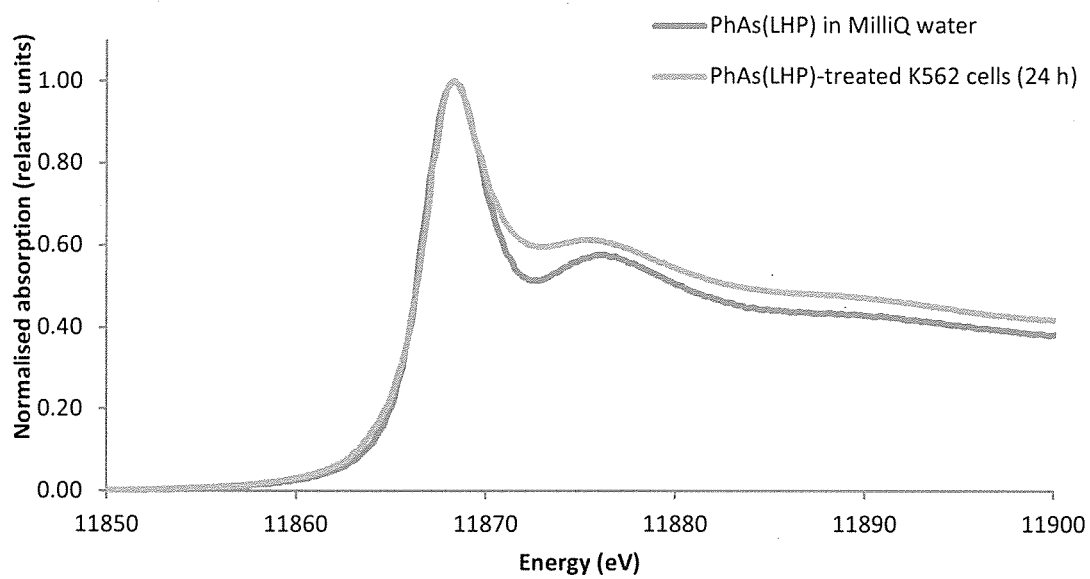
FIG. 25 is the As K-edge XANES spectra of PhAs(LHP) (1 mM) in MilliQ water and PhAs(LHP)-treated K562 cells (4 h and 24 h, lower line of overlapping traces), showing that As remains as As(III) but that there are intracellular modifications of the As—S binding.

FIG. 25 depicts the As K-edge spectra obtained for the PhAs(LHP) standard and the PhAs(LHP)-treated K562 cells (24 h). The constant edge energy indicates that the intracellular As remains as As(III) over the 24 h. The change in the post edge region suggests some modification to the As—S binding. For instance, this could reflect the dissociation of the leukemia homing peptide from the PhAs and its subsequent binding to other biomolecules within the cells.

Figure 26:
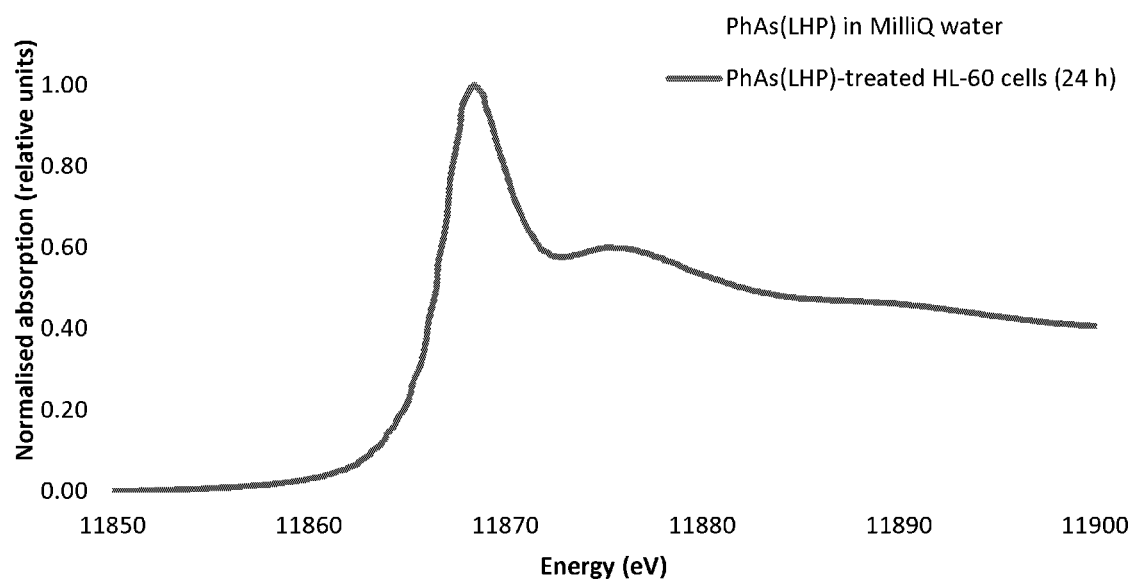
FIG. 26 is the As K-edge XANES spectra of PhAs(LHP) (1 mM) in MilliQ water and PhAs(LHP)-treated HL-60 cells (4 h and 24 h, lower line of overlapping traces), showing that As remains as As(III) but that there are intracellular modifications of the As—S binding.

FIG. 26 depicts the As K— edge spectra obtained for the PhAs(LHP) standard and the PhAs(LHP)-treated HL-60 cells (24 h). The spectral changes observed for the PhAs (LHP)-treated K562 cell sample are also evident in the HL-60 cells, whereby the edge energy remains constant. This shows that the PhAs(LHP) remains as As(III) over the 24-h period. The edge energy is also consistent with the As atom bound to sulfur moieties but the post-edge dip is not as pronounced as that observed in the PhAs(LHP) standard, once again suggesting potential ligand exchange reactions with other (sulfur-containing) biomolecules in the cell.

Figure 27:
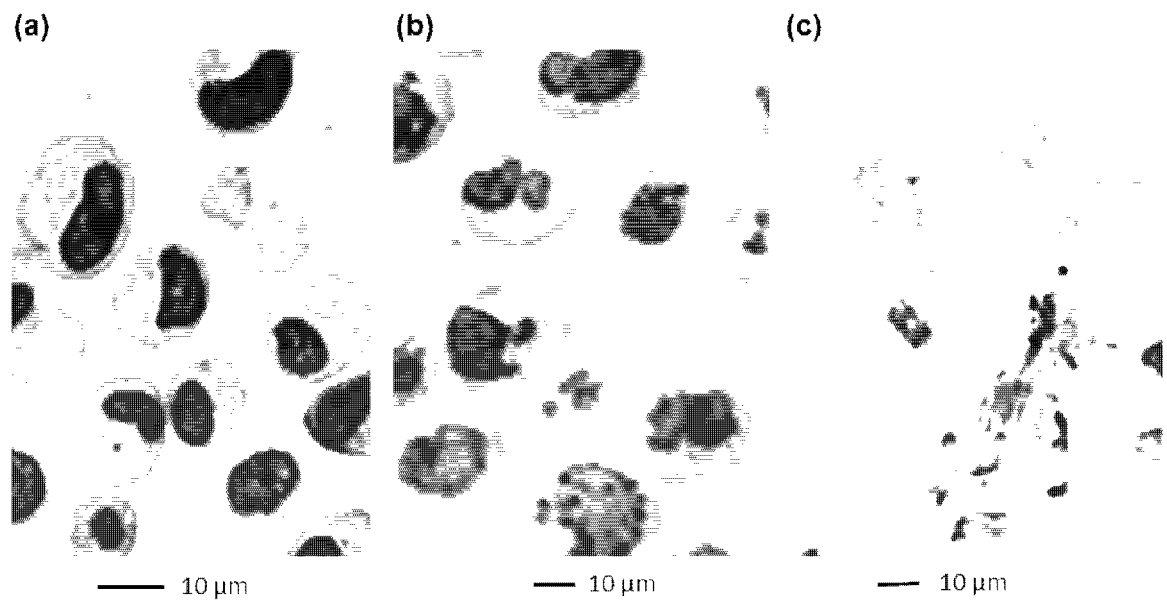
FIG. 27 is a series of micrograph images of toluidine-blue-stained, thin-sectioned control and PhAs(LHP)-treated K562 cells. (a) K562 control cells (b) PhAs(LHP)-treated K562 cells (10 µM, 4 h) (c) PhAs(LHP)-treated K562 cells (10 µM, 24 h), showing the stress and cell demise following PhAs(LHP) treatment.

FIG. 27 depicts the micrograph images of the toluidine-blue-stained thin-sectioned K562 cell samples prior to XRF analysis. The cells in the K562 control cell sample (FIG. 27a) are generally spherical with a clearly defined and intact nucleus. Each treatment time-point shows the stress and demise of the cells in response to treatment with PhAs(LHP) (10 μM). Following 4 h treatment ((FIG. 27b), the majority of cell membranes appear intact, although there is clear evidence of cell stress with fragmentation of the nucleus. FIG. 27c, depicting the 24-h treatment (10 μM), clearly shows breakdown of the cell membrane and fragmented/dispersed nuclear material.

Three to four cells were imaged for each of the treatment conditions (K562 and HL-60 cells) and a representative image for each is provided in the following data.

Figure 28:
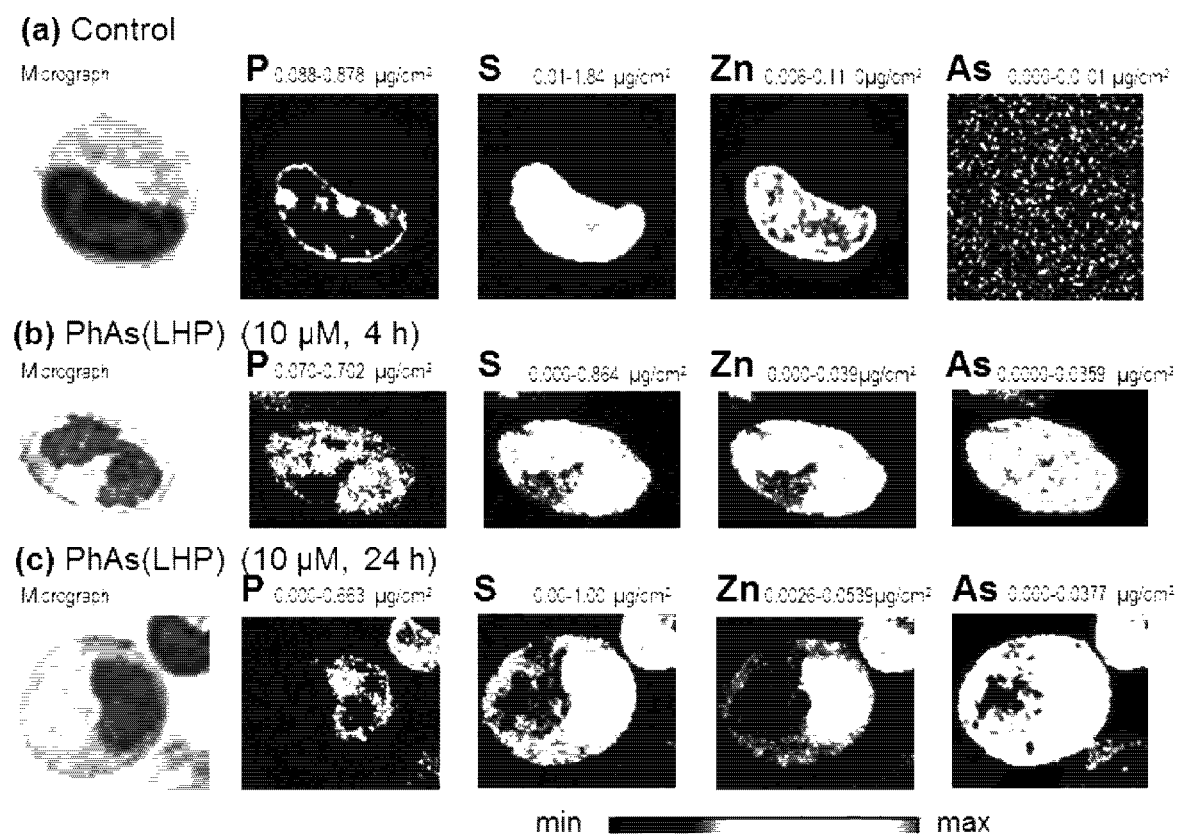
FIG. 28 is a series of micrograph images and correlating microprobe SR-XRF elemental maps for thin-sectioned, toluidine blue stained control and PhAs(LHP)-treated K562 cells. (a) K562 control cells (b) PhAs(LHP)-treated K562 cells (10 µM, 4 h) (c) PhAs(LHP)-treated K562 cells (10 µM, 24 h). Operating conditions include: beam energy=11.9 key; beam size=0.3×0.3 µm$^2$; step size=0.3 µm; dwell time=2.5 s/pt; and scan dimensions (H×V)=(a) 20×21 µm$^2$; (b) 26×18 µm$^2$; (c) 23×21 µm$^2$. This shows localisation of As in the cell nucleus following PhAs(LHP) treatment.

Microprobe SR-XRF elemental distribution maps obtained from thin-sections of the control and PhAs(LHP)-treated (10 μM, 4 h and 24 h) K-562 cells are shown in FIG. 28. Concentrations of P, S, and Zn, which are significantly more abundant than As, are used to define the cell region. P and Zn are markers of the nucleus due to their presence in the DNA phosphate backbone and in DNA transcription proteins (zinc finger proteins), respectively. The control K-562 cells (FIG. 28a) did not contain any significant levels of As, whereas the 4 and 24 h PhAs(LHP)-treated cells (28b and 28c, respectively) each contained significant As throughout the cell with evidence of accumulation in the cell nucleus.

FIG. 29a shows the correlative light micrograph of the toluidine-blue-stained thin section of K-562 cells that were exposed to PhAs(LHP) (10 µM, 4 h) while FIG. 29b shows the corresponding SR-XRF maps for P, Zn and As and the colocalisation map for the three elements. The colocalisation map of As with S is not shown due to the use of the toluidine blue stain, which contains S and subsequently affects the intracellular S concentration.

FIGS. 28 and 29 indicated that As has entered the nucleus where it potentially interacts with DNA or the proteins associated with DNA replication as noted by the predominance of blue in the colocalisation map (FIG. 29b). Phosphorus dominated areas are consistent with heterochromatin regions, as reported in the literature. Arsenic, as evident by the distinct blue region in the colocalisation map, is present throughout the nucleus. Close inspection reveals that As is present in the nucleolus, and both the heterochromatin and euchromatin regions (FIG. 29b). The latter area coincides with less densely packed DNA where transcription occurs, allowing As to interact with the sulfur-rich areas common within the transcription proteins. Statistical analysis comparing the concentrations of the endogenous elements in the cytoplasm and the nucleus resulted in no specific trends or changes as a result of PhAs(LHP) treatment for the K562 cells.

FIG. 30 displays the micrograph images of the control and PhAs(LHP)-treated (10 µM, 4 h and 24 h) HL-60 cells. The control cells (FIG. 30a) were typically rounded with large, well-defined nuclei and cell membranes. Following 4-h PhAs(LHP) treatment (FIG. 30b), cell distress is evident in the HL-60 cells, whereby the majority of the cells are no longer rounded but are irregularly shaped with the nuclei of many of the cells also becoming irregularly shaped. The 24-h PhAs(LHP) treatment of HL-60 cells (FIG. 30c) resulted in a high degree of cell degredation with evidence of cell demise.

FIG. 31 depicts the available micrograph images and the corresponding SR-XRF elemental maps for the toluidine-blue-stained, thin sections for the control and PhAs(LHP)-treated (10 µM, 4 h and 24 h) HL-60 cells. As with the K562 cells there was no significant As in the control cells (FIG. 31a). In contrast to the K562 cells, however, there are only small localisations of As evident in the HL-60 cells following 4-h PhAs(LHP) treatment (FIG. 31b) which appears to be associated with the high DNA dense region, most likely the nucleolus. Significant As was evident in the 24-h PhAs (LHP)-treated HL-60 cells (FIG. 31c, FIG. 32b), whereby the nucleus clearly contains a greater accumulation of As than the rest of the cell. The intense As region located in the left lower portion of the cell correlated with an intense region of Zn and less intense region of P, which might be indicative of transcription proteins.

As with the K562 cells, statistical analysis comparing the concentrations of the elements in the cytoplasm and the nucleus of the HL-60 cells resulted in no specific trends or changes that could be attributed to PhAs(LHP) treatment.

Synthesis of Analogues of Phenylarsine Oxide (Para-Substituted) as Precursors for the Preparation of New Phenylarsenic Leukemia Homing Peptide Compounds (XPhAs (LHP))

Methods

Chemicals

All of the commercially available reagents used in this project were of analytical grade or higher. Milli-Q water (18.2Ω, Millipore) was used as a solvent, for dilutions and to prepare buffer solutions. p-Arsanilic acid (≥99%) and activated charcoal (untreated, granular, 8-20 mesh) were purchased from Sigma Aldrich (Australia). Hydrochloric acid (HCl, 32%), methanol (MeOH, >99.7%), diethyl ether ($Et_2O$, >99%), chloroform ($CHCl_3$, >99.5%), ethanol (EtOH, >99.5%), formic acid (99%), iodine (12, >99.5%) and sodium hydroxide (NaOH, >97.5%) were all obtained from Ajax Finechem (Australia). Triphenylphosphine ($PPh_3$, 99%) was purchased from Acros Organics (Australia), while sodium nitrite ($NaNO_2$, >99.8%) was purchased from Thermo Fisher (Australia). Potassium iodide (KI, >99%) was purchased from Chem Supply (Australia). Sodium phosphate dibasic ($Na_2HPO_4$, >99%) and sodium dihydrogen phosphate dihydrate ($NaH_2PO_4.2H_2O$, ≥99%) were purchased from Sigma Aldrich (USA).

Buffer Preparation

The phosphate buffer (pH 8, 0.1 M, 100 mL) was prepared using the appropriate volumes of stock solution A ($NaH_2PO_4.2H_2O$, 0.2 M) and stock solution B ($Na_2HPO_4$, 0.2 M) listed in table 22. The pH was measured and/or confirmed with Mettler Toledo Sever Compact S220-Micro Kit following calibration with Mettler Toledo technical buffers (pH 4.0, 7.0, and 9.2) and adjusted by the dropwise addition of either Solution A or Solution B as required, pending pH measurement, prior to dilution to 100 mL with Milli-Q water (final concentration 0.1 M).

TABLE 22

Stock solution combinations for phosphate buffers at specific pH*

| pH | Solution A (mL) | Solution B (mL) |
|---|---|---|
| 8.0 | 2.65 | 47.35 |

*pH determined at 25° C.

ESI-MS Analysis of Formation of XPhAs(LHP) Complexes

The coordination of the aforementioned precursors ($NH_2PhAs(III)$, ClPhAs(V) or IPhAs(V), Section 1.3.3) with LHP (described in Section 1.3.5) were monitored using ESI-MS to optimise the reaction conditions and, subsequently, product formation. The reactions were performed under a $N_2$ atmosphere using the conditions described in Section 1.3.5. At the specified times, an aliquot was removed and the solution was diluted (50×) in 0.1% formic acid for analysis by electrospray ionisation-mass spectrometry (ESI-MS).

Operating Conditions for ESI-MS

All mass spectra were collected with a Micromass Quattro Micro triple-quadrupole mass spectrometer (Micromass, UK) employing electrospray ionisation in the positive ion mode. Heated dry nitrogen was used as the nebulising and drying gas for all experiments. A capillary voltage of 3.00 kV, cone voltage of 35 V, source temperature of 80° C., desolvation temperature of 120° C. and desolvation gas flow of 400 L/h were employed to collect the spectra.

The source was rinsed thoroughly with Milli-Q water prior to sample injection until the spectrum resembled the baseline spectrum. Each sample was then injected at a flow rate of 20 µL/min using a 1-mL syringe (SGE Analytical Science, Australia). Data acquisition was conducted in continuum mode and typically 50 scans were summed to obtain representative spectra. The spectra were processed with MassLynx software (Waters, 2003). Background subtraction was carried out with a polynomial order of 1 with 40% below the curve, and smoothed with the Savitsky-Golay algorithm. Centroid spectra were then generated with the centre function (Top, area), and each peak was annotated with its respective m/z ratio and intensity.

Purification of XPhAs(LHP) complexes

Analytical HPLC

A Shimadzu analytical HPLC system with Prominence-i LC2030C system controller, auto injector and liquid chromatograph unit was used for the purification of the XPhAs (LHP) complexes. A Waters Sunfire C18 column, 5 µm, 4.6×250 mm (No. 186002560) was used following equilibration with $H_2O$ (0.1% TFA) for 20 mins. A linear gradient elution with $H_2O$/ACN (0.1% TFA), was applied from 100% $H_2O$ to 100% ACN, using a flow rate of 1 mL/min. All solvents were degassed by filtration and sonication prior to use. The samples were filtered through a 0.20-µm filter (Sartorius) prior to analysis. The solution (1 mL) of XPhAs (LHP), prepared according to the optimum reaction conditions (as determined from the results of the method development), was injected onto the column and analysed in order to determine elution times of each species in solution. Each of the relevant As precursors ($NH_2$PhAs(III), ClPhAs(V) or IPhAs(V)) were also analysed to establish their elution times.

Preparatory HPLC

Based on the elution profile obtained from the analytical HPLC, purification of the X-PhAs(LHP) reaction products was performed using preparative HPLC employing a Shimadzu SIL-10AP auto sampler, Shimadzu LC-20AP preparative liquid chromatograph, Shimadzu FCV-200AL quaternary valve, Shimadzu SPD-M20A diode array detector, Shimadzu DGU-20A5R degassing unit, Shimadzu CDM-20A communications bus module, LabSolutions Software and a Luna 5u C18(2) column (250×21.20 mm, 5 micron, Phenomenex). The column was equilibrated with $H_2O$ (0.1% TFA, 20 min). A solution (6 mL) of the XPhAs(LHP), prepared according to the optimum reaction conditions (as determined from the results of the method development), was injected onto the column and separated using the eluent gradients detailed in Table 23 and Table 24. The flow rate was maintained at 15 mL/min and the fractions were detected at A 254 nm. The major fractions were collected and characterised by ESI-MS (operating conditions as previously listed).

TABLE 23

Reverse-phase preparative HPLC eluent gradient used to purify $NH_2$PhAs(LHP).

| Time (min) | Solvent A (%) | Solvent B (%) |
|---|---|---|
| 0.01 | 100 | 0 |
| 26.00 | 50 | 50 |

TABLE 24

Reverse-phase preparative HPLC eluent gradient used to purify ClPhAs(LHP) and PhAs(LHP).

| Time (min) | Solvent A (%) | Solvent B (%) |
|---|---|---|
| 0.01 | 100 | 0 |
| 30.00 | 57 | 43 |

Drying the as Complexes

To obtain purified compounds, the identified HPLC fractions were dried using an Alpha 1-2 LDplus Freeze Dryer (Christ).

X-Ray Absorption Spectroscopic Characterisation of the Precursors ($NH_2$PhAs(III), ClPhAs(V) and IPhAs(V)) and the Peptide Complexes (XPhAs(LHP))

X-ray absorption spectroscopy (XAS) was employed to determine the arsenic oxidation state and the atoms directly coordinated to As in the precursor and peptide complexes.

Preparation of Samples for XAS Analysis

XAS analyses were performed on the synthesised phenylarsenic compounds, XPhAs(LHP) complexes, and As standards. The solid samples were prepared by thoroughly mixing the sample with solid cellulose (Sigma Aldrich). The dilution ratio was initially determined using the XAFSmass program, although it was found that an additional 10× dilution was optimal for analysis in fluorescence mode. The resultant mixtures were mounted in 1-mm thick aluminium sample holders and sealed with Kapton tape. Each sample was then rapidly submerged in liquid nitrogen and transferred to the liquid helium cryostat where it was analysed at 10° K. X-ray absorption spectra were collected for the following As standards: PAO, phenylarsenic bisglutathione (PhAs$(GS)_2$), p-arsanilic acid and arsenite.

For the preparation of PhAs$(GS)_2$, PAO (0.048 g) was initially dissolved in Milli-Q water (2 mL) by heating overnight (80° C.). The resultant solution was then cooled to room temperature prior to its addition to glutathione (GSH) (0.26 g). The reaction tube was flushed with nitrogen and left to react overnight, typically 16 h. Methanol (10 mL) was added to precipitate the product, which was separated by centrifugation (1700 rpm, 10 mins, Heraeus Labofuge 300). The resultant solid was dried at room temperature.

XAS Experimental Instrument Conditions and Data Analysis

XAS sample analysis was undertaken at The Australian Synchrotron (AS, XAS beamline, Clayton, VIC). The beam energy was ~3.0 GeV, and the beam current was 200 mA. A Si(311) channel cut monochromator controlled the beam energy. All spectra were recorded in fluorescence mode at ~10° K (maintained with a closed-cycle He cryostat, OPTIPTTL4K Optistat™ PTR, Oxford Instruments). Spectra were collected with a 100-element GE fluorescence detector (Eurysis) and a vertical slit width of 0.5 mm.

Arsenic K-edge XAS spectra were collected with the following energy ranges: pre-edge region 11667-11847 eV (10 eV steps); XANES region 11847-11930 eV (0.25 eV steps); and EXAFS region 11930-12468 eV (0.025 $Å^1$ steps in k-space to 13.0 $Å^{-1}$).

A solid gold foil standard was simultaneously analysed in transmission mode downstream of the sample for calibration whereby the energy of the first peak of the first derivative spectrum (corresponding to the edge energy) was defined as 11920.0 eV. Typically, 3-5 scans were collected for all sample analyses. Data processing was performed with EXAFSPAK. The DATFIT module of EXAFSPAK calculated the multiple linear regression analysis. Background subtraction and normalization were achieved with BACK-SUB, while FEFF 8.2 was employed to calculate the theoretical phase and amplitude functions for fitting the EXAFS data.

Synthesis of p-Aminophenyldichloroarsine (NH$_2$PhAs(III))

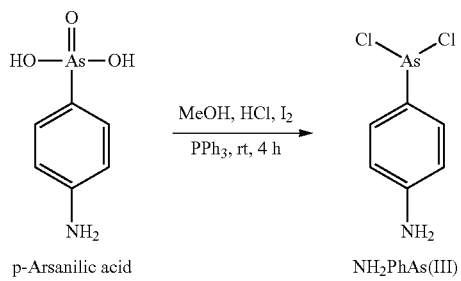

p-Arsanilic acid → NH$_2$PhAs(III)

The reduction of the As(V) compound, p-arsanilic acid, to As(III) was performed in order to facilitate peptide binding via exchange with Cl. The method was adapted from procedures reported by Heredia-Moya and Kirk ((2008) *Bioorg. Med. Chem.* 16, 5743-5746), and Ioannou and Tsivgoulis ((2015) *Main Group Chem.* 14, 237-253). Briefly, p-arsanilic acid (0.2535 g, 1.00 mmol) was dissolved in de-aerated methanol (1 mL) and concentrated HCl (0.68 mL). Triphenylphosphine (0.4170 g, 1.50 mmol) and iodine (0.0123 g, 0.05 mmol) were added, resulting in a red suspension upon stirring. The resultant mixture was stirred for 4 h at room temperature to produce a light yellow solution. The yellow product, p-aminophenyldichloroarsine (NH$_2$PhAs(III)), was precipitated by the addition of ether (1 mL), and the solid was collected. Extraction with a mixture of chloroform (2 mL) and ether (2 mL) was used to separate NH$_2$PhAs(III) from the oxidised side product, triphenylphosphine oxide.

Synthesis of p-Chlorophenylarsonic Acid (ClPhAs(V))

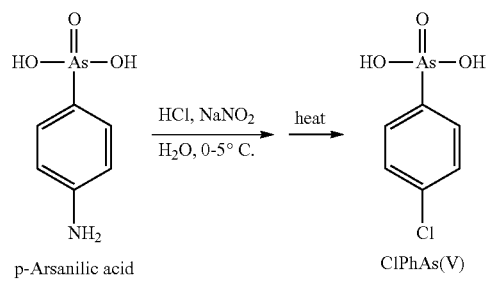

p-Arsanilic acid → ClPhAs(V)

p-Chlorophenylarsonic acid (ClPhAs(V)) was prepared by the diazotisation of p-arsanilic acid and subsequent exchange with Cl. p-Arsanilic acid (0.217 g, 1.00 mmol) was dissolved in MilliQ water (0.2 mL) and concentrated HCl (0.12 mL). Upon complete dissolution, more concentrated HCl (0.13 mL) was added. The solution was cooled to 0-5° C. to create a suspension, and ice (0.1 g) was added to the vessel. A solution of NaNO$_2$ (0.074 g, 1.07 mmol) in MilliQ water (0.2 mL) was added to the acidified solution dropwise with vigorous stirring, resulting in an orange solution. Upon complete addition of NaNO$_2$ the reaction solution had turned light yellow. The reaction vessel was warmed to 50° C. and maintained at that temperature for approximately 2 h, resulting in the evolution of N$_2$ gas. The solution became a dark orange and a precipitate was evident. The suspension was then refrigerated overnight. The resultant solid was isolated and dissolved in warm NaOH (10%, 0.6 mL). This solution was filtered and acidified with HCl to obtain ClPhAs(V).

Synthesis of p-Iodophenylarsonic Acid (IPhAs(V))

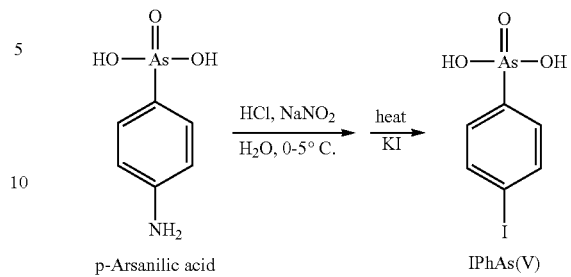

p-Arsanilic acid → IPhAs(V)

p-Iodophenylarsonic acid (IPhAs(V)) was prepared by the diazotisation of p-arsanilic acid and subsequent exchange with I. p-Arsanilic acid (0.217 g, 1.00 mmol) was dissolved in a mixture of MilliQ water (0.2 mL) and concentrated HCl (0.12 mL). Upon complete dissolution, more concentrated HCl (0.13 mL) was added. The solution was cooled to 0-5° C., and ice (0.1 g) was added to the vessel. A solution of NaNO$_2$ (0.074 g, 1.07 mmol) in MilliQ water (0.2 mL) was added to the acidified solution, dropwise, with vigorous stirring. The solution was left in ice for 3 minutes, then a cooled solution of potassium iodide (1.076 g, 0.00648 mol) in MilliQ water (1.5 mL) was slowly added. The reaction vessel was allowed to stand for 3 minutes at room temperature and then warmed to 45° C. until gas evolution ceased (approximately 3-4 h). The suspension was refrigerated overnight and a brown solid was collected and washed with cold MilliQ water. The solid was dissolved in ethanol (1.4 mL) and activated carbon was added. The mixture was diluted with hot water (0.6 mL), brought to the boil and filtered while hot. Cold water (0.8 mL) was added and orange/brown crystals were collected.

Formation of NH$_2$PhAs(LHP)

Triplicate reactions were performed, under the conditions indicated in table 25 using the reactants, NH$_2$PhAs(III) and LHP, to prepare NH$_2$PhAs(LHP). All reaction vials were flushed with N$_2$ prior to incubation. A representative aliquot was analysed by ESI-MS at the specified time points (1 hr, 2 h, 16 h and 24 h) in order to monitor the reaction progress.

TABLE 25

Trial reactions for formation of NH2PhAs(LHP).

| Trial | Concentrations | Ratio NH$_2$PhAs(III):LHP | Solvent | Temp (° C.) | pH |
|---|---|---|---|---|---|
| 1 | 3 mM NH$_2$PhAs(V), 1 mM LHP | 3:1 | MilliQ water | 37 | 7 |
| 2 | 3 mM NH$_2$PhAs(V), 1 mM LHP | 3:1 | Phosphate buffer (H$_2$PO$_4^-$/HPO$_4^{2-}$, 0.1M) | 37 | 8 |

Formation of ClPhAs(LHP)

Triplicate reactions were performed, under the conditions indicated in table 26, using the reactants, ClPhAs(V) and LHP, to prepare ClPhAs(LHP). All reaction vials were flushed with N$_2$ prior to incubation. A representative aliquot was analysed by ESI-MS at the specified time points (30 min, 1 h, 2 h, 24 h, 72 and 96 h) in order to monitor the reaction progress.

TABLE 26

Trial reactions for the formation of ClPhAs(LHP).

| Trial | Concentrations | Ratio ClPhAs(V):LHP | Solvent | Temp (° C.) | pH |
|---|---|---|---|---|---|
| 1 | 1 mM ClPhAs(V), 3 mM LHP | 1:3 | MilliQ water | 37 | 7 |
| 2 | 1 mM ClPhAs(V), 5 mM LHP | 1:5 | MilliQ water | 37 | 7 |
| 3 | 1 mM ClPhAs(V), 8 mM LHP | 1:8 | MilliQ water | 37 | 7 |

Formation of IPhAs(LHP)

Triplicate reactions were performed, under the conditions indicated below, using the reactants, IPhAs(V) and LHP, to prepare IPhAs(LHP). All reaction vials were flushed with $N_2$ prior to incubation. A representative aliquot was analysed by ESI-MS at the specified time points (1 h, 72 h) in order to monitor the reaction progress.

TABLE 27

Trial reactions for the formation of IPhAs(LHP).

| Trial | Concentrations | Ratio IPhAs(V):LHP | Solvent | Temp (° C.) | pH |
|---|---|---|---|---|---|
| 1 | 1 mM IPhAs(V), 3 mM LHP | 1:3 | MilliQ water | 37 | 7 |
| 2 | 1 mM IPhAs(V), 4 mM LHP | 1:4 | MilliQ water | 37 | 7 |
| 3 | 1 mM IPhAs(V), 5 mM LHP | 1:5 | MilliQ water | 37 | 7 |

Results
Synthesis of $NH_2PhAs(III)$

The ESI-mass spectrum (FIG. 33) shows reaction products formed from the reduction of p-arsanilic acid to produce $NH_2PhAs(III)$. The desired As(III) compound p-aminophenyldichloroarsine was successfully produced as indicated by the peak at m/z 259.0, assigned as $[NH_2\text{-}Ph\text{-}As\text{-}Cl_2+Na]^+$. In addition, the peak at m/z 184.0 corresponds to $[NH_2\text{-}Ph\text{-}As=O+H]^+$, while the peak at m/z 202.0 corresponds to $[NH_2\text{-}Ph\text{-}As\text{---}(OH)_2+H]^+$, suggesting the formation of a second As(III) compound, p-aminophenylarsine oxide. The peak at m/z 279.1 indicates the presence of triphenylphosphine oxide, $[P(Ph)_3O+H]^+$, which is an expected side product formed as a result of the oxidation of triphenylphosphine.

The $^1H$ NMR spectrum also suggests the formation of two major products due to the presence of two sets of multiplets in the region δ=7.36-7.76 ppm. Ioannou and Tsivgoulis reported the synthesis of pure p-aminophenyldichloroarsine, whereby doublets were present at δ=7.19 ppm and δ=7.70 ppm. From this information, it is reasonable to assume that the multiplet at δ=7.71 ppm, and the multiplet related to it, δ=7.47 ppm, can be assigned as p-aminophenyldichloroarsine protons. Therefore, the large multiplets present at δ=7.42 ppm and δ=7.54 ppm can be assigned as protons associated with either p-aminophenylarsine oxide or p-aminophenyl-dihydroxyarsine. Due to the relatively large abundance of the peak associated with p-aminophenylarsine oxide (m/z 184.0) in the ESI mass spectrum, it is reasonable to assume that the reduction of p-arsanilic acid by triphenylphosphine and iodine resulted in the formation of two major products: p-aminophenyldichloroarsine, and p-aminophenylarsine oxide.

XAS was also used to characterise the As reaction products from formation of $NH_2PhAs(III)$. FIG. 34 shows the aminophenylarsenic products(s) (bottom spectrum) and the As K-edge XANES spectra of some relevant As(III) solid standards: arsenite, $PhAs(GS)_2$ and PAO and the As(V) starting material: p-arsanilic acid. As anticipated, the As(III) species exhibited edge energies and white line peaks approximately 3-5 eV lower than the As(V) compound, p-arsanilic acid (white line peak energies: arsenite, 11871.54 eV; PAO, 11870.57 eV; $PhAs(GS)_2$, 11869.55 eV; p-arsanilic acid, 11874.56 eV). When we consider the XANES spectra generated from arsenite versus PAO, it is apparent that the coordination of the As to the phenyl ring in PAO (compared to O atoms in arsenite) results in an edge shift to lower energy. The binding of As to two GS ligands in addition to a phenyl group in $PhAs(GS)_2$ resulted in a further edge shift to lower energy. Examination of the near post-edge structure for $PhAs(GS)_2$ showed a substantial depression in absorption intensity at approximately 11874 eV. $NH_2PhAs(III)$ gave rise to a white line peak at 11871.80 eV, which is indicative of an As(III) species. The peak is relatively wide, and the shape (pre-edge region and post edge region) is dissimilar to the spectrum of PAO. The post-edge region shows a strong similarity to the post-edge region of the XANES spectrum of p-arsanilic acid. This together with the broadness of the post-edge region may be indicative of a mixture p-aminophenyldichloroarsine and p-aminophenylarsine oxide.

Formation of $NH_2PhAs(LHP)$

Following the successful synthesis of the p-aminophenylarsenic compound (containing two species, p-aminophenyldichloroarsine and p-aminophenylarsine oxide), a number of reaction conditions were employed to identify the optimum reaction conditions to produce the desired aminophenylarsenic-peptide complex(es). Firstly, the temperature of each reaction was maintained at a constant 37° C. to minimise potential degradation of any products. Due to the costly nature of LHP, the As compound was used in excess. While the reaction was rapid at all reactant stoichiometric ratios, it was decided that the ideal stoichiometry was 3 mol As:1 mol LHP. The optimal solvent/pH of the reaction solution was determined to be MilliQ water (pH 7) (cf. phosphate buffer (pH 8)) since the purification of the reaction in phosphate buffer by preparative HPLC yielded approximately ten times less product. Although the reaction was rapid, and formation of the desired complex readily occurred, the reaction was incubated at 37° C. for approximately 24 hours to ensure complete conjugation of the As compound to the peptide.

The ESI-mass spectrum (FIG. 35) of the reaction solution of $NH_2PhAs(III)$ and LHP using the optimal conditions shows the formation of the desired aminophenylarsenic (LHP) complex. The formation of the desired complex is confirmed by the peaks at m/z 462.4 $([NH_2\text{-}Ph\text{-}As(LHP)+3H]^{3+})$ and m/z 693.0 $([NH_2\text{-}Ph\text{-}As(LHP)+2H]^{2+})$. Unreacted p-aminophenyldichloroarsine (m/z 259.1) is evident in the spectrum, since this reagent was added in excess. Small amounts of free LHP are evident in the spectrum (m/z 407.2, 610.1), and may be attributed to fragmentation by the ESI-MS process.

Once the existence of $NH_2PhAs(LHP)$ was confirmed by ESI-MS, separation by HPLC was performed. The fractions that eluted at 8.6 min, 10.5 min and 12.2 min were analysed by ESI-MS and were identified as species relating to NH$_2$PhAs(III). The desired NH$_2$PhAs(LHP) complex eluted at 13.0 min (large peak).

The synthesised NH$_2$PhAs(LHP) was characterised by XAS (FIG. 34). It is clear from the position of the edge energy and the white line peak energy (11870.04 eV) that the product is an As(III) species. Importantly, there is a significant difference in the post-edge region of the NH$_2$PhAs (LHP) spectrum and that obtained from the products of the reaction to form NH$_2$PhAs(III). Firstly, the white line peak is narrower, suggesting a purer product. Secondly, the shoulder at approximately 11874 eV is similar in shape to that of PhAs(GS)$_2$, and much more pronounced than that of arsenite or PAO. Since the post-edge depression is indicative of As bound to S, it is also reasonable to assume that the As is bound to the peptide, although EXAFS analysis was also performed to confirm this.

FIG. 36 shows the best single-scattering fit (for the first coordination shell) and the EXAFS data recorded for the synthesised NH$_2$PhAs(LHP). The peaks at R+Δ(Å)>3 are most likely due to interactions of the ejected electron with the phenyl ring bound to the As atom. The As atom is likely bound to 2S and 1C.

The characterisation data confirms the successful synthesis of NH$_2$PhAs(LHP).

Synthesis of ClPhAs(V)

The compound, ClPhAs(V), was successfully synthesised by the diazotisation of p-arsanilic acid and subsequent coupling of Cl. The ESI mass spectrum (FIG. 37) indicates formation of the desired product (m/z 236.9, [Cl-Ph-AsH$_2$O$_3$+H]$^+$). The peak at m/z 219.0 corresponds to the para substituted hydroxy phenylarsonic acid ([OH-Ph-AsH$_2$O$_3$+H]$^+$), which may be produced as a side product in diazotisation reactions.

Analysis of the synthesised p-chlorophenylarsonic acid by $^1$H NMR showed the presence of one major structure, with two sets of multiplets present at δ=7.76 ppm and δ=7.69 ppm.

The yield of p-chlorophenylarsonic acid was approximately 24%. Other synthetic methods are available to synthesise this compound, such as via the Bart Reaction, whereby alkali arsenite is coupled to an aryldiazonium, formed from p-chloroaniline. The yield is typically between 60-80%. The diazotisation of p-arsanilic acid and subsequent coupling of Cl, used in this work, however, was preferable since this method can also be used to produce p-iodophenylarsonic acid and possibly p-bromophenylarsonic acid using the same precursor, p-arsanilic acid, with the slight modification of the addition of potassium iodide and potassium bromide, respectively.

Further characterisation of the synthesised p-chlorophenylarsonic acid was performed by XAS. FIG. 38 shows the As K-edge XANES spectra of the As(III) and As(V) solid standards, as well as p-chlorophenylarsonic acid. The p-chlorophenylarsonic acid gave rise to a white line peak at 11874.55 eV, which is indicative of an As(V) species, and is almost identical to that of p-arsanilic acid, confirming the As bound to Ph and O atoms.

Formation of ClPhAs(LHP)

LHP was reacted with p-chlorophenylarsonic acid. In all trials to identify the optimum reaction conditions to produce the desired Cl-PhAs(LHP) compound, LHP was kept in excess. This was to ensure p-chlorophenylarsonic acid was sufficiently reduced prior to conjugation to LHP. Different reactant ratios were tested in order to determine the optimum reaction conditions, whereby all of the trials, showed production of ClPhAs(LHP) (confirmed by ESI-MS). Importantly, the presence of ClPhAs(LHP) was not observed before 16 h, suggesting that the reduction to As(III) and subsequent conjugation is not rapid. After incubation at 37° C. for approximately 24 h, peaks corresponding to ClPhAs (LHP) were present in the ESI mass spectrum, as well as peaks related to oxidised LHP i.e. cyclic LHP joined by S—S. The ESI mass spectrum for this reaction after 72 h is shown in FIG. 39. The peaks at m/z 468.8 and m/z 702.5 correspond to the desired chlorophenylarsenic-peptide structure ([Cl-Ph-As(LHP)+3H]$^{3+}$ and ([Cl-Ph-As(LHP)+2H]$^{2+}$, respectively). The ions indicated by the peaks at m/z 406.8 and m/z 609.5 correspond to oxidised LHP ([oxidised LHP+ 3H]$^{3+}$ and [oxidised LHP+2H]$^{2+}$, respectively).

Once ESI-MS confirmed the production of ClPhAs(LHP), separation by HPLC was performed. ESI-MS of the fraction eluted at 17.1 min was identified as oxidised LHP. Two significant fractions were eluted at 22.1 min and 22.4 min. Both of these fractions were almost identical when analysed by ESI-MS, whereby they both contained the desired ClPhAs(LHP) complex.

As was the case for the previously described PhAs(LHP) complex, it is postulated that the differing elution times were reflective of the existence of two spontaneously interconverting As isomers.

Preliminary cell toxicity studies showed that the products from each HPLC fraction exhibit the same toxicity in K562 cells (human chronic myelogenous leukaemia), which is consistent with the racemisation of the isomers.

XAS analysis of ClPhAs(LHP) was conducted to determine the nature of the atoms coordinated to As and its oxidation state. FIG. 38 shows the As K-edge XANES spectra of the As standards and ClPhAs(LHP). The white line peak energy of the ClPhAs(LHP) complex was 11870.31 eV, indicating an As(III) species. The significant post peak depression at approximately 11874 eV is present in this spectra, which is similar to that of PhAs(GS)$_2$, and is consistent with that expected for As(III) coordination to the peptide.

FIG. 40 shows the single-scattering fit (first coordination shell) for the EXAFS data recorded for ClPhAs(LHP), in which the scatterers are 2S and 1C. As per the NH$_2$PhAs (LHP) EXAFS fit, the peaks at R+Δ(Å)>3 in the Fourier transform experimental spectrum that do not align with the fit are due to the interaction of the ejected electron with the phenyl ring adjacent to As which occurs beyond the first coordination shell. The characterisation data of confirms the successful synthesis of the desired complex, ClPhAs(LHP).

Synthesis of IPhAs(V)

p-Iodophenylarsonic acid was successfully synthesised by the diazotisation of p-arsanilic acid and subsequent coupling of I. Yield of IPhAs(V) was approximately 30%.

The ESI mass spectrum (FIG. 41) indicated formation of the desired product (m/z 328.8, [I-Ph-AsH$_2$O$_3$+H$^+$]$^+$). Analysis of the synthesised p-iodophenylarsonic acid by $^1$H NMR showed the presence of one major structure, in which two sets of multiplets were present at δ=8.00 ppm and δ=7.51 ppm The synthesised p-iodophenylarsonic acid was also characterised by XAS. FIG. 42 shows the As K-edge XANES spectra of the As(III) and As(V) solid standards, as well as p-iodophenylarsonic acid. The near edge X-ray spectra for p-iodophenylarsonic acid shows a white line peak at 11874.8 eV, indicating an As(V) species. The edge energy is also similar to that of p-arsanilic acid, confirming the As bound to Ph and O atoms.

Formation of IPhAs(LHP)

The As(V) species, IPhAs(V), was reacted with LHP, relying on the thiol groups in the peptide to reduce the arsonic acid group prior to conjugation with the peptide. The reduction of p-iodophenylarsonic acid was not rapid, generally taking at least 72 h before the phenylarsenic-peptide complex was formed. The ESI mass spectrum for this reaction (after 72 h) is shown in FIG. 43. The peaks at m/z 499.3 and m/z 748.5 correspond to the desired iodophenylarsenic-peptide structure ([I-Ph-As(LHP)+3H]$^{3+}$ and ([I-Ph-As(LHP)+2H]$^{2+}$ respectively). The ions indicated by the peaks at m/z 406.8 and m/z 609.5 correspond to oxidised LHP ([oxidised LHP+3H]$^{3+}$ and [oxidised LHP+2H]$^{2+}$ respectively).

HPLC purification resulted in a fraction eluted at 17.1 min which was confirmed by ESI-MS to be oxidised LHP. Two significant fractions were eluted (22.8 min and 23.2 min), in which ESI-MS showed the desired IPhAs(LHP) complex. These were shown to be the interconverting isomers as previously described for PhAs(LHP) and ClPhAs(LHP).

Preliminary toxicity studies of p-iodophenylarsonic acid showed that the two isomers elicited the same toxicity in the K562 cell line, which was consistent with the spontaneous racemisation of the complex in solution.

The IPhAs(LHP) complex was analysed by XAS. FIG. 42 shows the As K-edge XANES spectra of the As standards and the IPhAs(LHP) complex. The white line peak energy for the IPhAs(LHP) complex was 11869.79 eV. As per the other XPhAs(LHP) spectra, the depression in the shoulder region of the IPhAs(LHP) spectra is similar to that in the PhAs(GS)$_2$ spectrum, consistent with an As(III) complex bound to S.

FIG. 44 shows the single-scattering fit (first coordination shell) for the EXAFS data recorded for IPhAs(LHP), whereby the scatterers are 2S and 1C. Again, the peaks at R+Δ(Å)>3 in the Fourier transform experimental spectrum, that do not align with the fit, can be attributed to the interaction of the ejected electron with the phenyl ring adjacent to As (beyond the first coordination shell). The characterisation data of IPhAs(LHP) confirms the successful synthesis of the desired complex. It is concluded that the IPhAs(LHP) complex exists as a mixture of two enantiomers (chiral centre at As) that spontaneously racemise in solution over time.

In summary, a number of p-substituted analogues of PhAs(LHP) that encompass electron withdrawing, electron donating and sterically hindering groups have been synthesised. Future experiments will involve full purification and characterisation of all of these complexes prior to testing in biological assays to determine the optimal complex for potential therapeutic use. The biological testing will reflect those protocols and the cell lines already described above.

The above description of various embodiments of the present invention is provided for purposes of description to one of ordinary skill in the related art. It is not intended to be exhaustive or to limit the invention to a single disclosed embodiment. As mentioned above, numerous alternatives and variations to the present invention will be apparent to those skilled in the art of the above teaching. Accordingly, while some alternative embodiments have been discussed specifically, other embodiments will be apparent or relatively easily developed by those of ordinary skill in the art. Accordingly, this patent specification is intended to embrace all alternatives, modifications and variations of the present invention that have been discussed herein, and other embodiments that fall within the spirit and scope of the above described invention.

In the claims which follow and in the preceding description of the invention, except where the context clearly requires otherwise due to express language or necessary implication, the word "comprise", or variations thereof including "comprises" or "comprising", is used in an inclusive sense, that is, to specify the presence of the stated integers but without precluding the presence or addition of further integers in one or more embodiments of the invention.

The invention claimed is:

1. An anti-cancer agent comprising a cyclised tumour homing peptide having an arsenic atom bonded to two cysteine residues,
wherein the anti-cancer agent has a structure as shown in formula I or formula II:

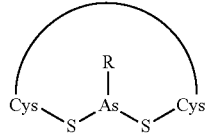

formula I

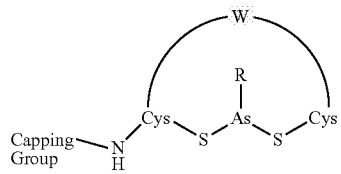

formula II wherein, in formula I:
the sulfur atoms shown and to which the arsenic is bonded are thiol sulfurs of the two cysteine residues;
the two cysteine residues in formula I are separated by between 2 and 20 amino acid residues represented by the curved line; and
R is a stabilizing group selected from the group consisting of hydroxyl, $C_1$ to $C_6$ alkyl, $C_2$ to $C_6$ alkenyl, $C_2$ to $C_6$ alkynyl, $C_1$ to $C_6$ alkoxy, aryl, cycloalkyl, heterocyclic, and short chain peptides, each of which groups may be substituted or unsubstituted; and wherein, in formula II:
the atoms and groups are as described for formula I;
the capping group is formed from an amino reactive compound; and
W is between 2 and 20 amino acid residues;

wherein the tumour homing peptide to which the arsenic atom is bonded between the two cysteine residues is selected from the group consisting of:
1. CAYHRLRRC;
2. CDCRGDCFC;
3. CPIEDRPMC;
4. CNRRTKAGC;
5. CGTKRKC;
6. CRGDGWC;
7. CVSNPRWKC;
8. CHVLWSTRC;
9. CLDGGRPKC;
10. CVNHPAFAC;
11. CRGDRGPDC;
12. CRGDKTTNC;
13. CRGDHAGDC;
14. CLSYYPSYC;

15. CTPSPPFSHC;
16. CPHSKPCLC;
17. CSDSWHYWC;
18. CSDWQHPWC;
19. CSDYNHHWC;
20. CSDGQHYWC;
21. CYDSWHYWC;
22. CFDGNHIWC;
23. CTDFPRSFC;
24. CTQDRQHPC;
25. CLSRYLDQC;
26. CRGDCF;
27. CGNSNPKSC; and
28. CPHNLTKLC;
wherein the arsenic atom, when in the formed anti-cancer agent, is bonded to and bridged between the two cysteine residues of the above peptide sequences.

2. A pharmaceutical composition comprising an anti-cancer agent and a pharmaceutically acceptable carrier, diluent and/or excipient wherein the anti-cancer agent comprises a cyclised tumour homing peptide having an arsenic atom bonded to two cysteine residues,
wherein the anti-cancer agent has a structure as shown in formula I or formula II:

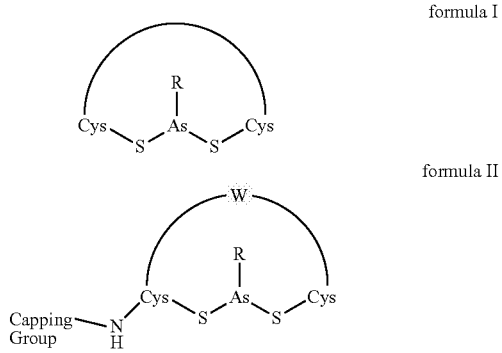

wherein, in formula I:
the sulfur atoms shown and to which the arsenic is bonded are thiol sulfurs of the two cysteine residues;
the two cysteine residues in formula I are separated by between 2 and 20 amino acid residues represented by the curved line; and
R is a stabilizing group selected from the group consisting of hydroxyl, $C_1$ to $C_6$ alkyl, $C_2$ to $C_6$ alkenyl, $C_2$ to $C_6$ alkynyl, $C_1$ to $C_6$ alkoxy, aryl, cycloalkyl, heterocyclic, and short chain peptides, each of which groups may be substituted or unsubstituted; and
wherein, in formula II:
the atoms and groups are as described for formula I;
the capping group is formed from an amino reactive compound; and
W is between 2 and 20 amino acid residues.

3. A method of treating a cancer in a patient including the step of administering the pharmaceutical composition of claim 2 to the patient, to thereby treat the cancer in the patient.

4. The method of claim 3 wherein the cancer is a haematological malignancy or a solid tumour.

5. The method of claim 3 wherein the cancer is selected from a leukemia, multiple myeloma, and a lymphoma.

6. The method of claim 3 wherein the cancer is selected from the group consisting of squamous cell carcinoma, basal cell carcinoma, melanoma, tumours of the epithelial lining of glands or ducts, adenocarcinoma, papillary carcinoma, papillary adenocarcinoma tumours of the liver and biliary tract, hepatocellular carcinoma tumours of the gastrointestinal tract, squamous cell carcinoma of the oesophagus, adenocarcinoma of the oesophagus, colorectal carcinoma (colon cancer), gastric carcinoma (stomach cancer), tumours of the respiratory tract, bronchogenic carcinoma, small cell carcinoma, large cell carcinoma, tumours of the urogenital tract, transitional cell carcinomas of the bladder, squamous cell carcinoma of the bladder, carcinoma of the prostate, carcinoma of the cervix, blood cells and related cells (leukemias), acute and chronic lymphocytic leukemia, polycythemia vera, cancers of lymphoid tissue, malignant lymphomas including Hodgkin's lymphoma and non-Hodgkin's lymphoma, follicular lymphoma, diffuse lymphoma, small lymphocytic lymphoma, large cell lymphoma, lymphoblastic lymphoma, multiple myeloma, tumours of connective tissue, cancers of bone osteosarcoma, tumours of the nervous system, neuroblastoma, retinoblastoma, glioblastoma, oligodendroglioma, tumours associated with oncogenic viruses, Burkitts lymphoma, b cell lymphoma's in immuno-comprised individuals, nasopharyngeal carcinoma, esophagus and gastroesophageal cancers, epidermal squamous cell cancers, pancreatic islet tumours, breast carcinoma, lung cancer, colorectal cancer, retinoblastoma, hepatic cancer, pancreatic cancer, brain cancer, mesothelioma and hepatitis b virus hepatocellular carcinoma.

7. The method of claim 3 wherein the cancer is selected from the group consisting of chronic myeloid leukemia, t-cell lymphoma, myelodysplastic syndrome, colon cancer, pancreatic cancer, brain cancer, mesothelioma and acute promyelocytic leukemia (APL).

8. A process for producing an anti-cancer agent including the steps of:
(a) contacting a tumour homing peptide comprising two cysteine residues with an arsenic compound; and
(b) allowing the arsenic to become bound to each of the two cysteine residues to form a cyclised tumour homing peptide comprising a bound arsenic atom;
to thereby produce the anti-cancer agent;
wherein the arsenic compound is an oxide of arsenic;
wherein the anti-cancer agent comprises a cyclised tumour homing peptide having an arsenic atom bonded to two cysteine residues,
wherein the anti-cancer agent has a structure as shown in formula I or formula II:

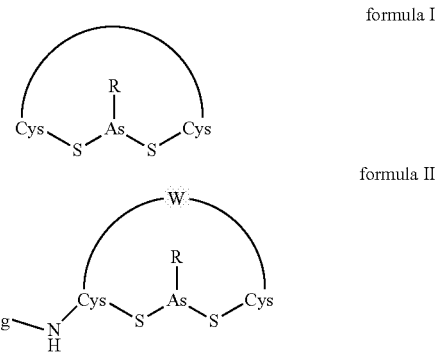

wherein, in formula I:
the sulfur atoms shown and to which the arsenic is bonded are thiol sulfurs of the two cysteine residues;
the two cysteine residues in formula I are separated by between 2 and 20 amino acid residues represented by the curved line; and
R is a stabilizing group selected from the group consisting of hydroxyl, $C_1$ to $C_6$ alkyl, $C_2$ to $C_6$ alkenyl, $C_2$ to $C_6$ alkynyl, $C_1$ to $C_6$ alkoxy, aryl, cycloalkyl, heterocyclic, and short chain peptides, each of which groups may be substituted or unsubstituted; and wherein, in formula II:
the atoms and groups are as described for formula I
the capping group is formed from an amino reactive compound; and
W is between 2 and 20 amino acid residues.

9. The process of claim 8 wherein the arsenic compound further comprises an alkyl, hydroxyl or aryl group bonded to the arsenic.

10. A method of diagnosing a cancer including the steps of:
administering an anti-cancer agent to a patient;
(ii) allowing the anti-cancer agent to become localised to the cancer; and
(iii) detecting the presence of the at least one radiolabelled atom of the anti-cancer agent, to thereby diagnose the cancer;
wherein the anti-cancer agent comprises at least one radiolabelled atom, and comprises a cyclised tumour homing peptide having an arsenic atom bonded to two cysteine residues,
wherein the anti-cancer agent has a structure as shown in formula I or formula II:

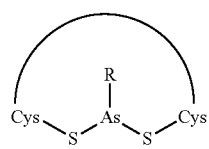

formula I

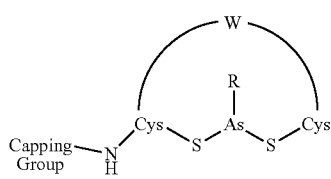

formula II wherein, in formula I:
the sulfur atoms shown and to which the arsenic is bonded are thiol sulfurs of the two cysteine residues;
the two cysteine residues in formula I are separated by between 2 and 20 amino acid residues represented by the curved line; and
R is a stabilizing group selected from the group consisting of hydroxyl, $C_1$ to $C_6$ alkyl, $C_2$ to $C_6$ alkenyl, $C_2$ to $C_6$ alkynyl, $C_1$ to $C_6$ alkoxy, aryl, cycloalkyl, heterocyclic, and short chain peptides, each of which groups may be substituted or unsubstituted; and wherein, in formula II:
the atoms and groups are as described for formula I;
the capping group is formed from an amino reactive compound; and
W is between 2 and 20 amino acid residues.

11. An anti-cancer agent comprising a cyclised tumour homing peptide having an arsenic atom bonded to two cysteine residues,
wherein the anti-cancer agent has a structure as shown in formula I or formula II:

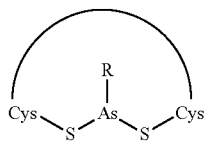

formula I

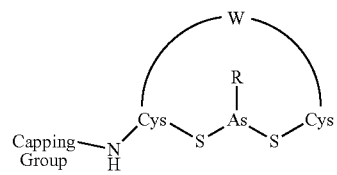

formula II wherein, in formula I:
the sulfur atoms shown and to which the arsenic is bonded are thiol sulfurs of the two cysteine residues;
the two cysteine residues in formula I are separated by between 2 and 20 amino acid residues represented by the curved line; and
R is a stabilizing group selected from the group consisting of hydroxyl, $C_1$ to $C_6$ alkyl, $C_2$ to $C_6$ alkenyl, $C_2$ to $C_6$ alkynyl, $C_1$ to $C_6$ alkoxy, aryl, cycloalkyl, heterocyclic, and short chain peptides, each of which groups may be substituted or unsubstituted; and wherein, in formula II:
the atoms and groups are as described for formula I;
the capping group is formed from an amino reactive compound; and
W is between 2 and 20 amino acid residues;
wherein the capping group is an alkanoyl group which is optionally substituted.

12. The anti-cancer agent of claim 11, wherein the capping group is an acetyl group.

13. The pharmaceutical composition of claim 2, wherein R is selected from the group consisting of hydroxyl, $C_1$ to $C_6$ alkyl, and aryl.

14. The process of claim 8, wherein the process further comprises the step (a)(i) of modifying a selected tumour homing peptide to present two cysteine residues.

15. The method of claim 3, wherein the anti-cancer agent is administered in combination with one or more of an immunotherapeutic, monoclonal antibody, chemotherapeutic, radioprotectant and radiotherapeutic.

16. The pharmaceutical composition of claim 2 wherein the tumour homing peptide comprises at least one arginine and/or lysine residue.

17. The pharmaceutical composition of claim 2, wherein the anti-cancer agent has the structure as shown in formula I.

18. The pharmaceutical composition of claim 2, wherein the anti-cancer agent has the structure as shown in formula II.

19. The pharmaceutical composition of claim 2, wherein the tumour homing peptide to which the arsenic atom is bonded between the two cysteine residues is selected from the group consisting of:
1. CAYHRLRRC;
2. CDCRGDCFC;
3. CPIEDRPMC;
4. CNRRTKAGC;
5. CGTKRKC;
6. CRGDGWC;
7. CVSNPRWKC;
8. CHVLWSTRC;
9. CLDGGRPKC;
10. CVNHPAFAC;
11. CRGDRGPDC;
12. CRGDKTTNC;
13. CRGDHAGDC;
14. CLSYYPSYC;
15. CTPSPPFSHC;
16. CPHSKPCLC;
17. CSDSWHYWC;
18. CSDWQHPWC;
19. CSDYNHHWC;
20. CSDGQHYWC;
21. CYDSWHYWC;
22. CFDGNHIWC;
23. CTDFPRSFC;
24. CTQDRQHPC;
25. CLSRYLDQC;
26. CRGDCF;
27. CGNSNPKSC; and
28. CPHNLTKLC;
wherein the arsenic atom, when in the formed anti-cancer agent, is bonded to and bridged between the two cysteine residues of the above peptide sequences.

* * * * *